United States Patent
Kosley, Jr. et al.

(10) Patent No.: US 7,777,042 B2
(45) Date of Patent: Aug. 17, 2010

(54) N-SULFONYLPIPECOLIC ACID DERIVATIVE FKBP BINDING COMPOSITION AND PHARMACEUTICAL USE THEREOF

(75) Inventors: Raymond W. Kosley, Jr., Bridgewater, NJ (US); Bruce Baron, Westfield, NJ (US); Patrick Jimonet, Villepreux (FR); John G. Jurcak, Bethlehem, PA (US); Stephen J. Shimshock, Hillsborough, NJ (US); Xu-Yang Zhao, Bridgewater, NJ (US); Rosy Sher, Bridgewater, NJ (US); Paul J. Mueller, Hoboken, NJ (US); Jennifer Beall, Geneva, IL (US); Matthieu Barrague, Union City, NJ (US); Joseph W. Guiles, Lafayette, CO (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/567,421

(22) Filed: Dec. 6, 2006

(65) Prior Publication Data

US 2008/0139556 A1    Jun. 12, 2008

Related U.S. Application Data

(63) Continuation of application No. PCT/US2005/022360, filed on Jun. 24, 2005.

(60) Provisional application No. 60/583,740, filed on Jun. 29, 2004, provisional application No. 60/624,946, filed on Nov. 4, 2004.

(51) Int. Cl.
*A61K 31/535* (2006.01)
*C07D 211/30* (2006.01)

(52) U.S. Cl. .................................. 546/225; 514/235.5

(58) Field of Classification Search ................. 546/207, 546/225; 514/316, 235.5
See application file for complete search history.

(56) References Cited

U.S. PATENT DOCUMENTS

| 5,696,135 | A | 12/1997 | Steiner et al. |
| 6,268,384 | B1 | 7/2001 | Novak et al. |
| 7,022,677 | B1 * | 4/2006 | Ishiyama et al. .............. 514/19 |
| 2002/0052372 | A1 | 5/2002 | Steiner et al. |
| 2002/0052410 | A1 | 5/2002 | Steiner et al. |

FOREIGN PATENT DOCUMENTS

| WO | WO 98/53814 | | 12/1998 |
| WO | WO 00/48623 | * | 8/2000 |

OTHER PUBLICATIONS

F. Z. Dorwald "Side Reactions in Organic Synthesis: A Guide to Successful Synthesis Design" 2005, Wiley-VCH Verlag GmbH and KGaA, Wienheim.*
Solomons, T.W. and Fryle, C.B. Organic Chemistry $9^{th}$ Ed., 2008, pp. 183-184.*
Donkor, I.O., et. al., Peptidyl Aldehyde Inhibitors of Calpain Incorporating P2-Proline Mimetics, Bioorganic & Medicinal Chemistry Letters vol. 13, (2003) pp. 783-784.

* cited by examiner

*Primary Examiner*—Rita J Desai
*Assistant Examiner*—John Mabry
(74) *Attorney, Agent, or Firm*—Balaram Gupta

(57) ABSTRACT

A composition for binding FKBP proteins is disclosed, along with a method of treating conditions associated with neuronal degeneration, wherein said composition comprises a compound of formula I,

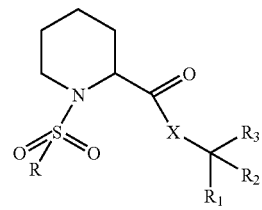

wherein, R, $R_1$, $R_2$, $R_3$ and X are as defined herein.

10 Claims, 2 Drawing Sheets

Human IFNγ promoter (3.2 KB):

AACATACGGCTCTCCATCAAAACAAACGAAACAAACCAAACTAGCAAAATAGGCTGTCCCCAGTGC
AAGTGCAGGTGCCGACTTTCTCTATCGATAGGTACCGAGCTCCACCGCGGTGGCGGCCGCTCTAGAA
CTAGTGGATCCCACTATTCTTAACTCCTCAATCCTAGTACTACATTCCAGTGGAGCAATCAAGGACCA
GGCAGAACTAATTTTTACTTATTTCCAGACAGTTGGGAACATTCCTTCCAGTGACTCAGAGGTTGGGC
ATTGGAAGGTATTGAGAACCTGCAAAGTGTCTCAGGCTCTGACCCAAATCCCTGTGCCACCTGCAAG
CACGTTCTCTGGACGTAATTTTTCTTGAGCAGAGCAACAGTAGAGCTTTGTATGCAACAATGTAATTT
TTACATTCTTCACTTGCTTAACATGAGGTTTGGTTCCACATAAATGTTTTGATCTTATTTATTCTTTGG
GAAGATCGCCCCTCAAAGAGCTTTCTGGCTTTTTTTTCCCACATAAAAGAATACACGAAATTGTCGCA
GTCAGCAAGTGTTGGCTAAAGAGACACAGCATCATGTTTCTAACATTAATCATAAATATTATTTAATT
AAAAACTAGTTTCTTACAGGTTAGGCCTGATAACATCGGAATTAGAATTTGAGGGCAAATAACTCAA
AAGAGAGCCTTAGGCAAGCATTCGAATTTACATTTATTCAGTGCTCTTTATGAGCAAATCTCCATGCT
AAAATATTTTAGGGAAGAGAAAGCCATCATAAAAGCAATGAAACAATTTCTGATTTTCAGAAACTCA
ATCTAACATGGCAGAAGACACGCGAATAGCTATCTTCAATCAAGATTGAGGAATCAGAACTCTTAGA
AAAGTATAAACCAAGACTTGTATAGAGAATCTAAGATTAATTTTAAGGAGGATAATTTTGGAAAAAC
TCAGGGAGATGGTAATTTTTAAGCCGGGCTTGGATGGATGGCTACTACTCTCAGGGGCACAAATGAG
GGGAAAAAGAACTCAAGACCAAAGAAACAGCATGAGCAAAGGTCCAGGGTACTTTTTTTTTTTTTT
TTAAAGAAATGACTAGGCCGGGTGCGGTGGCTCACGCCTGTAATCCCAGCACTTTGGGAGGCCAAGG
CGGGCGGATCACGAGGTCAGGAGATCGAGACCATCCTGATTAACACAGTGAAACCCCGTCTGTACTA
AAAATAGCACAAAAAAAAAAAAAAAAAAAAATTACCCSGGCGTGGCGAGTGCCTGTAGTCCCAGCTA
CTCGGGAGGCTGAGGCGGGAGAATGGCGTGAATCCGGGAGGCAGAGCTTGCAGTGAGCCGAGATTG
CGCCACTGCACTCCA
GCCTGGGTGACAGAGCAAGACTCCGTCTCAAAAAAAAAAAAAAAAAAAAAAGAAATGACTAGTCATC
CAATGTGCCAAAATAATAATAAACTTTTATTAGTGATTACTATATGCCAGGAAAAATTCCTAGCACTT
TATGAGGATTACCTGATTTAATTTTCAACTGAAGCATGGAAGAAGATACTATTATCAAGCCAGTTTTA
CAGGTAAGGAGACTGAGTCATAGAAGATTTAAGAAGCTAACTCACAATCATATAGCTAGATAGTAG
AGAAAACAGGAATCAAGTTTGCCCCATAACTGCAATACTGTTATGTACACAGTACAGGTAGAAATGC
AAAGTGGGTTTGAACCAAAGAGTGGAGGGCTTTTTGTGCCATCCCAAAGTGTTGTACTTCATAAATA
AATTACAAAGGAGGAGAAAGAATCCTATTTTTTTTTGTATCTGAAAGACAAAGAAATAAAAAGTTA
AAAAGATTCTCTGTTAGTACTGATTATTTGGAACAATAAATTGTTTAGAGCTATGCTGTTCAATATAG
TAGYCACCTAGCAGTATGTGCCCATTAAGCGTTTGAAATACGACTAGACCAAATTGAGATGCACCGT
AGGCTTAAAATATACACTGTATTTCTTTCCTTTTTTCTTTTTTTCTTTTTTTTTTTGAGACGGAATCTT
ACTCCCGTCACCTAGGCTGGAGTGTAGTGGCGCGATCTCGGCTCACTGCAACCTCCACCTTTCTTGGG
TTCAAGCCATTCTCCTGCCTCAGCCTCCCTAGTAGCTGAGATTACAGGCATACACCACCATGCCTGGC
TAATTTTTTGTATTTTTAGTAGAGATGGGGTTTCACCATATTGGCTAGGCTGGTCTCAAACTCCTGAC
CTTGTGATCCACCCGCCTCAACCTCCCAAAGTGCTGGGATTACAGGTGTGAGCCACTGCGTCTGGAA
CTCCCCCTGGGAATATTCTCTACACTGTATTTCAAGGAGTTTAATATGACAAAAAGAATGTCAAATAC
CTTATTAACAATGTAGTATATTGATGCATACTGAAGTACTATTTGGGATATATTGGTTTAAATACAAT
ATATTTTAAAATTATATTTACCTTTTAAAAAAACTTTTATTAATGAGGCTACTAGATCATTTAAATTTA
CCTGTGTGGCTTGTATTGTATTTCTACTGGGCAGTGCTGATCTAGAGCAATTTGAAACTTGTGGTAGA
TATTTTACTAACCAACTCTGATGAAGGACTTCCTCACCAAATTGTTCTTTTAACCGCATTCTTTCCTTG
CTTTCTGGTCATTTGCAAGAAAAATTTTAAAAGGCTGCCCCTTTGTAAAGGTTTGAGAGGCCCTAGAA
TTTCGTTTTTCACTTGTTCCCAACCACAAGCAAATGATCAATGTGCTTTGTGAATGAAGAGTCAACAT
TTTACCAGGGCGAAGTGGGGAGGTACAAAAAAATTTCCAGTCCTTGAATGGTGTGAAGTAAAAGTGC
CTTCAAAGAATCCCACCAGAATGGCACAGGTGGGCATAATGGGTCTGTCTCATCGTCAAAGGACCCA
AGGAGTCTAAAGGAAACTCTAACTACAACACCCAAATGCCACAAAACCTTAGTTATTAATACAAACT
ATCATCCCTGCCTATCTGTCACCATCTCATCTTAAAAAACTTGTGAAAATACGTAATCCTCAGGAGAC
TTCAATTAGGTATAAATACCAGCAGCCAGAGGAGGTGCAGCACATTGTTCTGATCATCTGAAGATCA
GCTATTAGAAGAGAAAGATCAGTTAAGTCCTTTGGACCTGATCAGCTTGATACAAGAACTACTGATT
TCAACTTCTTTGGC
TTAATTCTCTCGGAAACG

FIGURE 1

Homo sapiens FK506 binding protein 1A, 12kDa; NCBI Locus BC005147
Gene sequence: nucleotides 1 to 706
Coding sequence: nucleotides 32 to 358
Amino acid sequence:
MGVQVETISPGDGRTFPKRGQTCVVHYTGMLEDGKKFDSSRDRNK
PFKFMLGKQEVIRGWEEGVAQMSVGQRAKLTISPDYAYGATGHPG
IIPPHATLVFDVELLKLE

```
  1 gccgcccgcc cgctcagcgt ccgccgccgc catgggagtg caggtggaaa ccatctcccc
 61 aggagacggg cgcaccttcc ccaagcgcgg ccagacctgc gtggtgcact acaccgggat
121 gcttgaagat ggaaagaaat tgattcctc ccgggacaga aacaagccct taagtttat
181 gctaggcaag caggaggtga tccgaggctg ggaagaaggg gttgcccaga tgagtgtggg
241 tcagagagcc aaactgacta tatctccaga ttatgcctat ggtgccactg gcacccagg
301 catcatccca ccacatgcca ctctcgtctt cgatgtggag cttctaaaac tggaatgaca
361 ggaatggcct cctcccttag ctccctgttc ttgggtaagg aaatggaata ctgaagggcc
421 cttcactgcc tttgctcctc ccatgttatg cccagcgttt gatgggtagc agagagaaca
481 aaaaacacca caaggctatt tttccccctg cattctttct gtattgagta tcctttcagt
541 gttattagtg tatgctttga atgtaaaaat tggtcaccct aaggaaagga attggcatgt
601 gtatgttccc agttcaactc atggagatgg cagctgttta aatgtttttc tatgtagttt
661 ataaattaaa actgaattga ggactatgaa aaaaaaaaa aaaaaa
```

FIGURE 2

N-SULFONYLPIPECOLIC ACID DERIVATIVE FKBP BINDING COMPOSITION AND PHARMACEUTICAL USE THEREOF

BACKGROUND OF THE INVENTION

1. Field of the Invention

This invention relates to compositions that bind to FKBP proteins and to their use for treating neurological diseases. The invention also relates to methods of treating neurological diseases with these compositions.

2. Description of the Related Art

The diseases treated by compounds or compositions of the invention are major health problems and they are poorly addressed by current therapies. Patients seek medical attention after the disease or traumatic injury that has resulted in damage to the brain or peripheral nervous system. Drug treatments are available which offer symptomatic treatment for Parkinson's or Alzheimer's disease (e.g. dopamine or acetylcholine replacement therapies, respectively).

Neurological diseases are associated with the death of or injury to neuronal cells. For example, the loss of dopaminergic neurons in the substantia nigra is believed to be the basis for Parkinson's disease. Although the molecular mechanism of neurodegeneration in Alzheimer's disease is yet to be established, inflammation and deposition of beta-amyloid protein and other such agents may compromise neuronal function or survival. In patients suffering from brain ischemia or spinal cord injuries, extensive neuronal cell death is observed. Currently, there are no satisfactory treatments for these diseases.

One approach to treating neurological diseases involves the use of drugs capable of inhibiting neuronal cell death. A more recent approach involves the promotion of nerve regeneration by drugs which stimulate neurite outgrowth.

Recently, small molecules have been shown to stimulate axonal outgrowth in vivo. In individuals suffering from a neurological disease, this stimulation of neurite outgrowth may protect neurons from further degeneration, and accelerate the regeneration of nerve cells. For example, estrogen has been shown to promote the growth of axons and dendrites, which are neurites sent out by nerve cells to communicate with each other in a developing or injured adult brain [C. Dominique Toran-Allerand et al., J. Steroid Biochem. Mol. Biol., 56, pp. 169-78 (1996); and B. S. McEwen et al., Brain Res. Dev. Brain. Res., 87, pp. 91-95 (1995)]. The progress of Alzheimer's disease may be slowed in women who take estrogen. Estrogen is hypothesized to complement NGF (nerve growth factor) and other neurotrophins and thereby help neurons differentiate and survive.

It has been reported that compounds with an affinity for the FK506 binding protein (FKBP) also possess nerve growth stimulatory activity [Lyons et al., PNAS, 91, pp. 3191-3195 (1994)]. Many of these compounds also have immunosuppressive activity, which could be a deleterious side effect in treating a human subject having a neurological disease.

FK506 (Tacrolimus), an immunosuppressive drug which binds to FKBP12 and other FKBP proteins, has been demonstrated to act synergistically with NGF in stimulating neurite outgrowth in PC12 cells as well as sensory ganglia [Lyons et al., Proc Nat. Acad. Sci. (1994)]. This compound has also been shown to be neuroprotective in focal cerebral ischemia [J. Sharkey and S. P. Butcher, Nature, 371, pp. 336-339 (1994)] and to increase the rate of axonal regeneration in injured sciatic nerve [B. Gold et al., J. Neurosci., 15, pp. 7509-16 (1995)].

More recently, sub-classes of FKBP binding compounds which lack immunosuppressive activity have been disclosed for use in stimulating nerve growth [see for example U.S. Pat. Nos. 5,614,547; 5,696,135; WO 96/40633; WO 96/40140; WO 97/16190; J. P. Steiner et al., Proc. Natl. Acad. Sci. USA, 94, pp. 2019-23 (1997); and G. S. Hamilton et al., Bioorg. Med. Chem. Lett., 7, pp. 1785-90 (1997)]. These compounds supposedly avoid certain unwanted side effects of immunosuppressive FKBP binding compounds but still bind to FKBP and alter its functioning.

Some compounds bearing a similarity to those of the present invention are disclosed in a published patent application, US 2002/0052410 A1 (published May 2, 2002). However, that application does not disclose or suggest the compounds of the present invention.

Furthermore, other compounds bearing a similarity to those of the present invention have been disclosed in another published patent application, US 2002/0052372 A1 (published May 2, 2002). However that application also fails to disclose or suggest the compounds of the present invention.

SUMMARY OF THE INVENTION

We have now discovered a class of compounds that are effective for treating nerve damage.

The present invention relates to neurotrophic, low molecular weight, small molecule compounds having an affinity for FKBP-type immunophilins. Once bound to these proteins, the compounds are potential potent modulators of the function of immunophilin proteins.

Specifically, the present invention relates to compounds including enantiomers, stereoisomers, rotamers and tautomers of said compounds and pharmaceutically acceptable salts, solvates or derivatives thereof, said compounds having the general structure shown in formula I:

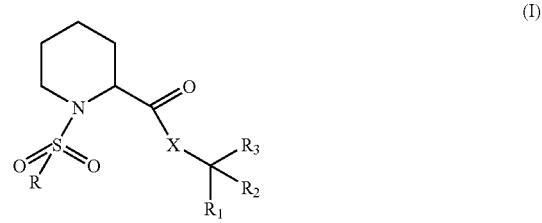

(I)

wherein:
R is fluoroalkyl of the formula $C_nH_xF_y$, wherein n is an integer from 1 to 6, x is an integer from 0 to 12, y is an integer from 1 to 13 and the sum of x and y is 2n+1, aryl, aryl $C_{1-6}$ alkyl, aryl $C_{2-4}$ alkenyl, wherein aryl is selected from phenyl, biphenyl and naphthyl, heteroaryl or heteroaryl $C_{1-4}$ alkyl, wherein heteroaryl is selected from pyridyl, thiophenyl and benzothiophenyl, and heterocyclyl selected from piperidinyl and piperazinyl, $R_1$ is hydrogen or $C_{1-6}$ alkyl;

$R_2$ is $CONHR_4$, benzimidazol-2-yl, $CR_5R_6OH$, or $CR_7R_8NHR_9$;

$R_3$ is aryl, aryl $C_{1-4}$ alkyl or aryl $C_{2-4}$ alkenyl, wherein aryl is selected from phenyl, biphenyl, naphthyl, bisarylmethyl, heteroaryl and heteroaryl $C_{1-4}$ alkyl, wherein heteroaryl is selected from indolyl, thiophenyl, benzothiophenyl, furanyl, benzofuranyl, 1,3-benzodioxolyl, 1,4-benzodioxanyl and $C_{5-7}$ cycloalkyl $C_1$ alkyl;

X is $NR_{10}$ or $CH_2$;
wherein:
$R_4$ is selected from the group consisting of hydrogen, $C_{1-10}$ alkyl, $C_{2-10}$ alkenyl, $C_{3-8}$ cycloalkyl, $C_{8-12}$ bicycloalkyl, $C_{10-14}$ tricycloalkyl, $C_{3-8}$ cycloalkyl $C_{1-6}$ alkyl, $C_{8-12}$ bicycloalkyl $C_{1-6}$ alkyl, $C_{8-12}$ bicycloalkylamino-$C_{1-6}$ alkyl, $C_{8-12}$ tricycloalkylamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$, wherein n is an integer from 1 to 20, x is an integer from 0 to 40, y is an integer from 1 to 41 and the sum of x and y is 2n+1, amino $C_{2-20}$ alkyl, mono or dialkylamino $C_{2-20}$ alkyl, mono-, di-, or trihydroxy $C_{2-20}$ alkyl, $C_{1-6}$ alkoxy-$C_{2-20}$ alkyl, $C_{1-20}$ thioalkyl, $C_{1-6}$ alkyl-thio-$C_{2-20}$ alkyl, hydroxy-$C_{2-6}$-alkoxy-$C_{2-6}$ alkyl, $C_{1-6}$ alkyl-bis-(hydroxy-$C_{1-6}$ alkyl), aryl, aryl $C_{1-10}$ alkyl, aryl $C_{3-4}$ alkenyl, wherein aryl is selected from phenyl, biphenyl, indanyl and naphthyl, heteroaryl or heteroaryl $C_{1-10}$ alkyl, wherein heteroaryl is selected from pyridyl, thiophenyl, furanyl, benzofuranyl, benzothiophenyl, pyrrolidinyl, and indolyl; heterocycloalkyl or heterocycloalkyl $C_{1-10}$ alkyl wherein heterocycloalkyl is selected from tetrahydrofuranyl, tetrahydropyranyl, morpholinyl, piperidinyl, pyrrolidinyl, tetrahydrothiophenyl, piperazinyl, dioxolanyl, sulfolanyl and 1,1-dioxotetrahydrothiopyranyl; heterobicyclyl of the formula:

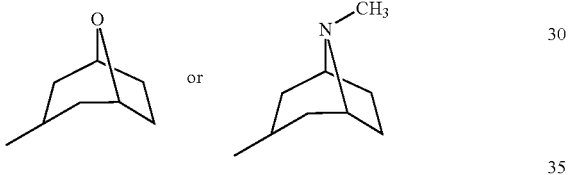

comprising $C_{5-8}$ cycloalkyl, $C_{8-12}$ bicycloalkyl, and/or heterocyclyl, optionally substituted with one or more substituents selected from the group consisting of $C_{1-10}$alkyl, $C_{1-10}$ alkoxy, hydroxy, hydroxy $C_{1-10}$ alkoxy, hydroxy $C_{1-10}$ alkyl, $C_{1-10}$ acyloxy, amino, $C_{1-10}$ alkylcarbonylamino, hydroxy $C_{1-20}$ alkylcarbonylamino, amino $C_{2-10}$ alkoxy, mono-$C_{1-6}$-alkylamino-$C_{2-10}$-alkoxy, di-$C_{1-6}$-alkylamino-$C_{2-10}$-alkoxy, mono-($C_{1-10}$alkyl)amino, di-($C_{1-10}$ alkyl) amino, amino $C_{1-10}$ alkylcarbonylamino, $C_{1-10}$ alkylaminocarbonyl, hydroxy $C_{1-10}$ alkylaminocarbonyl, amino $C_{2-10}$ alkylaminocarbonyl, mono or dialkylamino $C_{1-10}$ alkylaminocarbonyl, oxo, optionally substituted aryl and optionally substituted heteroaryl, wherein aryl is selected from phenyl, naphthyl and biphenyl, and heteroaryl is selected from pyridyl and thiophenyl; and
wherein:
the aryl or heteroaryl groups of R are optionally substituted with one or more substituents selected from the group consisting of fluorine, chlorine, bromine, $C_{1-20}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-20}$ alkoxy, $C_{1-20}$ alkenyloxy, $C_{1-10}$-alkoxy-$C_{1-10}$-alkoxy, hydroxy, hydroxy $C_{1-20}$ alkoxy, hydroxy $C_{1-20}$ alkyl, $C_{1-20}$ acyloxy, hydroxy $C_{1-20}$ acyl, nitro, amino, aminosulfonyl, $C_{1-20}$ alkylcarbonylamino, hydroxy $C_{1-20}$ alkylcarbonylamino, amino $C_{2-20}$ alkoxy, amino $C_{1-20}$ alkylcarbonylamino, $C_{1-20}$ alkylaminocarbonyl, hydroxy $C_{1-20}$ alkylaminocarbonyl, amino $C_{1-20}$ alkylaminocarbonyl, mono or dialkylamino $C_{1-20}$ alkylaminocarbonyl, optionally substituted aryl or heteroarylsulfonyl, aminosulfonyl, mono- or di($C_{1-6}$) alkylaminosulfonyl, optionally substituted phenyl or thiophenyl, optionally substituted phenyl or thiophenyl $C_{1-10}$ alkyloxy, and cyano;
wherein:
the phenyl or thiophenyl substituent on the aryl or heteroaryl group of R is optionally substituted with one or more substituents selected from the group consisting of fluorine, chlorine, bromine, $C_{1-5}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-10}$alkoxy, $C_{1-10}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, hydroxy $C_{1-20}$-alkyloxo, nitro, amino, aminosulfonyl, $C_{1-10}$ alkylcarbonylamino, hydroxy $C_{1-10}$ alkylcarbonylamino, amino $C_{2-10}$ alkoxy, amino $C_{1-10}$ alkylcarbonylamino, $C_{1-10}$ alkylaminocarbonyl, hydroxy $C_{1-10}$ alkylaminocarbonyl, amino $C_{1-10}$ alkylaminocarbonyl, mono or dialkylamino $C_{1-10}$ alkylaminocarbonyl, optionally substituted aryl $C_{1-10}$ alkyloxy, and cyano;
wherein:
the aryl or heteroaryl of $R_3$ is optionally substituted with one or more substituents selected from the following: $C_{3-8}$ cycloalkyloxy, $C_{1-10}$ alkoxy, $C_{1-10}$ alkyl, $C_{2-10}$ alkenyl, $C_{3-10}$ alkenyloxy, mono-($C_{1-6}$-alkyl)amino-$C_{2-6}$alkyloxy, di-($C_{1-6}$ alkyl)amino-$C_{2-6}$-alkyloxy, amino-$C_{2-6}$alkyloxy, heterocyclyl-$C_{2-6}$alkyloxy, aryl-$C_{2-6}$-alkyloxy, heteroaryl-$C_{2-6}$-alkyloxy, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-6}$-alkoxy-$C_{2-6}$-alkoxy, aryl-$C_{1-6}$-alkyloxy, hydroxy, chloro, fluoro, bromo, hydroxy-$C_{1-6}$-alkoxy, hydroxy-$C_{1-10}$ alkyl, $C_{1-6}$ alkyloxo, cyano, amino, 4-aryloxo, di-$C_{1-5}$ alkylphosphityl-$C_{1-5}$ alkyl, $C_{1-6}$ alkyloxoamino, $C_{1-6}$ alkyloxo($C_{1-6}$ alkyl)amino, $C_{1-10}$alkylsulfonyl, arylsulfonyl, carboxy, $C_{1-20}$ carboalkoxy, dialkylamino-$C_{1-10}$ alkyl, monoalkylamino-$C_{1-10}$ alkyl, and amino-$C_{1-10}$ alkyl;
wherein: the heterocycloalkyl substituent group attached to the alkyloxy group of $R_3$ is selected from the following: pyrrolidinyl, morpholinyl, piperidinyl, and piperazinyl;
wherein: the heteroaryl substituent group attached to the alkyloxy group of $R_3$ is selected from pyridinyl, and pyrrolidinyl;
wherein: the aryl of the arylsulfonyl substituent on the aryl of $R_3$ is selected from phenyl, indolyl, thiophenyl, and furanyl;
wherein:
the aryl or heteroaryl groups of $R_4$ are optionally substituted with one or more substituents selected from the following: mono- or di-($C_{1-6}$ alkyl)amino, mono- or di($C_{1-6}$)alkylamino-$C_{2-6}$ alkyl, amino-$C_{1-6}$ alkyl, heterocycloalkyl, amino, $C_{1-20}$ alkoxy, chloro, fluoro, bromo, $C_{1-10}$ alkyl, aryl and heteroaryl;
wherein:
the heterocycloalkyl group attached to the aryl of $R_4$ is selected from the following: morpholinyl, pyrrolidinyl, piperazinyl, and piperidinyl;
wherein: the heteroaryl group attached to the aryl of $R_4$ is selected from pyridyl, pyrrolyl, and furanyl;

$R_5$, $R_6$=independently H, or $C_{1-6}$ alkyl;
$R_7$, $R_8$=independently H, or $C_{1-6}$ alkyl;
$R_9$=di-($C_{1-5}$ alkyl)amino-$C_{2-4}$ alkyl; mono($C_{1-5}$ alkyl) amino-$C_{2-4}$ alkyl; amino-$C_{2-4}$ alkyl; or heterocycloalkyl methyl in which heterocycloalkyl is selected from the group consisting of thiophenyl, furanyl, pyrrolyl, and pyridinyl; and
$R_{10}$=H, or $C_{1-6}$ alkyl.

The compounds of the invention have been evaluated for binding affinity at human FK506 binding protein FKBP12. Compounds have been identified with inhibition constants (Ki) better than 1 micromolar, many with Ki better than 100 nM. Compounds of this structural type penetrate cells and bind to FK506 binding proteins, whereby they influence intracellular signaling pathways. Activity is typically evident at concentrations of 1 μM (micromolar) or less.

The new compounds disclosed herein should be useful for treating disorders involving neurological damage, including, but not limited to, disorders such as Parkinson's disease, multiple sclerosis, Alzheimer's disease, stroke, and spinal cord injury.

BRIEF DESCRIPTION OF THE DRAWINGS

FIG. 1 shows the nucleotide sequence of the Human IFN-gamma 3.2 kilobase promoter used as described below.

FIG. 2 shows the nucleotide sequence of the *Homo sapiens* FK506 binding protein 1A, 12 kiloDalton, transcript variant 12A, LOCUS: BC005147, used as described below.

However, the figures that were originally filed in the provisional applications and the PCT from which the present application derives its' priority were somehow inadvertently missing when the present continuation application was filed in the U.S.P.T.O. The Figures referred to above are now also attached hereto for incorporation in the application. This amendment is being filed as a supplement to the amendment and response filed on Oct. 17, 2008. Please grant Applicants a second one (1) month extension of time if necessary.

Since the present application claims priority from the original filed U.S. provisional application 60/583,740 filed on Jun. 29, 2004 and PCT/US2005/22360, both of which included said Sequence listings comprising said drawings (as set forth as FIGS. 1 and 2) and claimed on the Application Data Sheet and the Transmittal Letter to the U.S.P.T.O. when this application was filed, said sequences depicted in FIGS. 1 and 2 do not constitute new matter and it is respectfully submitted that said figures be incorporated into the pending U.S. application as filed. A Statement Regarding the Content of Paper and Computer Readable Copies Pursuant to 37 C.F.R. §1.821 is also being filed with the computer readable listing currently herewith.

DETAILED DESCRIPTION OF THE INVENTION

The compounds disclosed herein may be effectively used in treating a disease state that involves neurodegeneration in its etiology and progression. Such disease states include Parkinson's disease, multiple sclerosis, Alzheimer's disease, organic brain disorder, memory dysfunction, neuropathies, peripheral neuropathies, trigeminal neuralgia, glossopharyngeal neuralgia, Bell's palsy, myasthenia gravis, muscular dystrophy, progressive muscular atrophy, and traumatic injury to spinal, peripheral, or central nervous system tissue.

Peripheral nerve trauma may be used as a test of potential efficacy for such disorders as those listed above. Such a test may be performed as follows: Sciatic or facial nerve is mechanically crushed, and animals (rats or mice) are monitored for behavioral and neurological deficits (e.g. abnormal gait or inability to move the whiskers). Compounds or vehicle are administered at least once daily beginning at the time of injury and continuing throughout the observation period. After 3 weeks, the animals are euthanized, and nerve integrity is visualized histologically. The number, caliber, and myelination state of axons in the damaged nerve are quantitated. Compound efficacy is reflected as a reduction of neurological deficits and an increase in the total number of axons, and especially the fraction of large caliber myelinated fibers.

Clinically, this finding would be exploited by giving a suitable dose of the compound by mouth or by injection to a patient suffering from a traumatic injury, such as a crush or a laceration of a peripheral nerve.

Unless defined otherwise herein, all technical and scientific terms used herein have the same meaning as is commonly understood by one of skill in the art to which this invention belongs. All patents and publications referred to herein are hereby incorporated herein by reference.

The compounds of formula I as well as the intermediates and starting materials used in their preparation are named in accordance with IUPAC rules of nomenclature in which characteristic groups have decreasing priority for citation as the principle group as follows: acids, esters, amides, etc. Alternatively, the compounds are named by AutoNom 4.0 (Beilstein Information Systems, Inc.).

As used in the present application, the following definitions apply:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below. Unless otherwise specified herein, "alkyl" indicates $C_1$-$C_6$.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents.

Illustrative examples of cycloalkyl groups include, but are not limited to, the following moieties:

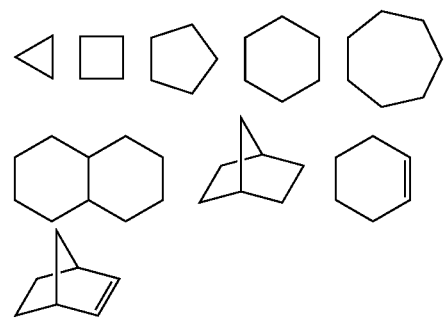

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen, and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to the following moieties:

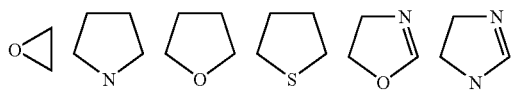

An "aryl group" is intended to mean an aromatic, monovalent monocyclic, bicyclic, or tricyclic radical containing 6, 10, 14, 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, the following moieties:

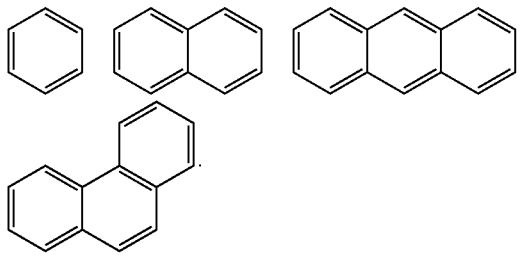

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, the following moieties: benzothiophenyl, thiophenyl and furanyl.

An "acyl group" is intended to mean a —C(O)—R radical, wherein R is any suitable substituent as defined below.

An "aminosulfonyl group" is intended to mean a —SO$_2$NH$_2$ radical.

The term "suitable substituent" is intended to mean any of the substituents recognizable, such as by routine testing, to those skilled in the art as not adversely affecting the binding activity of the inventive compounds. Illustrative examples of suitable substituents include, but are not limited to, hydroxy groups, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "suitable organic moiety" is intended to mean any organic moiety recognizable, such as by routine testing, to those skilled in the art as not adversely affecting the binding activity of the inventive compounds. Illustrative examples of suitable organic moieties include, but are not limited to, hydroxy groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

A "hydroxy group" is intended to mean the radical —OH.

An "amino group" is intended to mean the radical —NH$_2$.

An "alkylamino group" is intended to mean the radical —NHR where R is an alkyl group as defined above.

A "dialkylamino group" is intended to mean the radical —NR$_a$R$_b$ where R$_a$ and R$_b$ are each independently an alkyl group as defined above.

An "alkoxy group" is intended to mean the radical —OR where R is an alkyl group as defined above, for example, methoxy, ethoxy, propoxy, and the like.

A "dialkylaminocarbonyl group" is intended to mean the radical —C(O)NR$_a$R$_b$ where R$_a$ and R$_b$ are each independently an alkyl group as defined above.

A "carboxy group" is intended to mean the radical —C(O)OH.

"Optional" or "optionally" means that the subsequently described event or circumstance may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. Unless otherwise specified herein, "optionally substituted" refers to either mono- or di-substitution.

A "pharmaceutically acceptable solvate" is intended to mean a solvate that retains the biological effectiveness and properties of the biologically active components of compounds of formula I. Examples of pharmaceutically acceptable solvates include, but are not limited to, compounds of formula I in combination with water, isopropanol, ethanol, methanol, DMSO, ethyl acetate, acetic acid, or ethanolamine.

A "pharmaceutically acceptable salt" is intended to mean a salt that retains the biological effectiveness and properties of the free acids and bases of compounds of formula I and that is not biologically or otherwise undesirable. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acids such as glucouronic acid and galactouronic acid; alpha-hydroxy acids such as citric acid and tartaric acid; amino acids such as aspartic acid and glutamic acid; aromatic acids such as benzoic acid and cinnamic acid; sulfonic acids such as p-toluenesulfonic acid or ethanesulfonic acid; and the like.

If the inventive compound is an acid, the desired salt may be prepared by any suitable method known to the art, including treatment of the free acid with an inorganic or organic base, such as an amine (primary, secondary or tertiary); an alkali metal or alkaline earth metal hydroxide; or the like. Illustrative examples of suitable salts include organic salts derived from amino acids such as glycine and arginine; ammonia; primary, secondary and tertiary amines; and cyclic amines such as piperidine, morpholine, and piperazine, and inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention.

The inventive compounds may exist as single stereoisomers, racemates, and/or mixtures of enantiomers and/or diastereomers. All such single stereoisomers, racemates, and mixtures thereof are intended to be within the scope of the present invention. Preferably, the inventive compounds are used in optically pure form.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, an "effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms. The amount of a compound of formula (I) which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein cover administration to a subject by any manner in which the symptoms of a condition, disorder or disease are ameliorated or otherwise beneficially altered; where the condition, disorder or disease is characterized by neurodegenerative activity; and include:
(i) preventing the disease-state from occurring in a human, in particular, when such human is predisposed to the disease-state but has not yet been diagnosed as having it;
(ii) inhibiting the disease-state, i.e., slowing or arresting its development; or
(iii) relieving the disease-state, i.e., causing regression of the disease-state.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, the $IC_{50}$ refers to an amount, concentration or dosage of a particular test compound that achieves a 50% inhibition of a maximal response, such as binding of FK506 to an FKBP, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Specifically, the present invention relates to compounds, including enantiomers, stereoisomers, rotamers and tautomers of said compounds and pharmaceutically acceptable salts, solvates or derivatives thereof, said compounds having the general structure shown in formula I:

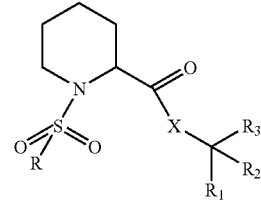

(I)

wherein:
R is fluoroalkyl of the formula $C_nH_xF_y$, wherein n is an integer from 1 to 6, x is an integer from 0 to 12, y is an integer from 1 to 13 and the sum of x and y is 2n+1, aryl, aryl $C_{1-6}$ alkyl, aryl $C_{2-4}$ alkenyl, wherein aryl is selected from phenyl, biphenyl and naphthyl, heteroaryl or heteroaryl $C_{1-4}$ alkyl, wherein heteroaryl is selected from pyridyl, thiophenyl and benzothiophenyl, and heterocyclyl selected from piperidinyl and piperazinyl,
$R_1$ is hydrogen or $C_{1-6}$ alkyl;
$R_2$ is $CONHR_4$, benzimidazol-2-yl, $CR_5R_6OH$, or $CR_7R_8NHR_9$;
$R_3$ is aryl, aryl $C_{1-4}$ alkyl or aryl $C_{2-4}$ alkenyl, wherein aryl is selected from phenyl, biphenyl, naphthyl, bisarylmethyl, heteroaryl and heteroaryl $C_{1-4}$ alkyl, wherein heteroaryl is selected from indolyl, thiophenyl, benzothiophenyl, furanyl, benzofuranyl, 1,3-benzodioxolyl, 1,4-benzodioxanyl and $C_{5-7}$ cycloalkyl $C_1$ alkyl;
X is $NR_{10}$ or $CH_2$;
wherein:
$R_4$ is selected from the group consisting of hydrogen, $C_{1-10}$ alkyl, $C_{2-10}$-alkenyl, $C_{3-8}$ cycloalkyl, $C_{8-12}$ bicycloalkyl, $C_{10-14}$ tricycloalkyl, $C_{3-8}$ cycloalkyl $C_{1-6}$ alkyl, $C_{8-12}$ bicycloalkyl $C_{1-6}$ alkyl, $C_{8-12}$ bicycloalkylamino-$C_{1-6}$ alkyl, $C_{8-12}$ tricycloalkylamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$ wherein n is an integer from 1 to 20, x is an integer from 0 to 40, y is an integer from 1 to 41 and the sum of x and y is 2n+1, amino $C_{2-20}$ alkyl, mono or dialkylamino $C_{2-20}$ alkyl, mono-, di, or trihydroxy $C_{2-20}$ alkyl, $C_{1-6}$ alkoxy-$C_{2-20}$ alkyl, $C_{1-20}$ thioalkyl, $C_{1-6}$ alkyl-thio-$C_{2-20}$ alkyl, hydroxy-$C_{2-6}$-alkoxy-$C_{2-6}$ alkyl, $C_{1-6}$ alkyl-bis-(hydroxy-$C_{1-6}$ alkyl), aryl, aryl $C_{1-10}$ alkyl, aryl $C_{3-4}$ alkenyl, wherein aryl is selected from phenyl, biphenyl, indanyl and naphthyl, heteroaryl or heteroaryl $C_{1-10}$ alkyl, wherein heteroaryl is selected from pyridyl, thiophenyl, furanyl, benzofuranyl, benzothiophenyl, pyrrolidinyl, and indolyl; heterocycloalkyl or heterocycloalkyl $C_{1-10}$ alkyl wherein heterocycloalkyl is selected from tetrahydrofuranyl, tetrahydropyranyl, morpholinyl, piperidinyl, pyrrolidinyl, tetrahydrothiophenyl, piperazinyl, dioxolanyl, sulfolanyl and 1,1-dioxotetrahydrothiopyranyl; heterobicyclyl of the formula:

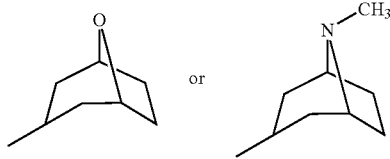

comprising $C_{5-8}$ cycloalkyl, $C_{8-12}$ bicycloalkyl, and/or heterocyclyl, optionally substituted with one or more substituents selected from the group consisting of $C_{1-10}$alkyl, $C_{1-10}$ alkoxy, hydroxy, hydroxy $C_{1-10}$ alkoxy, hydroxy $C_{1-10}$ alkyl, $C_{1-10}$ acyloxy, amino, $C_{1-10}$ alkylcarbonylamino, hydroxy $C_{1-20}$ alkylcarbonylamino, amino $C_{2-10}$ alkoxy, mono-$C_{1-6}$-alkylamino-$C_{2-10}$-alkoxy, di-$C_{1-6}$-alkylamino-$C_{2-10}$-alkoxy, mono-($C_{1-10}$ alkyl)amino, di-($C_{1-10}$ alkyl)amino, amino $C_{1-10}$ alkylcarbonylamino, $C_{1-10}$ alkylaminocarbonyl, hydroxy $C_{1-10}$ alkylaminocarbonyl, amino $C_{2-10}$ alkylaminocarbonyl, mono or dialkylamino $C_{1-10}$ alkylaminocarbonyl, oxo, optionally substituted aryl and optionally substituted heteroaryl, wherein aryl is selected from phenyl, naphthyl and biphenyl, and heteroaryl is selected from pyridyl and thiophenyl; and wherein: the aryl or heteroaryl groups of R are optionally substituted with one or more substituents selected from the group consisting of fluorine, chlorine, bromine, $C_{1-20}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-20}$ alkoxy, $C_{1-20}$ alkenyloxy, $C_{1-10}$-alkoxy-$C_{1-10}$-alkoxy, hydroxy, hydroxy $C_{1-20}$ alkoxy, hydroxy $C_{1-20}$ alkyl, $C_{1-20}$ acyloxy, hydroxy $C_{1-20}$ acyl, nitro, amino, aminosulfonyl, $C_{1-20}$ alkylcarbonylamino, hydroxy $C_{1-20}$ alkylcarbonylamino, amino $C_{2-20}$ alkoxy, amino $C_{1-20}$ alkylcarbonylamino, $C_{1-20}$ alkylaminocarbonyl, hydroxy $C_{1-20}$ alkylaminocarbonyl, amino $C_{1-20}$ alkylaminocarbonyl, mono or dialkylamino $C_{1-20}$ alkylaminocarbonyl, optionally substituted aryl or heteroarylsulfonyl, aminosulfonyl, mono- or di-($C_{1-6}$)alkylaminosulfonyl, optionally substituted phenyl or thiophenyl, optionally substituted phenyl or thiophenyl $C_{1-10}$ alkyloxy, and cyano;

wherein: the phenyl or thiophenyl substituent on the aryl or heteroaryl group of R is optionally substituted with one or more substituents selected from the group consisting of fluorine, chlorine, bromine, $C_{1-5}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-10}$ alkoxy, $C_{1-10}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, hydroxy $C_{1-20}$-alkyloxo, nitro, amino, aminosulfonyl, $C_{1-10}$ alkylcarbonylamino, hydroxy $C_{1-10}$ alkylcarbonylamino, amino $C_{2-10}$ alkoxy, amino $C_{1-10}$ alkylcarbonylamino, $C_{1-10}$ alkylaminocarbonyl, hydroxy $C_{1-10}$ alkylaminocarbonyl, amino $C_{1-10}$ alkylaminocarbonyl, mono or dialkylamino $C_{1-10}$ alkylaminocarbonyl, optionally substituted aryl $C_{1-10}$ alkyloxy, and cyano;

wherein: the aryl or heteroaryl of $R_3$ is optionally substituted with one or more substituents selected from the following: $C_{3-8}$ cycloalkyloxy, $C_{1-10}$ alkoxy, $C_{1-10}$ alkyl, $C_{2-10}$ alkenyl, $C_{3-10}$ alkenyloxy, mono-($C_{1-6}$-alkyl)amino-$C_{2-6}$alkyloxy, di-($C_{1-6}$ alkyl)amino-$C_{2-6}$-alkyloxy, amino-$C_{2-6}$alkyloxy, heterocyclyl-$C_{2-6}$alkyloxy, aryl-$C_{2-6}$-alkyloxy, heteroaryl-$C_{2-6}$-alkyloxy, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-6}$-alkoxy-$C_{2-6}$-alkoxy, aryl-$C_{1-6}$-alkyloxy, hydroxy, chloro, fluoro, bromo, hydroxy-$C_{1-6}$-alkoxy, hydroxy-$C_{1-10}$ alkyl, $C_{1-6}$ alkyloxo, cyano, amino, 4-aryloxo, di-$C_{1-5}$ alkylphosphityl-$C_{1-5}$ alkyl, $C_{1-6}$ alkyloxoamino, $C_{1-6}$ alkyloxo($C_{1-6}$ alkyl)amino, $C_{1-10}$alkylsulfonyl, arylsulfonyl, carboxy, $C_{1-20}$ carboalkoxy, dialkylamino-$C_{1-10}$ alkyl, monoalkylamino-$C_{1-10}$ alkyl, and amino-$C_{1-10}$ alkyl;

wherein: the heterocycloalkyl substituent group attached to the alkyloxy group of $R_3$ is selected from the following: pyrrolidinyl, morpholinyl, piperidinyl, and piperazinyl;

wherein: the heteroaryl substituent group attached to the alkyloxy group of $R_3$ is selected from pyridinyl, and pyrrolidinyl;

wherein: the aryl of the arylsulfonyl substituent on the aryl of $R_3$ is selected from phenyl, indolyl, thiophenyl, and furanyl;

wherein: the aryl or heteroaryl groups of $R_4$ are optionally substituted with one or more substituents selected from the following: mono- or di-($C_{1-6}$ alkyl)amino, mono- or di($C_{1-6}$)alkylamino-$C_{2-6}$ alkyl, amino-$C_{1-6}$ alkyl, heterocycloalkyl, amino, $C_{1-20}$ alkoxy, chloro, fluoro, bromo, $C_{1-10}$ alkyl, aryl and heteroaryl;

wherein: the heterocycloalkyl group attached to the aryl of $R_4$ is selected from the following: morpholinyl, pyrrolidinyl, piperazinyl, and piperidinyl;

wherein: the heteroaryl group attached to the aryl of $R_4$ is selected from pyridyl, pyrrolyl, and furanyl;

$R_5$, $R_6$=independently H, or $C_{1-6}$ alkyl;

$R_7$, $R_8$=independently H, or $C_{1-6}$ alkyl;

$R_9$=di-($C_{1-5}$ alkyl)amino-$C_{2-4}$ alkyl; mono($C_{1-5}$ alkyl)amino-$C_{2-4}$ alkyl; amino-$C_{2-4}$ alkyl, or heterocycloalkyl methyl in which heterocycloalkyl is selected from the group consisting of thiophenyl, furanyl, pyrrolyl, and pyridinyl; and $R_{10}$=H, or $C_{1-6}$ alkyl.

Preferred compounds of the present invention include enantiomers, stereoisomers, rotamers and tautomers of said compounds and pharmaceutically acceptable salts, solvates or derivatives thereof, said compounds having the general structure shown in formula I, wherein:

R is selected from the group consisting of aryl, aryl $C_{1-6}$ alkyl, aryl $C_{2-4}$ alkenyl, wherein aryl is selected from phenyl, biphenyl or naphthyl;

heteroaryl or heteroaryl $C_{1-4}$ alkyl, wherein heteroaryl is selected from pyridyl, thiophenyl or benzothiophenyl; and heterocyclyl selected from piperidinyl or piperazinyl;

$R_1$ is hydrogen or methyl;

$R_2$ is CONHR$_4$, benzimidazol-2-yl, CR$_5$R$_6$OH, or CR$_7$R$_8$NHR$_9$;

$R_3$ is selected from the group consisting of phenyl and aryl $C_{1-4}$ alkyl or aryl $C_{2-4}$ alkenyl, wherein aryl is selected from phenyl, biphenyl, naphthyl or bisarylmethyl, and heteroaryl or heteroaryl $C_{1-4}$ alkyl, wherein heteroaryl is selected from indolyl and thiophenyl.

X is $NR_{10}$ or $CH_2$;

wherein $R_4$ is selected from the group consisting of hydrogen, $C_{1-10}$ alkyl, $C_{2-10}$ alkenyl, $C_{3-8}$ cycloalkyl, $C_{8-12}$ bicycloalkyl, $C_{10-14}$ tricycloalkyl, $C_{3-8}$ cycloalkyl-$C_{1-6}$ alkyl, $C_{8-12}$ bicycloalkyl$C_{1-6}$ alkyl, $C_{8-12}$ bicycloalkylamino-$C_{1-6}$ alkyl, $C_{8-12}$ tricycloalkylamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$, wherein n is an integer from 1 to 10, x is an integer from 0 to 20, y is an integer from 1 to 21 and the sum of x and y is 2n+1, amino $C_{2-10}$-alkyl, mono or dialkylamino $C_{2-10}$ alkyl, mono-, di, or trihydroxy $C_{2-10}$ alkyl, $C_{1-6}$-alkoxy-$C_{2-10}$-alkyl, $C_{1-10}$ thioalkyl, $C_{1-6}$alkyl-thio-$C_{2-10}$alkyl, hydroxy-$C_{2-6}$-alkoxy-$C_{2-6}$ alkyl, $C_{1-6}$alkyl-bis-(hydroxy-$C_{1-6}$alkyl), aryl, aryl $C_{1-6}$ alkyl, and aryl $C_{3-4}$ alkenyl, wherein aryl is selected from phenyl, biphenyl, indanyl and naphthyl, heteroaryl or heteroaryl $C_{1-10}$ alkyl, wherein heteroaryl is selected from pyridyl, thiophenyl, furanyl, benzofuranyl, benzothiophenyl, pyrrolidinyl and indolyl; heterocycloalkyl or heterocycloalkyl $C_{1-10}$ alkyl wherein heterocycloalkyl is selected from tetrahydrofuranyl, tetrahydropyranyl, morpholinyl, piperidinyl, pyrrolidinyl, piperazinyl, dioxolanyl, sulfolanyl and 1,1-dioxotetrahydrothiopyranyl;

wherein $C_{5-8}$ cycloalkyl, $C_{8-12}$ bicycloalkyl, or heterocycloalkyl is optionally substituted with one or more substituents selected from the group consisting of $C_{1-6}$ alkyl, $C_{1-6}$ alkoxy, hydroxy, hydroxy $C_{1-6}$ alkoxy, hydroxy $C_{1-6}$ alkyl, amino, $C_{1-6}$ alkylcarbonylamino, hydroxy $C_{1-6}$ alkylcarbonylamino, amino $C_{2-6}$ alkoxy, mono-$C_{1-6}$-alkylamino-$C_{2-6}$-alkoxy, di-$C_{1-6}$-alkylamino-$C_{2-6}$-alkoxy, mono-($C_{1-6}$ alkyl)amino, di-($C_{1-6}$ alkyl)amino, amino $C_{1-6}$ alkylcarbonylamino, $C_{1-6}$ alkylaminocarbonyl, hydroxy $C_{1-6}$ alkylaminocarbonyl, amino $C_{2-6}$ alkylaminocarbonyl, mono or dialkylamino $C_{1-6}$ alkylaminocarbonyl, oxo, optionally substituted aryl and optionally substituted heteroaryl; wherein aryl is selected from phenyl, naphthyl and biphenyl and heteroaryl is selected from pyridyl and thiophenyl;

wherein: the aryl or heteroaryl groups of R are optionally substituted with one or more substituents selected from the group consisting of fluorine, chlorine, bromine, $C_{1-10}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-10}$ alkoxy, $C_{1-10}$ alkenyloxy, $C_{1-10}$-alkoxy-$C_{1-10}$-alkoxy, hydroxy, hydroxy $C_{1-10}$ alkoxy, hydroxy $C_{1-10}$ alkyl, hydroxy $C_{1-10}$ acyl, nitro, amino, aminosulfonyl, $C_{1-10}$ alkylcarbonylamino, hydroxy $C_{1-10}$ alkylcarbonylamino, amino $C_{2-10}$ alkoxy, amino $C_{1-10}$ alkylcarbonylamino, $C_{1-10}$ alkylaminocarbonyl, hydroxy $C_{1-10}$ alkylaminocarbonyl, amino $C_{1-10}$ alkylaminocarbonyl, mono or dialkylamino $C_{1-10}$ alkylaminocarbonyl, optionally substituted aryl or heteroaryl-sulfonyl, aminosulfonyl, mono- or di($C_{1-6}$) alkylaminosulfonyl, optionally substituted phenyl or thiophenyl, optionally substituted phenyl or thiophenyl $C_{1-10}$ alkyloxy, and cyano;

wherein the phenyl or thiophenyl substituent on the aryl or heteroaryl group of R is optionally substituted with one or more substituents selected from the group consisting of fluorine, chlorine, bromine, $C_{1-5}$ alkyl, $CF_3$, $OCF_3$, $C_{1-6}$ alkoxy, $C_{1-6}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, nitro, amino, aminosulfonyl, $C_{1-10}$ alkylcarbonylamino, hydroxy $C_{1-6}$ alkylcarbonylamino, amino $C_{2-6}$ alkoxy, amino $C_{1-6}$ alkylcarbonylamino, $C_{1-6}$ alkylaminocarbonyl, hydroxy $C_{1-6}$ alkylaminocarbonyl, amino $C_{1-6}$ alkylaminocarbonyl, mono or dialkylamino $C_{1-6}$ alkylaminocarbonyl, optionally substituted aryl $C_{1-6}$ alkyloxy, and cyano;

wherein:

the aryl or heteroaryl of $R_3$ is optionally substituted with one or more substituents selected from the following: $C_{3-6}$ cycloalkyloxy, $C_{1-6}$ alkoxy, $C_{1-6}$ alkyl, $C_{2-6}$ alkenyl, $C_{3-6}$ alkenyloxy, mono-($C_{1-6}$ alkyl)amino-$C_{2-6}$ alkyloxy, di-($C_{1-6}$ alkyl)amino-$C_{2-6}$ alkyloxy, amino-$C_{2-6}$ alkyloxy, heterocyclyl-$C_{2-6}$ alkyloxy, aryl-$C_{2-6}$ alkyloxy, heteroaryl-$C_{2-6}$ alkyloxy, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-6}$ alkoxy-$C_{2-6}$ alkyloxy, aryl-$C_{1-6}$ alkoxy, hydroxy, chloro, fluoro, bromo, hydroxy-$C_{1-6}$alkoxy, hydroxy-$C_{1-10}$alkyl, $C_{1-6}$alkyloxo, cyano, amino, 4-aryloxo, $C_{1-6}$ alkyloxoamino, $C_{1-6}$ alkyloxo($C_{1-6}$ alkyl)amino, carboxy, dialkylamino-$C_{1-6}$ alkyl, monoalkylamino-$C_{1-6}$ alkyl, and amino-$C_{1-6}$ alkyl;

wherein: the heterocyclyl substituent group attached to the alkyloxy group of $R_3$ is selected from the following: pyrrolidinyl, morpholinyl, piperidinyl, and piperazinyl;

wherein: the heteroaryl substituent group attached to the alkyloxy group of $R_3$ is selected from pyridinyl, and pyrrolidinyl;

wherein:

the aryl or heteroaryl groups of $R_4$ are optionally substituted with one or more substituents selected from the following: mono- or di-($C_{1-6}$ alkyl)amino, mono- or di($C_{1-6}$)alkylamino-$C_{2-6}$-alkyl, amino-$C_{1-6}$ alkyl, heterocyclyl, amino, $C_{1-10}$ alkoxy, chloro, fluoro, bromo, $C_{1-10}$ alkyl, aryl and heteroaryl;

wherein the heterocyclyl group attached to the aryl of $R_4$ is selected from the following: morpholinyl, pyrrolidinyl, piperazinyl, piperidinyl;

wherein the heteroaryl group attached to the aryl of $R_4$ is selected from pyridyl, pyrrolyl, and furanyl;

$R_5$, $R_6$=H;

$R_7$, $R_8$=H;

$R_9$=di-($C_{1-5}$ alkyl)amino-$C_{2-4}$ alkyl; mono($C_{1-5}$ alkyl)amino-$C_{2-4}$ alkyl; amino-$C_{2-4}$ alkyl, heterocycloalkyl methyl in which heterocycloalkyl is selected from group consisting of thiophenyl, furanyl, pyrrolyl, pyridinyl; and $R_{10}$=H, $CH_3$.

More preferred compounds according to the present invention include enantiomers, stereoisomers, rotamers and tautomers of said compound and pharmaceutically acceptable salts, solvates or derivatives thereof, said compound having the general structure shown in formula I, wherein:

R is aryl selected from phenyl, biphenyl and naphthyl, or heteroaryl selected from pyridyl and thiophenyl, $R_1$ is hydrogen or methyl, $R_2$ is $CONHR_4$, R₃ is aryl-$C_1$ alkyl wherein aryl is selected from phenyl, biphenyl and naphthyl, or heteroaryl-$C_1$ alkyl, wherein heteroaryl is selected from indolyl and thiophenyl, X is $NR_{10}$, wherein $R_4$ is selected from the group consisting of hydrogen, $C_{1-10}$ alkyl, $C_{2-10}$ alkenyl, $C_{3-8}$ cycloalkyl, $C_{8-12}$ bicycloalkyl, $C_{10-14}$ tricycloalkyl, $C_{3-8}$ cycloalkyl-$C_{1-6}$ alkyl, $C_{8-12}$ bicycloalkyl$C_{1-6}$ alkyl, $C_{8-12}$ bicycloamino-$C_{1-6}$ alkyl, $C_{8-12}$ tricycloamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$, wherein n is an integer from 1 to 6, x is an integer from 0 to 12, y is an integer from 1 to 13 and the sum of x and y is 2n+1, amino $C_{2-8}$ alkyl, mono or dialkylamino $C_{2-8}$ alkyl, mono-, di-, or trihydroxy $C_{2-10}$ alkyl, $C_{1-6}$-alkoxy-$C_{2-10}$ alkyl, $C_{1-6}$ thioalkyl, $C_{1-6}$ alkyl-thio-$C_{2-6}$ alkyl, hydroxy-$C_{2-6}$-alkoxy-$C_{2-6}$ alkyl, $C_{1-6}$ alkyl-bis-(hydroxy-$C_{1-6}$ alkyl), aryl, aryl $C_{1-6}$ alkyl, wherein aryl is selected from phenyl, biphenyl, and naphthyl, heteroaryl or heteroaryl $C_{1-6}$-alkyl, wherein heteroaryl is selected from pyridyl, thiophenyl, heterocycloalkyl or heterocycloalkyl $C_{1-6}$ alkyl wherein heterocycloalkyl is selected from tetrahydrofuranyl, tetrahydropyranyl, morpholinyl, piperidinyl, pyrrolidinyl, and piperazinyl;

wherein: the aryl or heteroaryl groups of R are optionally substituted with one or more substituents selected from the group consisting of fluorine, chlorine, bromine, $C_{1-10}$ alkyl, $CF_3$, $OCF_3$, $C_{1-10}$ alkoxy, $C_{1-10}$ alkenyloxy, $C_{1-5}$ alkoxy-$C_{1-10}$-alkoxy, hydroxy, hydroxy $C_{1-10}$ alkoxy, hydroxy $C_{1-10}$ alkyl, nitro, amino, $C_{1-10}$ alkylcarbonylamino, hydroxy $C_{1-10}$ alkylcarbonylamino, amino $C_{2-10}$ alkoxy, amino $C_{1-10}$ alkylcarbonylamino, optionally substituted phenyl or thiophenyl, optionally substituted phenyl or thiophenyl $C_{1-10}$ alkyloxy, and cyano;

wherein the phenyl or thiophenyl substituent on the aryl or heteroaryl group of R is optionally substituted with one or more substituents selected from the group consisting of fluorine, chlorine, bromine, $C_{1-5}$ alkyl, $CF_3$, $OCF_3$, $C_{1-6}$alkoxy, $C_{1-6}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, nitro, optionally substituted aryl $C_{1-6}$ alkyloxy, and cyano;

wherein: the aryl or heteroaryl of $R_3$ is optionally substituted with one or more substituents selected from: $C_{3-6}$ cycloalkyloxy, $C_{1-6}$ alkoxy, $C_{1-6}$ alkyl, $C_{2-6}$ alkenyl, $C_{3-6}$ alkenyloxy, mono-($C_{1-6}$ alkyl)amino-$C_{2-6}$ alkyloxy, di-($C_{1-6}$ alkyl)amino-$C_{2-6}$-alkyloxy, amino-$C_{2-6}$ alkyloxy, heterocyclyl-$C_{2-6}$ alkyloxy, aryl-$C_{2-6}$-alkyloxy, heteroaryl-$C_{2-6}$-alkyloxy, fluoroalkyl or fluoroalkoxy of the formula $C_nH_xF_y$, or $OC_nH_xF_y$, wherein n is an integer from 1 to 4, x is an integer from 0 to 8, y is an integer from 1 to 9 and the sum of x and y is 2n+1, $C_{1-6}$-alkoxy-$C_{2-6}$-alkoxy, aryl-$C_{1-6}$-alkyloxy, hydroxy, chloro, fluoro, bromo, nitro, hydroxy-$C_{1-6}$-alkoxy, hydroxy-$C_{1-6}$, $C_{1-6}$ alkyloxo, cyano, amino, 4-aryloxo, $C_{1-6}$ alkyloxoamino, carboxy, dialkylamino-$C_{1-6}$ alkyl, monoalkylamino-$C_{1-6}$-alkyl, and amino-$C_{1-6}$ alkyl;

wherein: the heterocycloalkyl substituent group attached to the alkyloxy group of $R_3$ is selected from: pyrrolidinyl, morpholinyl, and piperidinyl;

wherein: the heteroaryl substituent group attached to the alkyloxy group of $R_3$ is selected from pyridinyl, and pyrrolidinyl;

wherein: the aryl or heteroaryl groups of $R_4$ are optionally substituted with one or more substituents selected from the following: mono- or di-($C_{1-6}$-alkyl)amino, mono- or di($C_{1-6}$)alkylamino-$C_{2-6}$-alkyl, amino-$C_{1-6}$-alkyl, heterocycloalkyl, amino, $C_{1-6}$ alkoxy, chloro, fluoro, bromo, $C_{1-6}$-alkyl, aryl and heteroaryl;

wherein the heterocycloalkyl group attached to the aryl of $R_4$ is selected from the following: morpholinyl, pyrrolidinyl, piperazinyl, and piperidinyl; and wherein the heteroaryl group attached to the aryl of $R_4$ is selected from pyridyl and pyrrolyl.

Still more preferred compounds of the invention include compounds of Formula I, wherein:

R is aryl, wherein aryl is selected from phenyl and naphthyl, $R_1$ is hydrogen or methyl, $R_2$ is $CONHR_4$, $R_3$ is aryl-$C_1$-alkyl, wherein aryl is selected from phenyl, indolyl, and thiophenyl;

X is NH wherein $R_4$, is selected from the group consisting of hydrogen, $C_{1-10}$ alkyl, $C_{3-6}$ cycloalkyl, adamantyl, adamantyl-$C_1$-alkyl, 2-adamantylaminoethyl, $C_{3-6}$-cycloalkyl-$C_1$ alkyl, 3-propenyl, trifluoromethyl-$C_1$-alkyl, 4-amino-n-butyl, 4-(methylamino)-n-butyl, 4-(dimethylamino)-n-butyl; 4-diethylaminobutyl, 2-hydroxyethyl, 2-(2-hydroxyethoxy)ethyl, 3-hydroxypropyl, 2-methoxyethylaryl, wherein aryl is selected from phenyl and naphthyl; aryl $C_1$-alkyl, wherein aryl is selected from phenyl, and biphenyl, heteroaryl $C_1$-alkyl, wherein heteroaryl is selected from 2-thiophenyl and 2-pyridinyl, heterocycloalkyl, wherein heterocycloalkyl is selected from 4-tetrahydropyranyl, 4-piperidinyl, 2,2,6,6-tetramethylpiperidinyl and 1-ethyl-4-piperidinyl, heterocycloalkyl-$C_1$-alkyl, wherein heterocycloalkyl is selected from 4-tetrahydropyranyl and 2-tetrahydrofuranyl, 2-heterocycloalkyl-$C_2$-alkyl, wherein heterocycloalkyl is selected from 4-tetrahydropyranyl and 1-piperazinyl;

wherein: the phenyl of R is optionally substituted with one or two substituents in the 3-, 4-, or 5-positions selected from the group consisting of fluorine, chlorine, bromine, trifluoromethyl, $C_{1-7}$ alkyloxy, $C_{1-7}$ alkenyloxy, $C_{1-8}$ alkyl, and $C_{2-3}$ hydroxypropyl;

the naphthyl of R is optionally substituted with one of the substituents selected from chlorine, fluorine, and dimethylamino;

the phenyl of $R_3$ is optionally substituted with one or two substituents selected from the group consisting of $C_{1-5}$ alkyl, $C_{1-5}$ alkyloxy, 2-dimethylaminoethoxy, 2-pyrrolidino-ethoxy, 3-fluoropropyloxy, 3-methoxypropyloxy, cyclopentoxy, benzyloxy, hydroxy, chloro, fluoro, bromo, trifluoromethyl, 1-hydroxyethyl, acetyl, allyloxy, cyano, amino, 4-benzoyl, and acetoxy;

the phenyl of $R_4$ is optionally substituted with one or two substituents selected from the group consisting of 4-dimethylamino, 4-methylamino, 4-amino, methoxy, ethoxy, chloro, 4-morpholino, fluoro, and methyl.

A compound of the present invention, according to Formula I, may also be selected from:

(S)-1-(3-Trifluoromethyl-benzenesulfonyl)-piperidine-2-carboxylic acid [(S)-1-(4-dimethylamino-phenylcarbamoyl)-2-(4-methoxy-phenyl)-ethyl]-amide;

(S)-1-(3-Trifluoromethyl-benzenesulfonyl)-piperidine-2-carboxylic acid [(S)-2-(4-acetyl-phenyl)-1-(4-ethoxy-phenylcarbamoyl)-ethyl]-amide;
(S)-1-(3-Trifluoromethyl-benzenesulfonyl)-piperidine-2-carboxylic acid [(S)-1-(4-morpholin-4-yl-phenylcarbamoyl)-2-(4-trifluoromethyl-phenyl)-ethyl]-amide;
(S)-1-(3-Trifluoromethyl-benzenesulfonyl)-piperidine-2-carboxylic acid [(S)-2-(4-methoxy-phenyl)-1-(tetrahydro-pyran-4-ylcarbamoyl)-ethyl]-amide;
(S)-1-(3-Trifluoromethyl-benzenesulfonyl)-piperidine-2-carboxylic acid [(S)-2-(2-methyl-4-methoxy-phenyl)-1-(tetrahydro-pyran-4-ylcarbamoyl)-ethyl]-amide;
(S)-1-(3-Trifluoromethyl-benzenesulfonyl)-piperidine-2-carboxylic acid [(S)-2-(3,4-dimethoxy-phenyl)-1-(tetrahydro-pyran-4-yl-carbamoyl)-ethyl]-amide;
(S)-1-(3-Trifluoromethyl-benzenesulfonyl)-piperidine-2-carboxylic acid [(S)-2-(4-methoxy-phenyl)-1-(4-morpholin-4-yl-phenylcarbamoyl)-ethyl]-amide;
(S)-1-(3-Methoxy-benzenesulfonyl)-piperidine-2-carboxylic acid ((S)1-carbamoyl-2-phenyl-ethyl)-amide;
(S)-1-(3-Hydroxy-benzenesulfonyl)-piperidine-2-carboxylic acid ((S)-1-carbamoyl-2-phenyl-ethyl)-amide;
(S)-1-(3-Propoxy-benzenesulfonyl)-piperidine-2-carboxylic acid ((S)-1-carbamoyl-2-phenyl-ethyl)-amide;
(S)-1-(3-Trifluoromethyl-benzenesulfonyl)-piperidine-2-carboxylic acid [(S)-2-[4-(1-hydroxy-ethyl)-phenyl]-1-(4-morpholin-4-yl-phenylcarbamoyl)-ethyl]-amide;
(S)-1-(3-Trifluoromethyl-benzenesulfonyl)-piperidine-2-carboxylic acid {(S)-1-(4-ethoxy-phenylcarbamoyl)-2-[4-(1-hydroxy-ethyl)-phenyl]-ethyl}-amide;
(S)-1-(3-Methoxy-benzenesulfonyl)-piperidine-2-carboxylic acid [(S)-2-(indol-3-yl)-1-(naphthalen-2-ylcarbamoyl)-ethyl]-amide;
(S)-1-(3-Trifluoromethyl-benzenesulfonyl)-piperidine-2-carboxylic acid {(S)-1-(4-dimethylamino-phenylcarbamoyl)-2-[4-(1-hydroxy-ethyl)-phenyl]-ethyl}-amide;
(S)-1-(3,5-Dichloro-benzenesulfonyl)-piperidine-2-carboxylic acid [(S)-2-(1H-indol-3-yl)-1-methylcarbamoyl-ethyl]-amide;
(S)-1-(3-Trifluoromethyl-benzenesulfonyl)-piperidine-2-carboxylic acid [(S)-2-(4-acetyl-phenyl)-1-(4-morpholin-4-yl-phenylcarbamoyl)-ethyl]-amide;
(S)-1-(3-Fluoro-benzenesulfonyl)-piperidine-2-carboxylic acid [(S)-2-(4-cyclopentyloxy-phenyl)-1-methyl-1-(tetrahydro-pyran-4-ylcarbamoyl)-ethyl]-amide;
(S)-1-(3-Fluoro-benzenesulfonyl)-piperidine-2-carboxylic acid [(S)-2-(4-isopropoxy-phenyl)-1-(2,2,6,6-tetramethyl-piperidin-4-ylcarbamoyl)-ethyl]-amide;
(S)-1-(3-Fluoro-benzenesulfonyl)-(2S)-piperidine-2-carboxylic acid [(S)-2-[4-(3-fluoro-propoxy)-phenyl]-1-(2,2,6,6-tetramethyl-piperidin-4-ylcarbamoyl)-ethyl]-amide;
(S)-1-(3-Fluoro-benzenesulfonyl)-piperidine-2-carboxylic acid [(S)-2-[4-(3-fluoro-propoxy)-phenyl]-1-((S)-2-methoxy-1-methyl-ethylcarbamoyl)-ethyl]-amide;
(S)-1-(3-Trifluoromethyl-benzenesulfonyl)-piperidine-2-carboxylic acid [(S)-2-(4-isopropoxy-phenyl)-1-methylcarbamoyl-ethyl]-amide;
(S)-1-(3-Trifluoromethyl-benzenesulfonyl)-piperidine-2-carboxylic acid [(S)-2-(4-isopropoxy-phenyl)-1-(tetrahydro-pyran-4-ylcarbamoyl)-ethyl]-amide;
(S)-1-(3-Trifluoromethyl-benzenesulfonyl)-piperidine-2-carboxylic acid [(S)-2-(phenyl)-1-(benzimidazol-2-yl)-ethyl]-amide;
(S)-1-(3-Trifluoromethyl-benzenesulfonyl)-piperidine-2-carboxylic acid [(S)-2-(4-(benzyloxy)phenyl)-1-(benzimidazol-2-yl)-ethyl]-amide;
(S)-1-(3-Fluoro-benzenesulfonyl)-piperidine-2-carboxylic acid [(S)-2-(4-methoxy-phenyl)-1-(tetrahydropyran-4-yl-carbamoyl)-ethyl]-amide;
(S)-1-Benzenesulfonyl-piperidine-2-carboxylic acid ((S)-1-amido-2-(2-methylphenyl)-ethyl)-amide;
(S)-1-Benzenesulfonyl-piperidine-2-carboxylic acid ((S)-1-cyclohexylamido-2-(4-methylphenyl)-ethyl)-amide;
(S)-1-Benzenesulfonyl-piperidine-2-carboxylic acid [(S)-2-(4-allyloxy-phenyl)-1-cyclohexylamido-ethyl]-amide;
(S)-1-(3-Trifluoromethyl-benzenesulfonyl)-piperidine-2-carboxylic acid [(S)-2-(4-allyloxy-phenyl)-1-cyclohexylcarbamoyl-ethyl]-amide;
(S)-1-(3-Trifluoromethyl-benzenesulfonyl)-piperidine-2-carboxylic acid ((S)-1-cyclohexylamido-2-(4-methylphenyl)-ethyl)-amide;
(S)-1-((E)-2-Phenyl-ethenesulfonyl)-piperidine-2-carboxylic acid [(S)-1-amido-2-(1H-indol-3-yl)-ethyl]-amide;
(S)-1-(4,5-Dibromo-thiophene-2-sulfonyl)-piperidine-2-carboxylic acid [(S)-1-amido-2-(1H-indol-3-yl)-ethyl]-amide;
(S)-1-Benzenesulfonyl-piperidine-2-carboxylic acid [(S)-1-tert-butylamido-2-(1H-indol-3-yl)-ethyl]-amide;
(S)-1-Benzenesulfonyl-piperidine-2-carboxylic acid [(S)-1-(3-hydroxy-2,2-dimethyl-propylamido)-2-(4-isopropyl-phenyl)-ethyl]-amide;
(S)-1-Benzenesulfonyl-piperidine-2-carboxylic acid methyl-((S)-1-methylamido-2-(phenyl)-ethyl)-amide;
(S)-1-Benzenesulfonyl-piperidine-2-carboxylic acid [(S)-1-(3,3-dimethyl-butylamido)-2-(4-methoxyphenyl)-ethyl]-amide;
(S)-1-Benzenesulfonyl-piperidine-2-carboxylic acid [(S)-1-(2,2-dimethyl-propylamido)-2-(phenyl)-ethyl]-amide;
(4-{(S)-2-[((S)-1-Benzenesulfonyl-piperidine-2-carbonyl)-amino]-2-amido-ethyl}-benzyl)-phosphonic acid diethyl ester;
(S)-1-Benzenesulfonyl-piperidine-2-carboxylic acid [(S)-2-(4-(acetylamino)-phenyl)-1-amido-ethyl]-amide;
(S)-1-Benzenesulfonyl-piperidine-2-carboxylic acid [(S)-1-amido-2-(4-(hydroxymethyl)-phenyl)-ethyl]-amide;
(S)-1-(Naphthalene-2-sulfonyl)-piperidine-2-carboxylic acid [(S)-1-amido-2-(1H-indol-3-yl)-ethyl]-amide;
(S)-1-(3-Trifluoromethyl-benzenesulfonyl)-piperidine-2-carboxylic acid [(S)-1-(cyclohexylmethyl-amido)-2-(4-methylphenyl)ethyl]-amide;
(S)-1-(3-Trifluoromethyl-benzenesulfonyl)-piperidine-2-carboxylic acid [(S)-1-(4-amino-butylamido)-2-(4-methylphenyl)-ethyl]-amide;
(S)-1-Benzenesulfonyl-piperidine-2-carboxylic acid [(S)-1-amido-2-(1H-indol-3-yl)-ethyl]-amide;
(S)-1-Benzenesulfonyl-piperidine-2-carboxylic acid ((S)-1-amido-2-(pyridin-4-yl)-ethyl)-amide;
(S)-1-Benzenesulfonyl-piperidine-2-carboxylic acid ((S)-1-amido-2-cyclohexyl-ethyl)-amide;
(S)-1-Benzenesulfonyl-piperidine-2-carboxylic acid {(S)-2-phenyl-1-[(thiophen-2-ylmethyl)-amido]-ethyl}-amide;
(S)-1-(3-Fluoro-benzenesulfonyl)-piperidine-2-carboxylic acid [(S)-1-(4-dimethylamino-butylcarbamoyl)-2-(4-fluoro-phenyl)-ethyl]-amide;
(S)-1-(3-Fluoro-benzenesulfonyl)-piperidine-2-carboxylic acid [(S)-2-[4-(3-methoxy-propoxy)-phenyl]-1-(tetrahydro-pyran-4-ylcarbamoyl)-ethyl]-amide;
(S)-1-(3-Trifluoromethyl-benzenesulfonyl)-piperidine-2-carboxylic acid {(S)-1-cyclohexylcarbamoyl-2-[4-(2-dimethylamino-ethoxy)-phenyl]-ethyl}-amide;
(S)-1-(3-Trifluoromethyl-benzenesulfonyl)-piperidine-2-carboxylic acid [(S)-2-(4-methoxy-phenyl)-1-(2-piperazin-1-yl-ethylcarbamoyl)-ethyl]-amide;

(S)-1-(3-Trifluoromethyl-benzenesulfonyl)-piperidine-2-carboxylic acid [(S)-1-(2-hydroxy-1,1-dimethyl-ethylcarbamoyl)-2-(4-methoxy-phenyl)-ethyl]-amide;

(S)-1-Benzenesulfonyl-piperidine-2-carboxylic acid ((S)-1-carbamoyl-2-phenyl-ethyl)-amide;

(S)-1-(3-Fluoro-benzenesulfonyl)-piperidine-2-carboxylic acid {(S)-2-[4-(3-methoxy-propoxy)-phenyl]-1-methylcarbamoyl-ethyl}-amide;

(S)-1-(3-Fluoro-benzenesulfonyl)-piperidine-2-carboxylic acid {(S)-1-((S)-2-methoxy-1-methyl-ethylcarbamoyl)-2-[4-(3-methoxy-propoxy)-phenyl]-ethyl}-amide; and (S)-1-(3-Hydroxy-benzenesulfonyl)-piperidine-2-carboxylic acid [(S)-2-(1H-indol-3-yl)-1-(naphthalen-2-ylcarbamoyl)-ethyl]-amide.

Included in the present invention as an additional aspect of the invention is a pharmaceutical composition, comprising a compound, including enantiomers, stereoisomers, rotamers and tautomers of said compound and pharmaceutically acceptable salts, solvates or derivatives thereof, having the general structure shown in formula I; wherein:

R is fluoroalkyl of the formula $C_nH_xF_y$ wherein n is an integer from 1 to 6, x is an integer from 0 to 12, y is an integer from 1 to 13 and the sum of x and y is 2n+1, aryl, aryl $C_{1-6}$ alkyl, aryl $C_{2-4}$ alkenyl, wherein aryl is selected from phenyl, biphenyl or naphthyl, heteroaryl or heteroaryl $C_{1-4}$ alkyl, wherein heteroaryl is selected from pyridyl, thiophenyl or benzothiophenyl, and heterocyclyl selected from piperidinyl or piperazinyl, $R_1$ is hydrogen or $C_{1-6}$ alkyl;

$R_2$ is $CONHR_4$, benzimidazol-2-yl, $CR_5R_6OH$, or $CR_7R_8NHR_9$;

$R_3$ is aryl and aryl $C_{1-4}$ alkyl or aryl $C_{2-4}$ alkenyl, wherein aryl is selected from phenyl, biphenyl, naphthyl or bisarylmethyl, heteroaryl or heteroaryl $C_{1-4}$ alkyl, wherein heteroaryl is selected from indolyl or thiophenyl, benzothiophenyl, furanyl, benzofuranyl, 1,3-benzodioxolyl, 1,4-benzodioxanyl or $C_{5-7}$ cycloalkyl $C_1$ alkyl;

X is $NR_{10}$ or $CH_2$;

wherein $R_4$ is selected from the group consisting of hydrogen, $C_{1-10}$ alkyl, $C_{2-10}$ alkenyl, $C_{3-8}$ cycloalkyl, $C_{8-12}$ bicycloalkyl, $C_{10-14}$ tricycloalkyl, $C_{3-8}$ cycloalkyl $C_{1-6}$ alkyl, $C_{8-12}$ bicycloalkyl $C_{1-6}$ alkyl, $C_{8-12}$ bicycloalkylamino-$C_{1-6}$ alkyl, $C_{8-12}$ tricycloalkylamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$ wherein n is an integer from 1 to 20, x is an integer from 0 to 40, y is an integer from 1 to 41 and the sum of x and y is 2n+1, amino $C_{2-20}$ alkyl, mono or dialkylamino $C_{2-20}$ alkyl, mono-, di, or trihydroxy $C_{2-20}$ alkyl, $C_{1-6}$ alkoxy-$C_{2-20}$ alkyl, $C_{1-20}$ thioalkyl, $C_{1-6}$ alkyl-thio-$C_{2-20}$ alkyl, hydroxy-$C_{2-6}$-alkoxy-$C_{2-6}$ alkyl, $C_{1-6}$ alkyl-bis-(hydroxy-$C_{1-6}$ alkyl), aryl, aryl $C_{1-10}$ alkyl, aryl $C_{3-4}$ alkenyl, wherein aryl is selected from phenyl, biphenyl, indanyl or naphthyl, heteroaryl or heteroaryl $C_{1-10}$ alkyl, wherein heteroaryl is selected from pyridyl, thiophenyl, furanyl, benzofuranyl, benzothiophenyl, pyrrolidinyl, indolyl, heterocycloalkyl or heterocycloalkyl $C_{1-10}$ alkyl wherein heterocycloalkyl is selected from tetrahydrofuranyl, tetrahydropyranyl, morpholinyl, piperidinyl, pyrrolidinyl, tetrahydrothiophenyl, piperazinyl, dioxolanyl, sulfolanyl or 1,1-dioxotetrahydrothiopyranyl;

heterobicyclyl of the formula:

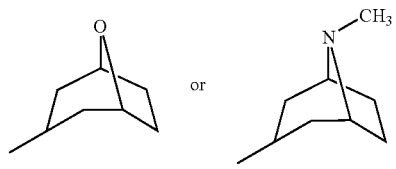

wherein $C_{5-8}$ cycloalkyl, $C_{8-12}$ bicycloalkyl, or heterocyclyl is optionally substituted with one or more substituents selected from the group consisting of $C_{1-10}$ alkyl, $C_{1-10}$ alkoxy, hydroxy, hydroxy $C_{1-10}$ alkoxy, hydroxy $C_{1-10}$ alkyl, $C_{1-10}$ acyloxy, amino, $C_{1-10}$ alkylcarbonylamino, hydroxy $C_{1-20}$ alkylcarbonylamino, amino $C_{2-10}$ alkoxy, mono-$C_{1-6}$-alkylamino-$C_{2-10}$-alkoxy, di-$C_{1-6}$-alkylamino-$C_{2-10}$-alkoxy, mono-$(C_{1-10}$alkyl)amino, di-$(C_{1-10}$ alkyl) amino, amino $C_{1-10}$ alkylcarbonylamino, $C_{1-10}$-alkylaminocarbonyl, hydroxy $C_{1-10}$ alkylaminocarbonyl, amino $C_{2-10}$ alkylaminocarbonyl, mono or dialkylamino $C_{1-10}$ alkylaminocarbonyl, oxo, optionally substituted aryl or optionally substituted heteroaryl, wherein aryl is selected from phenyl, naphthyl or biphenyl and heteroaryl is selected from pyridyl or thiophenyl.

wherein:

the aryl or heteroaryl groups of R are optionally substituted with one or more substituents selected from the group consisting of fluorine, chlorine, bromine, $C_{1-20}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-20}$ alkoxy, $C_{1-20}$ alkenyloxy, $C_{1-10}$-alkoxy-$C_{1-10}$-alkoxy, hydroxy, hydroxy $C_{1-20}$ alkoxy, hydroxy $C_{1-20}$ alkyl, $C_{1-20}$ acyloxy, hydroxy $C_{1-20}$ acyl, nitro, amino, aminosulfonyl, $C_{1-20}$ alkylcarbonylamino, hydroxy $C_{1-20}$ alkylcarbonylamino, amino $C_{2-20}$ alkoxy, amino $C_{1-20}$ alkylcarbonylamino, $C_{1-20}$ alkylaminocarbonyl, hydroxy $C_{1-20}$ alkylaminocarbonyl, amino $C_{1-20}$ alkylaminocarbonyl, mono or dialkylamino $C_{1-20}$ alkylaminocarbonyl, optionally substituted aryl or heteroarylsulfonyl, aminosulfonyl, mono- or di($C_{1-6}$) alkylaminosulfonyl, optionally substituted phenyl or thiophenyl, optionally substituted phenyl or thiophenyl $C_{1-10}$ alkyloxy, and cyano;

wherein the phenyl or thiophenyl substituent on the aryl or heteroaryl group of R is optionally substituted with one or more substituents selected from the group consisting of fluorine, chlorine, bromine, $C_{1-5}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-10}$alkoxy, $C_{1-10}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, hydroxy $C_{1-20}$-alkyloxo, nitro, amino, aminosulfonyl, $C_{1-10}$ alkylcarbonylamino, hydroxy $C_{1-10}$ alkylcarbonylamino, amino $C_{2-10}$ alkoxy, amino $C_{1-10}$ alkylcarbonylamino, $C_{1-10}$ alkylaminocarbonyl, hydroxy $C_{1-10}$ alkylaminocarbonyl, amino $C_{1-10}$ alkylaminocarbonyl, mono or dialkylamino $C_{1-10}$ alkylaminocarbonyl, optionally substituted aryl $C_{1-10}$ alkyloxy, and cyano;

wherein:
the aryl or heteroaryl of $R_3$ is optionally substituted with one or more substituents selected from the following: $C_{3-8}$ cycloalkyloxy, $C_{1-10}$ alkoxy, $C_{1-10}$ alkyl, $C_{2-10}$ alkenyl, $C_{3-10}$ alkenyloxy mono-($C_{1-6}$-alkyl)amino-$C_{2-6}$alkyloxy, di-($C_{1-6}$ alkyl)amino-$C_{2-6}$-alkyloxy, amino-$C_{2-6}$alkyloxy, heterocyclyl-$C_{2-6}$alkyloxy, aryl-$C_{2-6}$-alkyloxy, heteroaryl-$C_{2-6}$-alkyloxy, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and the sum of x and y is 2n+1, $C_{1-6}$-alkoxy-$C_{2-6}$-alkoxy, aryl-$C_{1-6}$-alkyloxy, hydroxy, chloro, fluoro, bromo, hydroxy-$C_{1-6}$-alkoxy, hydroxy-$C_{1-10}$ alkyl, $C_{1-6}$ alkyloxo, cyano, amino, 4-aryloxo, di-$C_{1-5}$ alkylphosphityl-$C_{1-5}$ alkyl, $C_{1-6}$ alkyloxoamino, $C_{1-6}$ alkyloxo($C_{1-6}$ alkyl)amino, $C_{1-10}$alkylsulfonyl, arylsulfonyl, carboxy, $C_{1-20}$-carboalkoxy, dialkylamino-$C_{1-10}$alkyl, monoalkylamino-$C_{1-10}$ alkyl, amino-$C_{1-10}$ alkyl;
wherein: the heterocycloalkyl substituent group attached to the alkyloxy group of $R_3$ is selected from the following: pyrrolidinyl, morpholinyl, piperidinyl, and piperazinyl;
wherein: the heteroaryl substituent group attached to the alkyloxy group of $R_3$ is selected from pyridinyl, pyrrolidinyl,
wherein: the aryl of the arylsulfonyl substituent on the aryl of $R_3$ is selected from phenyl, indolyl, thiophenyl, furanyl;
wherein:
the aryl or heteroaryl groups of $R_4$ are optionally substituted with one or more substituents selected from the following: mono- or di-($C_{1-6}$ alkyl)amino, mono- or di($C_{1-6}$)alkylamino-$C_{2-6}$ alkyl, amino-$C_{1-6}$ alkyl, heterocycloalkyl, amino, $C_{1-20}$ alkoxy, chloro, fluoro, bromo, $C_{1-10}$ alkyl, aryl or heteroaryl;
wherein the heterocycloalkyl group attached to the aryl of $R_4$ is selected from the following: morpholinyl, pyrrolidinyl, piperazinyl, piperidinyl;
wherein the heteroaryl group attached to the aryl of $R_4$ is selected from pyridyl, pyrrolyl, furanyl;
$R_5$, $R_6$=independently H, $C_{1-6}$ alkyl;
$R_7$, $R_8$=independently H, $C_{1-6}$ alkyl;
$R_9$=di-($C_{1-5}$ alkyl)amino-$C_{2-4}$ alkyl; mono($C_{1-5}$ alkyl)amino-$C_{2-4}$ alkyl; amino-$C_{2-4}$ alkyl, heterocycloalkyl methyl in which heterocycloalkyl is selected from the group consisting of thiophenyl, furanyl, pyrrolyl, pyridinyl; and
$R_{10}$=H, $C_{1-6}$ alkyl.

It is to be understood that the pharmaceutical composition may comprise a compound wherein the compound is selected from:

(S)-1-(3-Trifluoromethyl-benzenesulfonyl)-piperidine-2-carboxylic acid [(S)-1-(4-dimethylamino-phenylcarbamoyl)-2-(4-methoxy-phenyl)-ethyl]-amide;
(S)-1-(3-Trifluoromethyl-benzenesulfonyl)-piperidine-2-carboxylic acid [(S)-2-(4-acetyl-phenyl)-1-(4-ethoxy-phenylcarbamoyl)-ethyl]-amide;
(S)-1-(3-Trifluoromethyl-benzenesulfonyl)-piperidine-2-carboxylic acid [(S)-1-(4-morpholin-4-yl-phenylcarbamoyl)-2-(4-trifluoromethyl-phenyl)-ethyl]-amide;
(S)-1-(3-Trifluoromethyl-benzenesulfonyl)-piperidine-2-carboxylic acid [(S)-2-(4-methoxy-phenyl)-1-(tetrahydro-pyran-4-ylcarbamoyl)-ethyl]-amide;
(S)-1-(3-Trifluoromethyl-benzenesulfonyl)-piperidine-2-carboxylic acid [(S)-2-(2-methyl-4-methoxy-phenyl)-1-(tetrahydro-pyran-4-ylcarbamoyl)-ethyl]-amide;
(S)-1-(3-Trifluoromethyl-benzenesulfonyl)-piperidine-2-carboxylic acid [(S)-2-(3,4-dimethoxy-phenyl)-1-(tetrahydro-pyran-4-yl-carbamoyl)-ethyl]-amide;
(S)-1-(3-Trifluoromethyl-benzenesulfonyl)-piperidine-2-carboxylic acid [(S)-2-(4-methoxy-phenyl)-1-(4-morpholin-4-yl-phenylcarbamoyl)-ethyl]-amide;
(S)-1-(3-Methoxy-benzenesulfonyl)-piperidine-2-carboxylic acid ((S)1-carbamoyl-2-phenyl-ethyl)-amide;
(S)-1-(3-Hydroxy-benzenesulfonyl)-piperidine-2-carboxylic acid ((S)-1-carbamoyl-2-phenyl-ethyl)-amide;
(S)-1-(3-Propoxy-benzenesulfonyl)-piperidine-2-carboxylic acid ((S)-1-carbamoyl-2-phenyl-ethyl)-amide;
(S)-1-(3-Trifluoromethyl-benzenesulfonyl)-piperidine-2-carboxylic acid [(S)-2-[4-(1-hydroxy-ethyl)-phenyl]-1-(4-morpholin-4-yl-phenylcarbamoyl)-ethyl]-amide;
(S)-1-(3-Trifluoromethyl-benzenesulfonyl)-piperidine-2-carboxylic acid {(S)-1-(4-ethoxy-phenylcarbamoyl)-2-[4-(1-hydroxy-ethyl)-phenyl]-ethyl}-amide;
(S)-1-(3-Methoxy-benzenesulfonyl)-piperidine-2-carboxylic acid [(S)-2-(indol-3-yl)-1-(naphthalen-2-ylcarbamoyl)-ethyl]-amide;
(S)-1-(3-Trifluoromethyl-benzenesulfonyl)-piperidine-2-carboxylic acid {(S)-1-(4-dimethylamino-phenylcarbamoyl)-2-[4-(1-hydroxy-ethyl)-phenyl]-ethyl}-amide;
(S)-1-(3,5-Dichloro-benzenesulfonyl)-piperidine-2-carboxylic acid [(S)-2-(1H-indol-3-yl)-1-methylcarbamoyl-ethyl]-amide;
(S)-1-(3-Trifluoromethyl-benzenesulfonyl)-piperidine-2-carboxylic acid [(S)-2-(4-acetyl-phenyl)-1-(4-morpholin-4-yl-phenylcarbamoyl)-ethyl]-amide;
(S)-1-(3-Fluoro-benzenesulfonyl)-piperidine-2-carboxylic acid [(S)-2-(4-cyclopentyloxy-phenyl)-1-methyl-1-(tetrahydro-pyran-4-ylcarbamoyl)-ethyl]-amide;
(S)-1-(3-Fluoro-benzenesulfonyl)-piperidine-2-carboxylic acid [(S)-2-(4-isopropoxy-phenyl)-1-(2,2,6,6-tetramethyl-piperidin-4-ylcarbamoyl)-ethyl]-amide;
(S)-1-(3-Fluoro-benzenesulfonyl)-(2S)-piperidine-2-carboxylic acid [(S)-2-[4-(3-fluoro-propoxy)-phenyl]-1-(2,2,6,6-tetramethyl-piperidin-4-ylcarbamoyl)-ethyl]-amide;
(S)-1-(3-Fluoro-benzenesulfonyl)-piperidine-2-carboxylic acid [(S)-2-[4-(3-fluoro-propoxy)-phenyl]-1-((S)-2-methoxy-1-methyl-ethylcarbamoyl)-ethyl]-amide;
(S)-1-(3-Trifluoromethyl-benzenesulfonyl)-piperidine-2-carboxylic acid [(S)-2-(4-isopropoxy-phenyl)-1-methylcarbamoyl-ethyl]-amide;
(S)-1-(3-Trifluoromethyl-benzenesulfonyl)-piperidine-2-carboxylic acid [(S)-2-(4-isopropoxy-phenyl)-1-(tetrahydro-pyran-4-ylcarbamoyl)-ethyl]-amide;
(S)-1-(3-Trifluoromethyl-benzenesulfonyl)-piperidine-2-carboxylic acid [(S)-2-(phenyl)-1-(benzimidazol-2-yl)-ethyl]-amide;
(S)-1-(3-Trifluoromethyl-benzenesulfonyl)-piperidine-2-carboxylic acid [(S)-2-(4-(benzyloxy)phenyl)-1-(benzimidazol-2-yl)-ethyl]-amide;
(S)-1-(3-Fluoro-benzenesulfonyl)-piperidine-2-carboxylic acid [(S)-2-(4-methoxy-phenyl)-1-(tetrahydropyran-4-yl-carbamoyl)-ethyl]-amide;
(S)-1-Benzenesulfonyl-piperidine-2-carboxylic acid ((S)-1-amido-2-(2-methylphenyl)-ethyl)-amide;
(S)-1-Benzenesulfonyl-piperidine-2-carboxylic acid ((S)-1-cyclohexylamido-2-(4-methylphenyl)-ethyl)-amide;
(S)-1-Benzenesulfonyl-piperidine-2-carboxylic acid [(S)-2-(4-allyloxy-phenyl)-1-cyclohexylamido-ethyl]-amide;

(S)-1-(3-Trifluoromethyl-benzenesulfonyl)-piperidine-2-carboxylic acid [(S)-2-(4-allyloxy-phenyl)-1-cyclohexylcarbamoyl-ethyl]-amide;

(S)-1-(3-Trifluoromethyl-benzenesulfonyl)-piperidine-2-carboxylic acid ((S)-1-cyclohexylamido-2-(4-methylphenyl)-ethyl)-amide;

(S)-1-((E)-2-Phenyl-ethenesulfonyl)-piperidine-2-carboxylic acid [(S)-1-amido-2-(1H-indol-3-yl)-ethyl]-amide;

(S)-1-(4,5-Dibromo-thiophene-2-sulfonyl)-piperidine-2-carboxylic acid [(S)-1-amido-2-(1H-indol-3-yl)-ethyl]-amide;

(S)-1-Benzenesulfonyl-piperidine-2-carboxylic acid [(S)-1-tert-butylamido-2-(1H-indol-3-yl)-ethyl]-amide;

(S)-1-Benzenesulfonyl-piperidine-2-carboxylic acid [(S)-1-(3-hydroxy-2,2-dimethyl-propylamido)-2-(4-isopropyl-phenyl)-ethyl]-amide;

(S)-1-Benzenesulfonyl-piperidine-2-carboxylic acid methyl-((S)-1-methylamido-2-(phenyl)-ethyl)-amide;

(S)-1-Benzenesulfonyl-piperidine-2-carboxylic acid [(S)-1-(3,3-dimethyl-butylamido)-2-(4-methoxyphenyl)-ethyl]-amide;

(S)-1-Benzenesulfonyl-piperidine-2-carboxylic acid [(S)-1-(2,2-dimethyl-propylamido)-2-(phenyl)-ethyl]-amide;

(4-{(S)-2-[((S)-1-Benzenesulfonyl-piperidine-2-carbonyl)-amino]-2-amido-ethyl}-benzyl)-phosphonic acid diethyl ester;

(S)-1-Benzenesulfonyl-piperidine-2-carboxylic acid [(S)-2-(4-(acetylamino)-phenyl)-1-amido-ethyl]-amide;

(S)-1-Benzenesulfonyl-piperidine-2-carboxylic acid [(S)-1-amido-2-(4-(hydroxymethyl)-phenyl)-ethyl]-amide;

(S)-1-(Naphthalene-2-sulfonyl)-piperidine-2-carboxylic acid [(S)-1-amido-2-(1H-indol-3-yl)-ethyl]-amide;

(S)-1-(3-Trifluoromethyl-benzenesulfonyl)-piperidine-2-carboxylic acid [(S)-1-(cyclohexylmethyl-amido)-2-(4-methylphenyl)ethyl]-amide;

(S)-1-(3-Trifluoromethyl-benzenesulfonyl)-piperidine-2-carboxylic acid [(S)-1-(4-amino-butylamido)-2-(4-methylphenyl)-ethyl]-amide;

(S)-1-Benzenesulfonyl-piperidine-2-carboxylic acid [(S)-1-amido-2-(1H-indol-3-yl)-ethyl]-amide;

(S)-1-Benzenesulfonyl-piperidine-2-carboxylic acid ((S)-1-amido-2-(pyridin-4-yl)-ethyl)-amide;

(S)-1-Benzenesulfonyl-piperidine-2-carboxylic acid ((S)-1-amido-2-cyclohexyl-ethyl)-amide;

(S)-1-Benzenesulfonyl-piperidine-2-carboxylic acid {(S)-2-phenyl-1-[(thiophen-2-ylmethyl)-amido]-ethyl}-amide;

(S)-1-(3-Fluoro-benzenesulfonyl)-piperidine-2-carboxylic acid [(S)-1-(4-dimethylamino-butylcarbamoyl)-2-(4-fluoro-phenyl)-ethyl]-amide;

(S)-1-(3-Fluoro-benzenesulfonyl)-piperidine-2-carboxylic acid [(S)-2-[4-(3-methoxy-propoxy)-phenyl]-1-(tetrahydro-pyran-4-ylcarbamoyl)-ethyl]-amide;

(S)-1-(3-Trifluoromethyl-benzenesulfonyl)-piperidine-2-carboxylic acid {(S)-1-cyclohexylcarbamoyl-2-[4-(2-dimethylamino-ethoxy)-phenyl]-ethyl}-amide;

(S)-1-(3-Trifluoromethyl-benzenesulfonyl)-piperidine-2-carboxylic acid [(S)-2-(4-methoxy-phenyl)-1-(2-piperazin-1-yl-ethylcarbamoyl)-ethyl]-amide;

(S)-1-(3-Trifluoromethyl-benzenesulfonyl)-piperidine-2-carboxylic acid [(S)-1-(2-hydroxy-1,1-dimethyl-ethylcarbamoyl)-2-(4-methoxy-phenyl)-ethyl]-amide;

(S)-1-Benzenesulfonyl-piperidine-2-carboxylic acid ((S)-1-carbamoyl-2-phenyl-ethyl)-amide;

(S)-1-(3-Fluoro-benzenesulfonyl)-piperidine-2-carboxylic acid {(S)-2-[4-(3-methoxy-propoxy)-phenyl]-1-methylcarbamoyl-ethyl}-amide;

(S)-1-(3-Fluoro-benzenesulfonyl)-piperidine-2-carboxylic acid {(S)-1-((S)-2-methoxy-1-methyl-ethylcarbamoyl)-2-[4-(3-methoxy-propoxy)-phenyl]-ethyl}-amide; and (S)-1-(3-Hydroxy-benzenesulfonyl)-piperidine-2-carboxylic acid [(S)-2-(1H-indol-3-yl)-1-(naphthalen-2-ylcarbamoyl)-ethyl]-amide.

The present invention also includes as an additional aspect of the invention a method of treating a disorder involving neurological damage, comprising: administering to a subject in need thereof, an effective amount of a compound, including enantiomers, stereoisomers, rotamers and tautomers of said compound and pharmaceutically acceptable salts, solvates or derivatives thereof, with said compound having the general structure shown in formula I, wherein:

R is fluoroalkyl of the formula $C_nH_xF_y$, wherein n is an integer from 1 to 6, x is an integer from 0 to 12, y is an integer from 1 to 13 and the sum of x and y is 2n+1, aryl, aryl $C_{1-6}$ alkyl, aryl $C_{2-4}$ alkenyl, wherein aryl is selected from phenyl, biphenyl or naphthyl, heteroaryl or heteroaryl $C_{1-4}$ alkyl, wherein heteroaryl is selected from pyridyl, thiophenyl or benzothiophenyl, and heterocyclyl selected from piperidinyl or piperazinyl, $R_1$ is hydrogen or $C_{1-6}$ alkyl;

$R_2$ is $CONHR_4$, benzimidazol-2-yl, $CR_5R_6OH$, or $CR_7R_8NHR_9$;

$R_3$ is aryl and aryl $C_{1-4}$ alkyl or aryl $C_{2-4}$ alkenyl, wherein aryl is selected from phenyl, biphenyl, naphthyl or bisarylmethyl, heteroaryl or heteroaryl $C_{1-4}$ alkyl, wherein heteroaryl is selected from indolyl or thiophenyl, benzothiophenyl, furanyl, benzofuranyl, 1,3-benzodioxolyl, 1,4-benzodioxanyl or $C_{5-7}$ cycloalkyl $C_1$ alkyl;

X is $NR_{10}$ or $CH_2$;

wherein $R_4$ is selected from the group consisting of hydrogen, $C_{1-10}$ alkyl, $C_{2-10}$ alkenyl, $C_{3-8}$ cycloalkyl, $C_{8-12}$ bicycloalkyl, $C_{10-14}$ tricycloalkyl, $C_{3-8}$ cycloalkyl $C_{1-6}$ alkyl, $C_{8-12}$ bicycloalkyl$C_{1-6}$ alkyl, $C_{8-12}$ bicycloalkylamino-$C_{1-6}$ alkyl, $C_{8-12}$ tricycloalkylamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$, wherein n is an integer from 1 to 20, x is an integer from 0 to 40, y is an integer from 1 to 41 and the sum of x and y is 2n+1, amino $C_{2-20}$ alkyl, mono or dialkylamino $C_{2-20}$ alkyl, mono-, di, or trihydroxy $C_{2-20}$ alkyl, $C_{1-6}$ alkoxy-$C_{2-20}$ alkyl, $C_{1-20}$ thioalkyl, $C_{1-6}$ alkyl-thio-$C_{2-20}$ alkyl, hydroxy-$C_{2-6}$-alkoxy-$C_{2-6}$ alkyl, $C_{1-6}$ alkyl-bis-(hydroxy-$C_{1-6}$ alkyl), aryl, aryl $C_{1-10}$ alkyl, aryl $C_{3-4}$ alkenyl, wherein aryl is selected from phenyl, biphenyl, indanyl or naphthyl, heteroaryl or heteroaryl $C_{1-10}$ alkyl, wherein heteroaryl is selected from pyridyl, thiophenyl, furanyl, benzofuranyl, benzothiophenyl, pyrrolidinyl, indolyl, heterocycloalkyl or heterocycloalkyl $C_{1-10}$ alkyl wherein heterocycloalkyl is selected from tetrahydrofuranyl, tetrahydropyranyl, morpholinyl, piperidinyl, pyrrolidinyl, tetrahydrothiophenyl, piperazinyl, dioxolanyl, sulfolanyl or 1,1-dioxotetrahydrothiopyranyl;

heterobicyclyl of the formula:

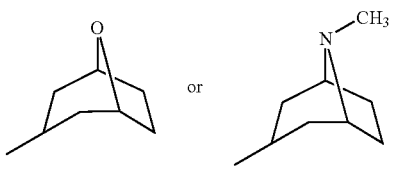

wherein $C_{5-8}$ cycloalkyl, $C_{8-12}$ bicycloalkyl, or heterocyclyl is optionally substituted with one or more substituents selected from the group consisting of $C_{1-10}$alkyl, $C_{1-10}$ alkoxy, hydroxy, hydroxy $C_{1-10}$ alkoxy, hydroxy $C_{1-10}$ alkyl, $C_{1-10}$ acyloxy, amino, $C_{1-10}$ alkylcarbonylamino, hydroxy $C_{1-20}$ alkylcarbonylamino, amino $C_{2-10}$ alkoxy, mono-$C_{1-6}$-alkylamino-$C_{2-10}$-alkoxy, di-$C_{1-6}$-alkylamino-$C_{2-10}$-alkoxy, mono-($C_{1-10}$ alkyl)amino, di-($C_{1-10}$ alkyl) amino, amino $C_{1-10}$ alkylcarbonylamino, $C_{1-10}$ alkylaminocarbonyl, hydroxy $C_{1-10}$ alkylaminocarbonyl, amino $C_{2-10}$ alkylaminocarbonyl, mono or dialkylamino $C_{1-10}$ alkylaminocarbonyl, oxo, optionally substituted aryl or optionally substituted heteroaryl, wherein aryl is selected from phenyl, naphthyl or biphenyl and heteroaryl is selected from pyridyl or thiophenyl.

wherein:
the aryl or heteroaryl groups of R are optionally substituted with one or more substituents selected from the group consisting of fluorine, chlorine, bromine, $C_{1-20}$ alkyl, fluoroalkyl or fluoroalkoxy of the formula $C_nH_xF_y$, or $OC_nH_xF_y$, wherein n is an integer from 1 to 4, x is an integer from 0 to 8, y is an integer from 1 to 9 and the sum of x and y is 2n+1, $C_{1-20}$ alkoxy, $C_{1-20}$ alkenyloxy, $C_{1-10}$-alkoxy-$C_{1-10}$-alkoxy, hydroxy, hydroxy $C_{1-20}$ alkoxy, hydroxy $C_{1-20}$ alkyl, $C_{1-20}$ acyloxy, hydroxy $C_{1-20}$ acyl, nitro, amino, aminosulfonyl, $C_{1-20}$ alkylcarbonylamino, hydroxy $C_{1-20}$ alkylcarbonylamino, amino $C_{2-20}$ alkoxy, amino $C_{1-20}$ alkylcarbonylamino, $C_{1-20}$ alkylaminocarbonyl, hydroxy $C_{1-20}$ alkylaminocarbonyl, amino $C_{1-20}$ alkylaminocarbonyl, mono or dialkylamino $C_{1-20}$ alkylaminocarbonyl, optionally substituted aryl or heteroarylsulfonyl, aminosulfonyl, mono- or di($C_{1-6}$) alkylaminosulfonyl, optionally substituted phenyl or thiophenyl, optionally substituted phenyl or thiophenyl $C_{1-10}$ alkyloxy, and cyano;
  wherein the phenyl or thiophenyl substituent on the aryl or heteroaryl group of R is optionally substituted with one or more substituents selected from the group consisting of fluorine, chlorine, bromine, $C_{1-5}$ alkyl, fluoroalkyl or fluoroalkoxy of the formula $C_nH_xF_y$, or $OC_nH_xF_y$, wherein n is an integer from 1 to 4, x is an integer from 0 to 8, y is an integer from 1 to 9 and the sum of x and y is 2n+1, $C_{1-10}$alkoxy, $C_{1-10}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, hydroxy $C_{1-20}$-alkyloxo, nitro, amino, aminosulfonyl, $C_{1-10}$ alkylcarbonylamino, hydroxy $C_{1-10}$ alkylcarbonylamino, amino $C_{2-10}$ alkoxy, amino $C_{1-10}$ alkylcarbonylamino, $C_{1-10}$ alkylaminocarbonyl, hydroxy $C_{10}$ alkylaminocarbonyl, amino $C_{1-10}$ alkylaminocarbonyl, mono or dialkylamino $C_{1-10}$ alkylaminocarbonyl, optionally substituted aryl $C_{1-10}$ alkyloxy, and cyano;
wherein:
the aryl or heteroaryl of $R_3$ is optionally substituted with one or more substituents selected from the following: $C_{3-8}$ cycloalkyloxy, $C_{1-10}$ alkoxy, $C_{1-10}$ alkyl, $C_{2-10}$ alkenyl, $C_{3-10}$ alkenyloxy mono-($C_{1-6}$-alkyl)amino-$C_{2-6}$alkyloxy, di-($C_{1-6}$ alkyl)amino-$C_{2-6}$-alkyloxy, amino-$C_{2-6}$alkyloxy, heterocyclyl-$C_{2-6}$alkyloxy, aryl-$C_{2-6}$-alkyloxy, heteroaryl-$C_{2-6}$-alkyloxy, fluoroalkyl or fluoroalkoxy of the formula $C_nH_xF_y$, or $OC_{n-}H_xF_y$, wherein n is an integer from 1 to 4, x is an integer from 0 to 8, y is an integer from 1 to 9 and the sum of x and y is 2n+1, $C_{1-6}$-alkoxy-$C_{2-6}$-alkyloxy, aryl-$C_{1-6}$-alkyloxy, hydroxy, chloro, fluoro, bromo, hydroxy-$C_{1-6}$-alkoxy, hydroxy-$C_{1-10}$ alkyl, $C_{1-6}$ alkyloxo, cyano, amino, 4-aryloxo, di-$C_{1-5}$ alkylphosphityl-$C_{1-5}$ alkyl, $C_{1-6}$ alkyloxoamino, $C_{1-6}$ alkyloxo($C_{1-6}$ alkyl)amino, $C_{1-10}$alkylsulfonyl, arylsulfonyl, carboxy, $C_{1-20}$ carboalkoxy, dialkylamino-$C_{1-10}$ alkyl, monoalkylamino-$C_{1-10}$ alkyl, amino-$C_{1-10}$ alkyl;

wherein: the heterocycloalkyl substituent group attached to the alkyloxy group of $R_3$ is selected from the following: pyrrolidinyl, morpholinyl, piperidinyl, and piperazinyl;
wherein: the heteroaryl substituent group attached to the alkyloxy group of $R_3$ is selected from pyridinyl, pyrrolidinyl,
  wherein: the aryl of the arylsulfonyl substituent on the aryl of $R_3$ is selected from phenyl, indolyl, thiophenyl, furanyl;
wherein:
the aryl or heteroaryl groups of $R_4$ are optionally substituted with one or more substituents selected from the following: mono- or di-($C_{1-6}$ alkyl)amino, mono- or di($C_{1-6}$)alkylamino-$C_{2-6}$ alkyl, amino-$C_{1-6}$ alkyl, heterocycloalkyl, amino, $C_{1-20}$ alkoxy, chloro, fluoro, bromo, $C_{1-10}$ alkyl, aryl or heteroaryl;
wherein the heterocycloalkyl group attached to the aryl of $R_4$ is selected from the following: morpholinyl, pyrrolidinyl, piperazinyl, piperidinyl;
wherein the heteroaryl group attached to the aryl of $R_4$ is selected from pyridyl, pyrrolyl, furanyl;
$R_5$, $R_6$=independently H, $C_{1-6}$ alkyl;
$R_7$, $R_8$=independently H, $C_{1-6}$ alkyl;
$R_9$=di-($C_{1-5}$ alkyl)amino-$C_{2-4}$ alkyl; mono($C_{1-5}$ alkyl) amino-$C_{2-4}$ alkyl; amino-$C_{2-4}$ alkyl, heterocycloalkyl methyl in which heterocycloalkyl is selected from the group consisting of thiophenyl, furanyl, pyrrolyl, pyridinyl; and
$R_{10}$=H, $C_{1-6}$ alkyl.

And preferred methods of treating a disorder involving neurological damage include the method wherein the disorder is Parkinson's disease, the method wherein the disorder is multiple sclerosis, the method wherein the disorder is Alzheimer's disease, the method wherein the disorder is stroke, and the method wherein the disorder is spinal cord injury.

Furthermore, a more preferred method for treating a neurological disorder, as described hereinabove includes the method wherein:
R is aryl, aryl $C_{1-6}$ alkyl, aryl $C_{2-4}$ alkenyl, wherein aryl is selected from phenyl, biphenyl or naphthyl, heteroaryl or heteroaryl $C_{1-4}$ alkyl, wherein heteroaryl is selected from pyridyl, thiophenyl or benzothiophenyl, and heterocyclyl selected from piperidinyl or piperazinyl,
$R_1$ is hydrogen or methyl
$R_2$ is CONHR$_4$, benzimidazol-2-yl, CR$_5$R$_6$OH, or CR$_7$R$_8$NHR$_9$;
$R_3$ is phenyl and aryl $C_{1-4}$ alkyl or aryl $C_{2-4}$ alkenyl, wherein aryl is selected from phenyl, biphenyl, naphthyl or bisarylmethyl, heteroaryl or heteroaryl $C_{1-4}$ alkyl, wherein heteroaryl is selected from indolyl or thiophenyl.
X is NR$_{10}$ or CH$_2$;
  wherein $R_4$ is selected from the group consisting of hydrogen, $C_{1-10}$ alkyl, $C_{2-10}$ alkenyl, $C_{3-8}$ cycloalkyl, $C_{8-12}$ bicycloalkyl, $C_{10-14}$ tricycloalkyl, $C_{3-8}$ cycloalkyl-$C_{1-6}$ alkyl, $C_{8-12}$ bicycloalkyl$C_{1-6}$ alkyl, $C_{8-12}$ bicycloalkylamino-$C_{1-6}$ alkyl, $C_{8-2}$ tricycloalkylamino-$C_{1-6}$ alkyl, $C_{3-8}$ cycloalkenyl, $C_{3-8}$ cycloalkenyl $C_{1-6}$ alkyl, fluoroalkyl of the formula $C_nH_xF_y$ wherein n is an integer from 1 to 10, x is an integer from 0 to 20, y is an integer from 1 to 21 and the sum of x and y is 2n+1, amino $C_{2-10}$ alkyl, mono or dialkylamino $C_{2-10}$ alkyl, mono-, di, or trihydroxy $C_{2-10}$ alkyl, $C_{1-6}$-alkoxy-$C_{2-10}$ alkyl, $C_{1-10}$ thioalkyl, $C_{1-6}$alkyl-thio-$C_{2-10}$alkyl, hydroxy-$C_{2-6}$-alkoxy-$C_{2-6}$ alkyl, $C_{1-6}$alkyl-bis-(hydroxy-$C_{1-6}$alkyl), aryl, aryl $C_{1-6}$ alkyl, aryl $C_{3-4}$ alkenyl, wherein aryl is selected from phenyl, biphenyl, indanyl or naphthyl, heteroaryl or heteroaryl $C_{1-10}$ alkyl, wherein heteroaryl is selected from pyridyl, thiophenyl, furanyl, benzofuranyl, benzothiophenyl, pyrrolidinyl, indolyl, heterocycloalkyl or heterocycloalkyl $C_{1-10}$ alkyl wherein heterocycloalkyl is selected from tetrahydrofuranyl, tetrahydropyranyl, morpholinyl, piperidinyl, pyrrolidinyl, piperazinyl, dioxolanyl, sulfolanyl or 1,1-dioxotetrahydrothiopyranyl;

wherein $C_{5-8}$ cycloalkyl, $C_{8-12}$ bicycloalkyl, or heterocycloalkyl is optionally substituted with one or more substituents selected from the group consisting of $C_{1-6}$ alkyl, $C_{1-6}$ alkoxy, hydroxy, hydroxy $C_{1-6}$ alkoxy, hydroxy $C_{1-6}$ alkyl, amino, $C_{1-6}$ alkylcarbonylamino, hydroxy $C_{1-6}$ alkylcarbonylamino, amino $C_{2-6}$ alkoxy, mono-$C_{1-6}$-alkylamino-$C_{2-6}$-alkoxy, di-$C_{1-6}$-alkylamino-$C_{2-6}$-alkoxy, mono-($C_{1-6}$ alkyl)amino, di-($C_{1-6}$ alkyl)amino, amino $C_{1-6}$ alkylcarbonylamino, $C_{1-6}$ alkylaminocarbonyl, hydroxy $C_{1-6}$ alkylaminocarbonyl, amino $C_{2-6}$ alkylaminocarbonyl, mono or dialkylamino $C_{1-6}$ alkylaminocarbonyl, oxo, optionally substituted aryl or optionally substituted heteroaryl, wherein aryl is selected from phenyl, naphthyl or biphenyl and heteroaryl is selected from pyridyl or thiophenyl;

wherein:

the aryl or heteroaryl groups of R are optionally substituted with one or more substituents selected from the group consisting of fluorine, chlorine, bromine, $C_{1-10}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-10}$ alkoxy, $C_{1-10}$ alkenyloxy, $C_{1-10}$-alkoxy-$C_{1-10}$-alkoxy, hydroxy, hydroxy $C_{1-10}$ alkoxy, hydroxy $C_{1-10}$ alkyl, hydroxy $C_{1-10}$ acyl, nitro, amino, aminosulfonyl, $C_{1-10}$ alkylcarbonylamino, hydroxy $C_{1-10}$ alkylcarbonylamino, amino $C_{2-10}$ alkoxy, amino $C_{1-10}$ alkylcarbonylamino, $C_{1-10}$ alkylaminocarbonyl, hydroxy $C_{1-10}$ alkylaminocarbonyl, amino $C_{1-10}$ alkylaminocarbonyl, mono or dialkylamino $C_{1-10}$ alkylaminocarbonyl, optionally substituted aryl or heteroarylsulfonyl, aminosulfonyl, mono- or di($C_{1-6}$)alkylaminosulfonyl, optionally substituted phenyl or thiophenyl, optionally substituted phenyl or thiophenyl $C_{1-10}$ alkyloxy, and cyano;

wherein the phenyl or thiophenyl substituent on the aryl or heteroaryl group of R is optionally substituted with one or more substituents selected from the group consisting of fluorine, chlorine, bromine, $C_{1-5}$ alkyl, $CF_3$, $OCF_3$, $C_{1-6}$ alkoxy, $C_{1-6}$ alkenyloxy, $C_{1-5}$ alkoxy-$C_{1-5}$ alkoxy, hydroxy, hydroxy $C_{1-10}$ alkoxy, hydroxy $C_{1-10}$ alkyl, nitro, amino, aminosulfonyl, $C_{1-10}$ alkylcarbonylamino, hydroxy $C_{1-6}$ alkylcarbonylamino, amino $C_{2-6}$ alkoxy, amino $C_{1-6}$ alkylcarbonylamino, $C_{1-6}$ alkylaminocarbonyl, hydroxy $C_{1-6}$ alkylaminocarbonyl, amino $C_{1-6}$ alkylaminocarbonyl, mono or dialkylamino $C_{1-6}$ alkylaminocarbonyl, optionally substituted aryl $C_{1-6}$ alkyloxy, and cyano;

wherein:

the aryl or heteroaryl of $R_3$ is optionally substituted with one or more substituents selected from the following: $C_{3-6}$ cycloalkyloxy, $C_{1-6}$ alkoxy, $C_{1-6}$ alkyl, $C_{2-6}$ alkenyl, $C_{3-6}$ alkenyloxy, mono-($C_{1-6}$ alkyl)amino-$C_{2-6}$ alkyloxy, di-($C_{1-6}$ alkyl)amino-$C_{2-6}$ alkyloxy, amino-$C_{2-6}$ alkyloxy, heterocyclyl-$C_{2-6}$ alkyloxy, aryl-$C_{2-6}$ alkyloxy, heteroaryl-$C_{2-6}$ alkyloxy, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, $C_{1-6}$ alkoxy-$C_{2-6}$ alkyloxy, aryl-$C_{1-6}$ alkoxy, hydroxy, chloro, fluoro, bromo, hydroxy-$C_{1-6}$ alkoxy, hydroxy-$C_{1-10}$alkyl, $C_{1-6}$alkyloxo, cyano, amino, 4-aryloxo, $C_{1-6}$alkyloxoamino, $C_{1-6}$ alkyloxo($C_{1-6}$ alkyl)amino, carboxy, dialkylamino-$C_{1-6}$ alkyl, monoalkylamino-$C_{1-6}$ alkyl, amino-$C_{1-6}$ alkyl;

wherein: the heterocyclyl substituent group attached to the alkyloxy group of $R_3$ is selected from the following: pyrrolidinyl, morpholinyl, piperidinyl, and piperazinyl;

wherein: the heteroaryl substituent group attached to the alkyloxy group of $R_3$ is selected from pyridinyl, pyrrolidinyl;

wherein:

the aryl or heteroaryl groups of $R_4$ are optionally substituted with one or more substituents selected from the following: mono- or di-($C_{1-6}$ alkyl)amino, mono- or di($C_{1-6}$)alkylamino-$C_{2-6}$-alkyl, amino-$C_{1-6}$ alkyl, heterocyclyl, amino, $C_{1-10}$ alkoxy, chloro, fluoro, bromo, $C_{1-10}$ alkyl, aryl or heteroaryl;

wherein the heterocyclyl group attached to the aryl of $R_4$ is selected from the following: morpholinyl, pyrrolidinyl, piperazinyl, piperidinyl;

wherein the heteroaryl group attached to the aryl of $R_4$ is selected from, pyridyl, pyrrolyl, furanyl;

$R_5$, $R_6$=H;

$R_7$, $R_8$=H;

$R_9$=di-($C_{1-5}$ alkyl)amino-$C_{2-4}$ alkyl; mono($C_{1-5}$ alkyl)amino-$C_{2-4}$ alkyl; amino-$C_{2-4}$ alkyl, heterocycloalkyl methyl in which heterocycloalkyl is selected from group consisting of thiophenyl, furanyl, pyrrolyl, pyridinyl; and $R_{10}$=H, $CH_3$.

And still more preferred methods of treating a disorder involving neurological damage include the method wherein the disorder is Parkinson's disease, the method wherein the disorder is multiple sclerosis, the method wherein the disorder is Alzheimer's disease, the method wherein the disorder is stroke, and the method wherein the disorder is spinal cord injury.

The synthesis of the compounds of the present invention will be understood by a person having skill in the art of chemical synthesis, by reference to the following synthetic schemes.

SCHEME 1

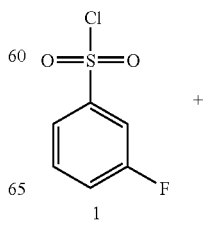

1

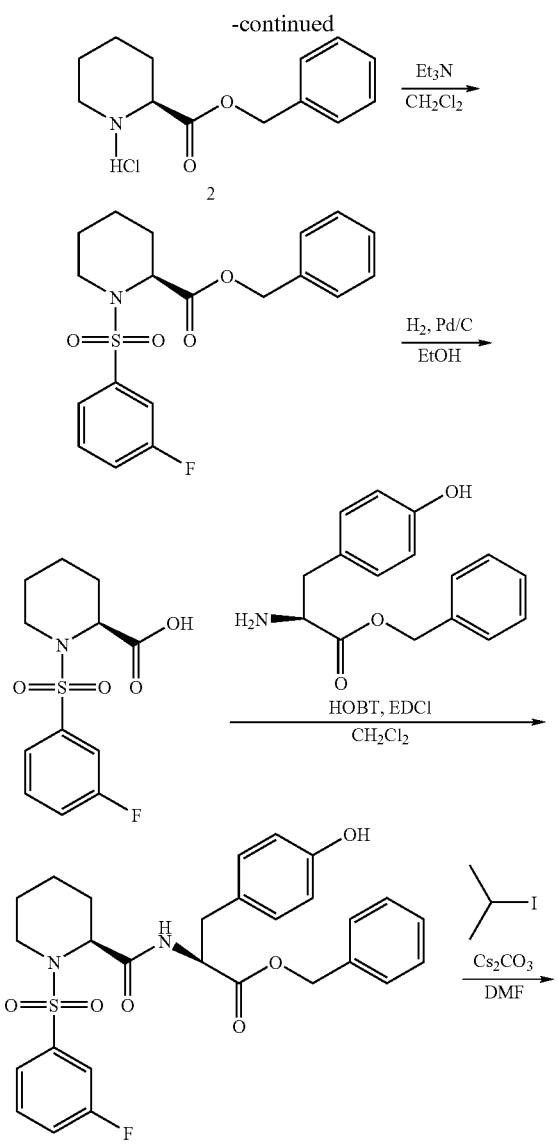
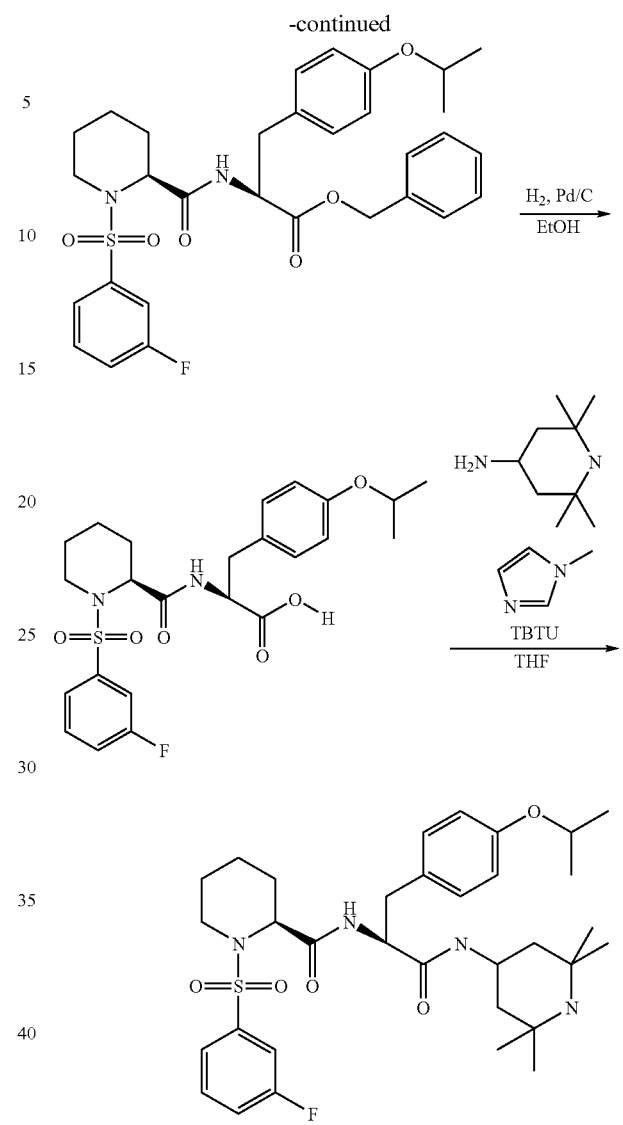
SCHEME 2
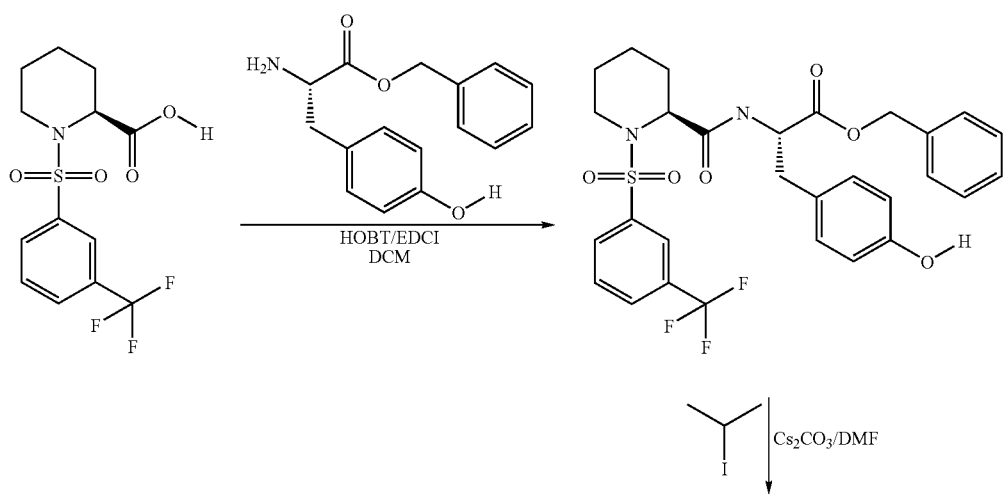

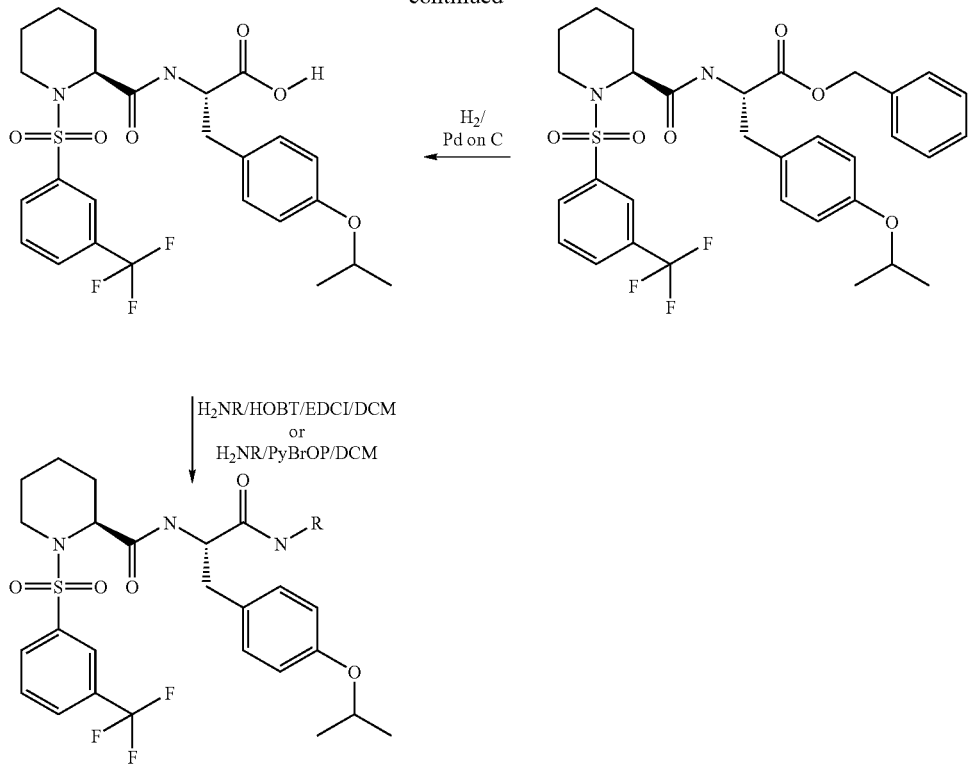
SCHEME 3
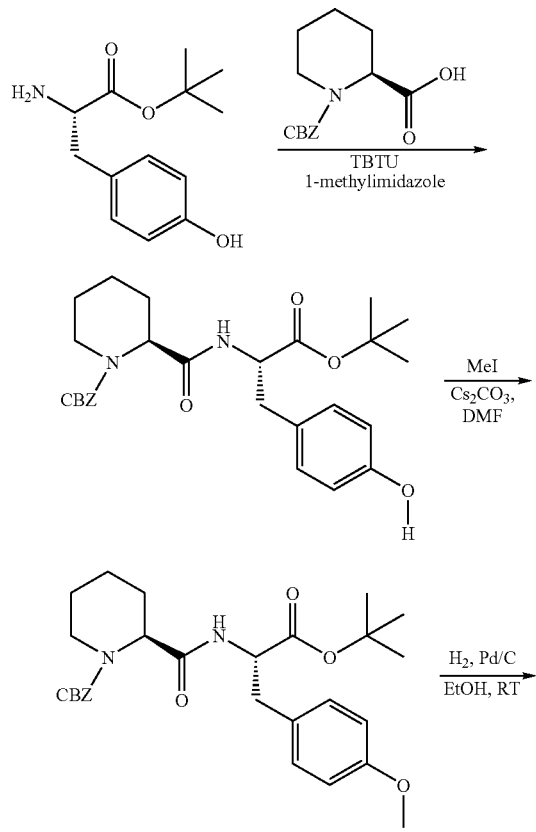
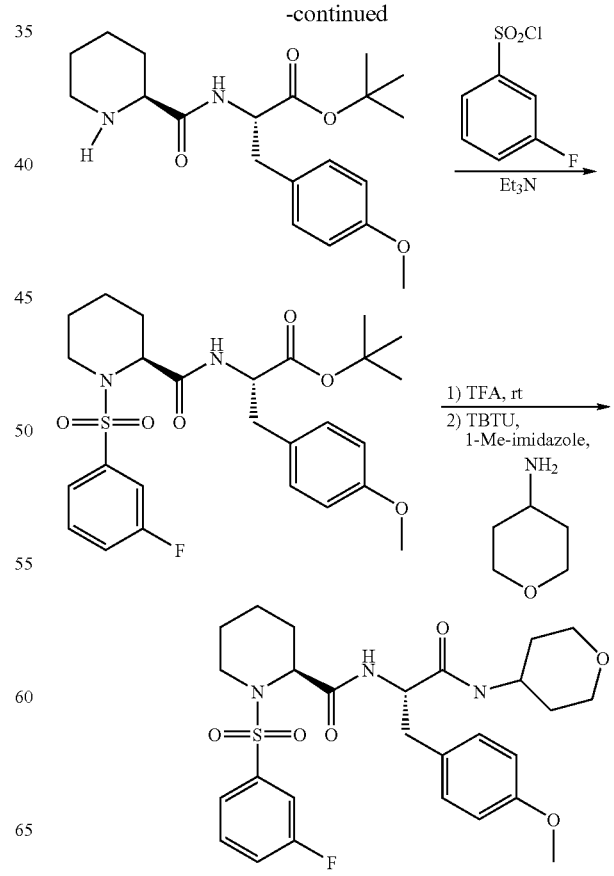

Scheme 4

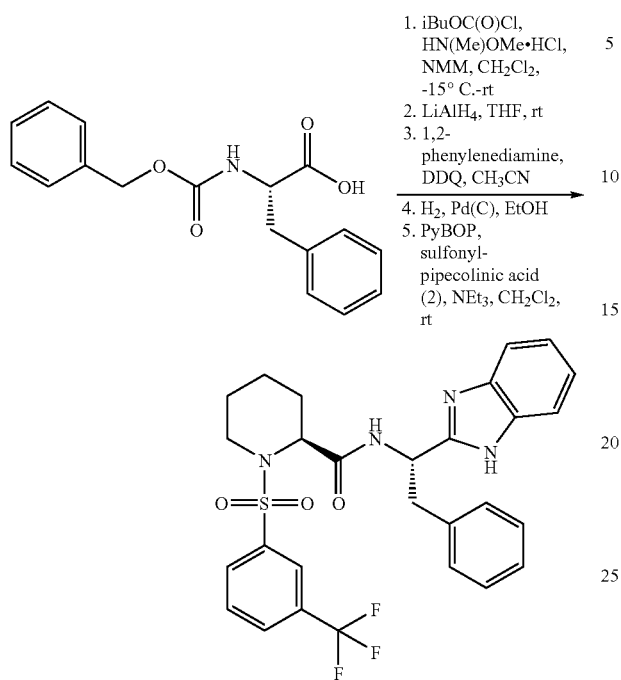

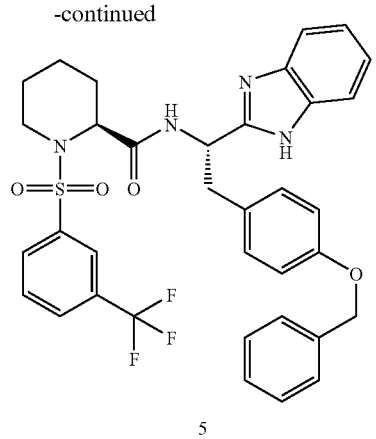

5

Scheme 5

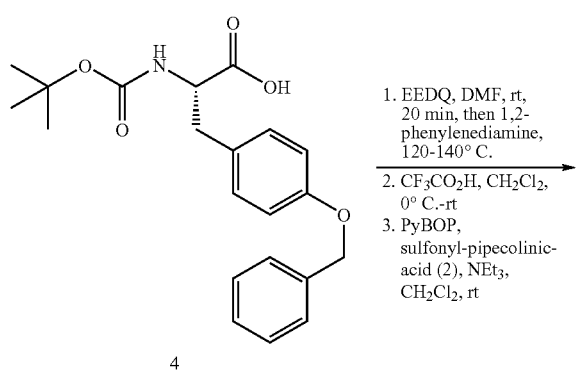

For examples 28 through 38, the following conditions were used for characterizing the reaction products. High Pressure Liquid Chromatography/Mass Spectrometry (LC-MS) conditions for determination of retention times (RT) were as follows: 3 micron Luna® C18 (2) HPLC column (30 mm×4.6 mm) eluting with (i) mixture of 0.05% trifluoroacetic acid in acetonitrile and 0.05% trifluoroacetic acid in water (1:19, v/v) for 2 minutes, (ii) mixture of 0.05% trifluoroacetic acid in acetonitrile and 0.05% trifluoroacetic acid in water (1:19 to 19:1, v/v) gradient elution over 10 minutes, (iii) mixture of 0.05% trifluoroacetic acid in acetonitrile and 0.05% trifluoroacetic acid in water (19:1, v/v) for 2 minutes, (iv) mixture of 0.05% trifluoroacetic acid in acetonitrile and 0.05% trifluoroacetic acid in water (1:19 to 1:19, v/v) gradient elution over 2 minutes; flow rate 2 ml/minute with approximately 200 ml/minute split to the Mass Spectrometer; injection volume 10-40 ml; in line Diode Array (220-450 nm), in line Evaporative Light Scattering (ELS) detection ELS-temperature 50° C., Gain 8-1.8 ml/minute; Source temperature 150° C. HPLC purifications were performed on a 10 micron C18 reverse phase column (4.6 mm×10 cm) eluting with 10-100% acetonitrile and water containing 0.1% trifluoroacetic acid. All NMR spectra were measured in d6-DMSO at 300 MHz unless otherwise indicated.

Compounds Prepared on a Solid Phase

Reaction mixtures in Methods A, B, and C were agitated on a Thermolyne® RotoMix® Type 50800 orbital platform shaker.

Methods A, C, D

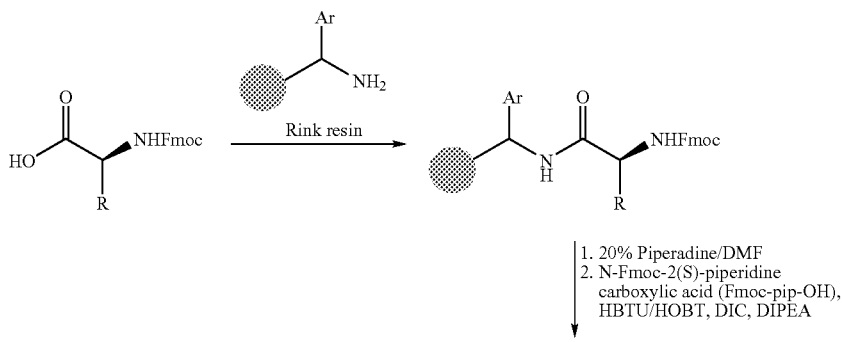

1. 20% Piperadine/DMF
2. N-Fmoc-2(S)-piperidine carboxylic acid (Fmoc-pip-OH), HBTU/HOBT, DIC, DIPEA

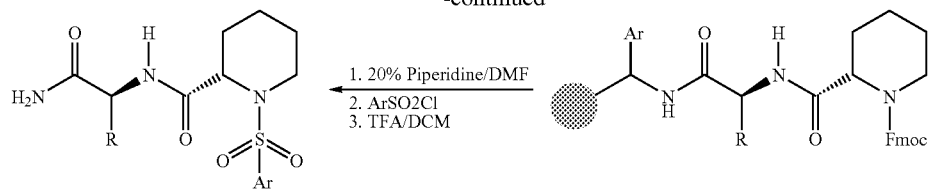
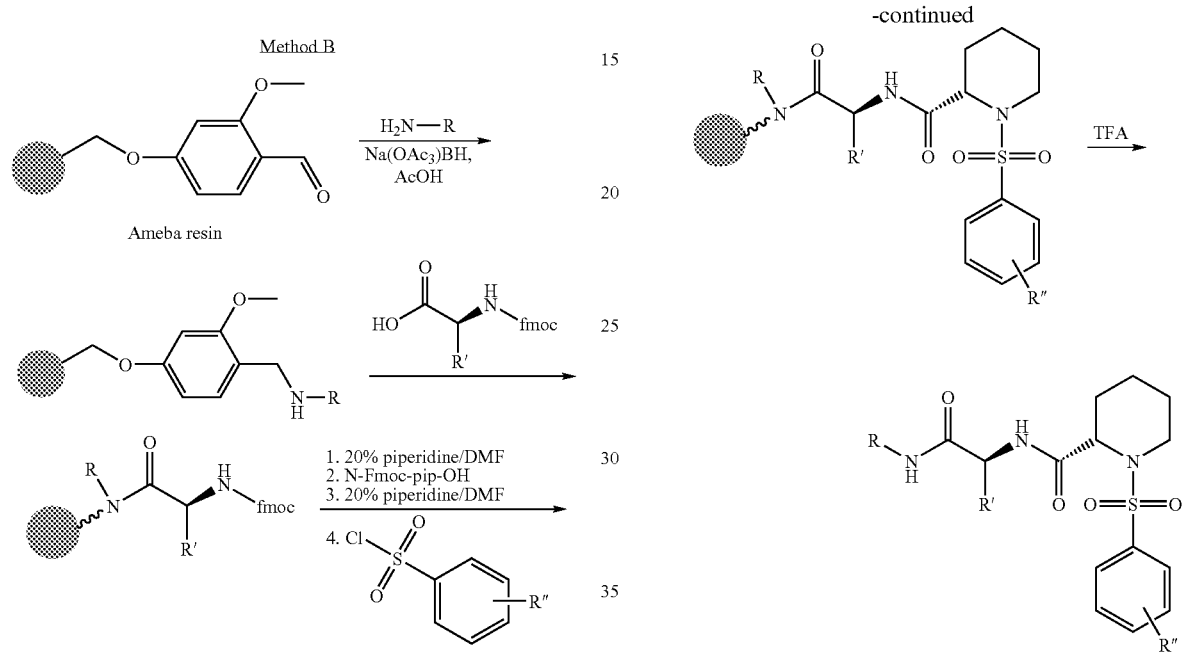
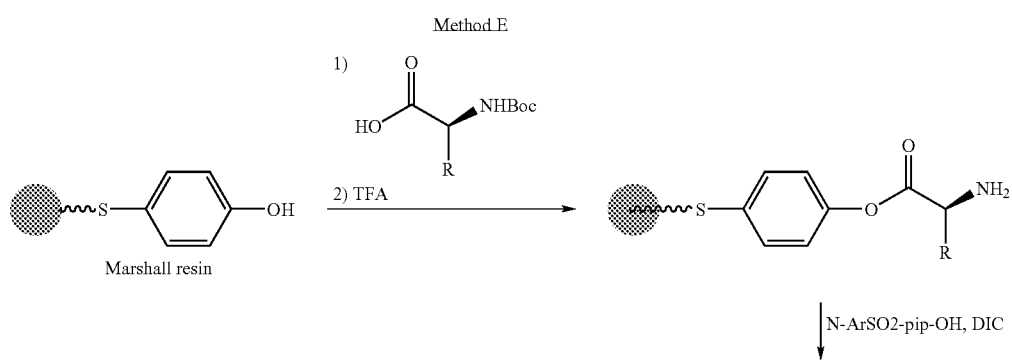
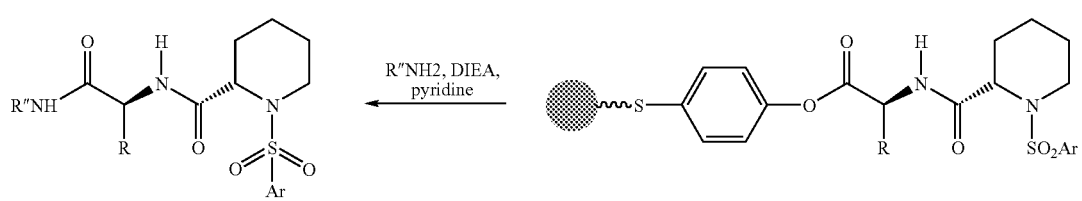

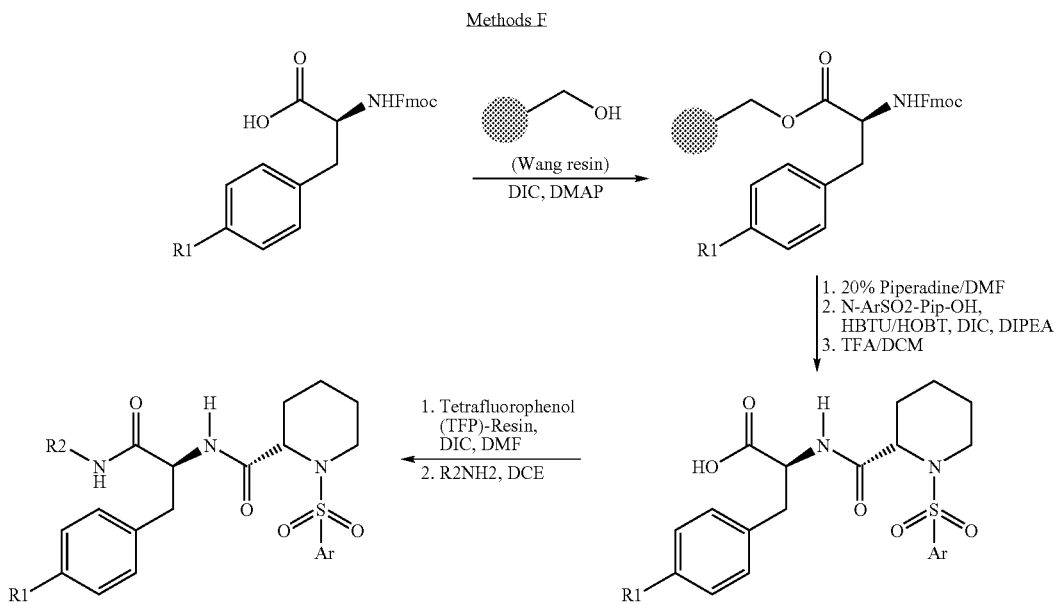

Methods F

The active compounds of the present invention may be administered orally as pharmaceutical composition, for example, with an inert diluent or with an edible carrier. They may be enclosed in gelatin capsules or compressed into tablet. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compounds, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following as pharmaceutically acceptable excipients or ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl, salicylate, or orange flavoring may be added. When the dosage unit is a capsule it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in ampules, disposable syringes or multiple vials made of glass or plastic. The following reagents may be used in the synthetic schemes. DMAP, EDCI, HOAT, HOBT, HOAT, DMSO, PyBOP, HATU, HBTU, DCM, CBZ, PyBOP, and TBTU. DMAP-dimethylaminopropylamine or 4-dimethylaminopyridine. EDCI-1-ethyl-3-[3-(dimethylamino)-propyl]carbodiimide hydrochloride. HOBT-1-hydroxybenzotriazole. DCM-dichloromethane. CBZ-carbobenzyloxy or N-benzyloxycarbonyloxy-. HOAT-1-hydroxy-7-azabenzotriazole. DMSO-dimethylsulfoxide. PyBOP-Benzotriazole-1-yl-oxy-tris-pyrrolidino-phosphonium hexafluorophosphate. TBTU-2-(1H-Benzotriazole-1-yl)-1,1,3,3-tetramethyluronium tetrafluoroborate. HATU-O-(7-azabenzotriazol-1-yl)-1,1,3,3-tetramethyluronium hexafluorophosphate. HBTU-O-(benzotriazol-1-yl)-1,1,3,3-tetramethyluronium hexafluorophosphate. NMR refers to nuclear magnetic resonance. "psi" refers to pounds per square inch.

Measurement of binding affinity to FK506 binding proteins:

A construct containing the FKBP coding sequence (NCBI Locus BC005147, as shown in FIG. 2) is expressed in frame with an eight amino acid tag ((histidine)-6-aspartate-tyrosine) on the N-terminus to yield His6-FKBP12. Purified His6-FKBP12 protein is used for measurement of binding affinity in 96 well microtiter format. All wells contain 3.5 nM [$^3$H]FK506, 50 mM Hepes-NaOH (pH 7.7), 0.05% bovine serum albumin, 90 μg yttrium silicate copper chelate scintillation proximity beads (Amersham®), and 12 ng His6-FKBP12 in 200 μl final volume. Total and non-specific binding is defined as that observed in the absence and presence of 1 μM unlabeled FK506. Compounds of the present invention were evaluated for FKBP target affinity by including various concentrations of the unlabeled test compounds in the incubation mixture. In cases where solvents such as DMSO were used for solubilizing the drug, a comparable concentration of the solvent was included in all wells. The reaction was initiated by adding the His6-FKBP12, then the plates were sealed and placed on a laboratory shaker for 1 hour at room temperature. Bound radioactivity was determined using a plate-based scintillation counter (TopCount®, Packard®). Inhibition constants ($IC_{50}$ values) were obtained using non-linear regression analysis and converted to Ki values using the Cheng-Prusoff correction procedure.

The binding of the compounds of the present invention to FKBP12 is exemplified by the Ki values of the following Table 1.

TABLE 1

| Compound | FKBP $K_i$ nM |
|---|---|
| 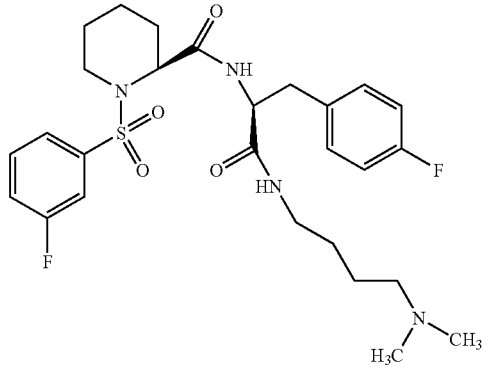 | 19.8 |
| 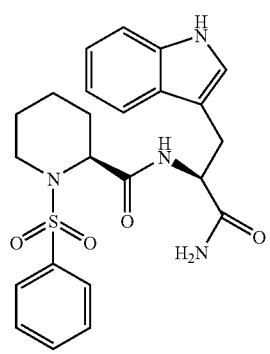 | 191 |
| 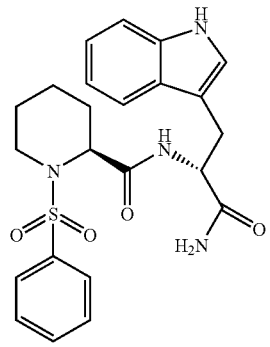 | 26,400 |

TABLE 1-continued

| Compound | FKBP K$_i$ nM |
|---|---|
| (structure) | >100,000 |
| (structure) | 3870 |
| (structure) | 42.3 |
| (structure) | 2.16 |

TABLE 1-continued

| Compound | FKBP K$_i$ nM |
|---|---|
| (structure) | 4.72 |
| (structure) | 3.62 |
| (structure) | 9.13 |
| (structure) | 517 |

TABLE 1-continued

| Compound | FKBP K$_i$ nM |
|---|---|
| (structure) | 3.84 |
| (structure) | 7.25 |
| (structure) | 2.16 |
| (structure) | 2.91 |

TABLE 1-continued

| Compound | FKBP K$_i$ nM |
|---|---|
| (structure) | 4.54 |
| (structure) | 1.55 |
| (structure) | 2.54 |
| (structure) | 11.3 |

TABLE 1-continued
| Compound | FKBP K$_i$ nM |
|---|---|
| 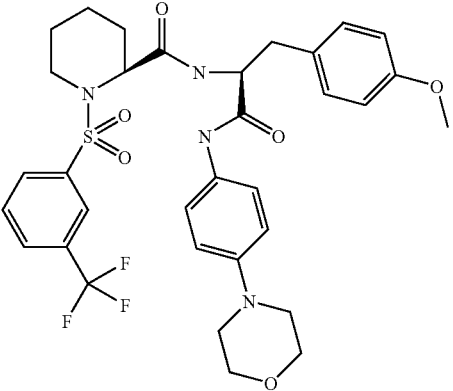 | 0.24 |
| 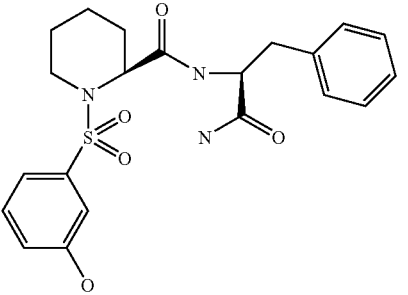 | 556 |
| 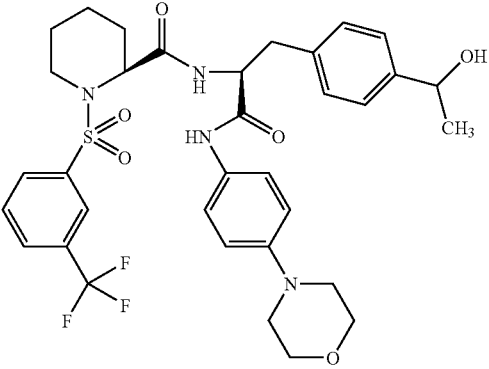 | 2.59 |
| 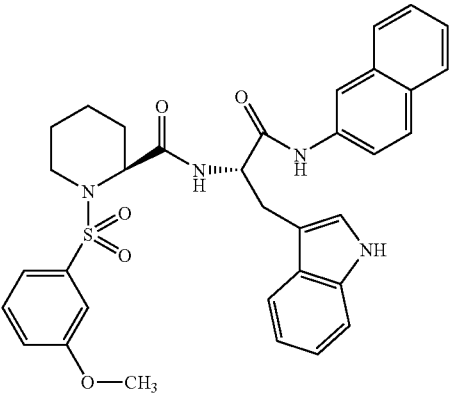 | 27.1 |

TABLE 1-continued

| Compound | FKBP K$_i$ nM |
|---|---|
| [structure] | 25.7 |
| [structure] | 22.2 |
| [structure] | 88.1 |
| [structure] | 5.08 |

TABLE 1-continued

| Compound | FKBP K$_i$ nM |
|---|---|
| (structure) | 331 |
| (structure) | 5.47 |
| (structure) | 18.1 |
| (structure) | 8.47 |

TABLE 1-continued
| Compound | FKBP K$_i$ nM |
|---|---|
| 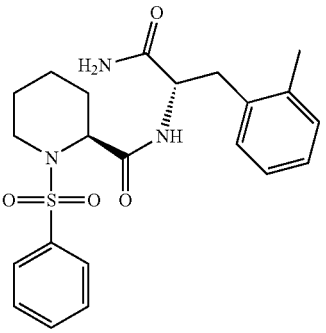 | 456 |
| 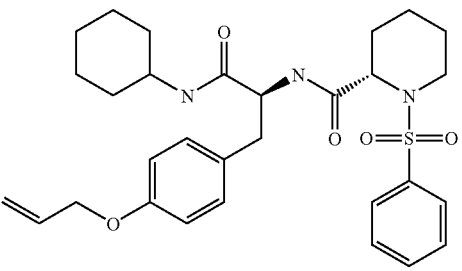 | 12.8 |
| 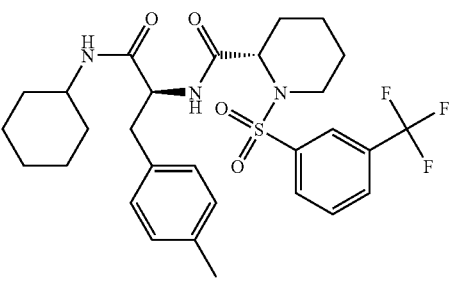 | 30.1 |
| 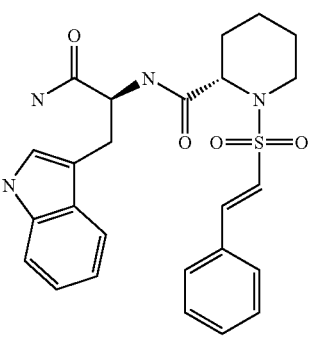 | 842 |

TABLE 1-continued
| Compound | FKBP K$_i$ nM |
|---|---|
| 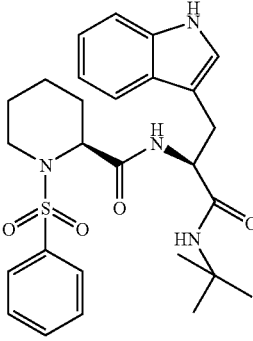 | 151 |
| 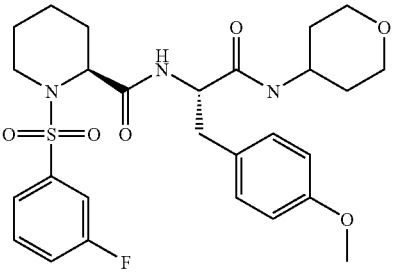 | 281 |
| 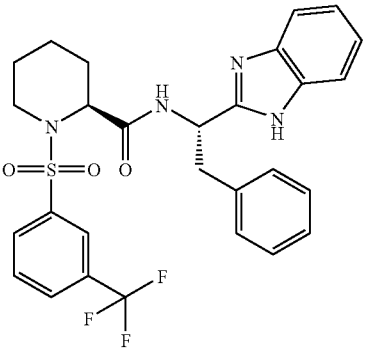 | 97.1 |
| 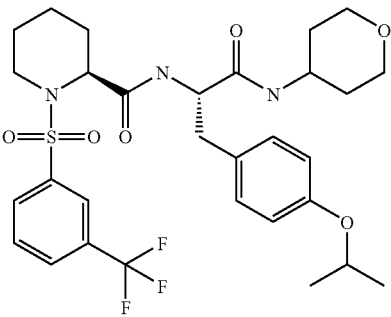 | 2.70 |

TABLE 1-continued

| Compound | FKBP K$_i$ nM |
|---|---|
| (structure) | 79.0 |
| (structure) | 1.91 |
| (structure) | 4.93 |
| (structure) | 40.2 |

Measurement of Activity on FKBP-Mediated Cellular Function:

Background: FK506 and rapamycine are believed to affect cellular function by binding to cytosolic FKBP12. The ligand-bound FKBP12 complexes display specific, high affinity interactions with other protein partners, forming a ternary ligand-protein-protein complex. Although both FK506 and rapamycine each bind to FKBP12, they facilitate distinct protein-protein interactions and modulate different intracellular signal transduction pathways. We have exploited this phenomenon to create an assay for measuring the activity of novel substances that bind to FK506 binding proteins. Compounds are assessed in the presence or absence of FK506 for their effects on reporter gene activation. Such changes are indicative of the compounds entering the cell, interacting with the FKBP12 target, and altering intracellular signaling.

The human IFNγ promoter (see FIG. 1) was cloned into the expression vector pGL3NEO (SstI/Hind III) to give IFNγ-FLuc. Jurkat cells were (grown in RPMI 1640, 10% FBS, 1% antibiotic/antimycotic), transfected with the above DNA [as described by Staynov et al.: Staynov, D. Z., Cousins, D. J., and Lee, T. K. (1995), Proc. Natl. Acad. Sci. USA 92:3606-3610)] and selected against 800 μg/ml of G418 (Geneticin). Monoclonal lines were derived from the stable transfected polyclonal population and used for the assay. The monoclonal cell lines were maintained in culture using the above-described medium in the presence of 400 μg/ml G418.

Jurkat cells containing IFNγ-Luc (monoclonal lines) were resuspended in 1% fetal bovine serum (FBS) containing RPMI Medium 1640 and dispensed into 96-well plates (40,000 cells/well). The plates were then incubated for 3 hours at 37° C. in an atmosphere of 5% $CO_2$. In order to assess intrinsic effects of compounds on FKBP12-mediated signaling, various concentrations of the test compounds (or vehicle) were added to the cells. Then cells were stimulated with 10 ng/ml of phorbol 12-myristate 13-acetate (PMA) and 1.0 μM calcium ionophore (A23187) in a final volume of 100 μl. In other cases, the ability of compounds to inhibit the effects of FK506 was monitored. In this paradigm, fixed concentrations of the test compound (or vehicle) were added to the cell suspension and incubated for 45 minutes at 37° C. in the cell culture incubator. The plates were then removed from the incubator and various concentrations of FK506 (typically $10^{-12}$ M to $10^{-7}$ M final concentration) were added to the respective wells. Cells were then challenged with PMA/A23187 as described above and returned to the cell culture incubator.

After an overnight incubation, the plates were removed from the incubator and the response was terminated by addition of 50 μl of lysis buffer (25 mM Tris phosphate, pH 7.8, 2 mM EDTA, 100 ml/L Glycerol, 1% Triton-X100 (v/v)). The cells were incubated 15 minutes at room temperature, and mixed by repeated up and down pipetting to ensure complete lysis. Then 75 μl of the cell lysate was transferred to Opti-Plate™ white bottomed plates and assayed for luciferase activity by adding 75 μl of a substrate/cofactor mixture (containing: 0.4 mM Luciferin, 0.5 mM ATP, 2.7 mM Coenzyme A, 32.5 mM DTT in 2× Assay buffer: 40 mM Tricine, 2 mM $(MgCO_3)_4$ $Mg(OH)_2 \times 5H_2O$, 10 mM $MgSO_4$, 0.2 mM EDTA). The plates were sealed using an adhesive film and luminescence was quantified in a Packard TopCount-NXT™ plate reader.

The intrinsic activity of the test compounds was determined from their ability to inhibit PMA/A23187-mediated increases in reporter activity. Concentrations producing half-maximal inhibition ($EC_{50}$) were derived using non-linear regression analysis. For reference, the $EC_{50}$ of FK506 in this paradigm was 0.7 nM. In other cases, the activity of the test compounds to prevent the action of FK506 was assessed. This was quantitated as the ratio of the $EC_{50}$ of FK506 observed in the presence of 10M test compound divided by the respective $EC_{50}$ value measured in the absence of the test compound. For reference, rapamycine (1 μM) produces a ratio value of 15-30. Compounds interacting with cellular FKBP12 demonstrate either direct inhibition of PMA/A23187-mediated effects with $EC_{50}$ values less than 10 μM or when administered at 1 μM produce statistically significant increases in the $EC_{50}$ of FK506. See: Staynov, D. Z., Cousins, D. J., and Lee, T. K. (1995), Proc. Natl. Acad. Sci. USA 92:3606-3620.

Measurement of Activity on FKBP-mediated cellular function in Jurkat cells of the compounds of the present invention is exemplified by the "Jurkat Shift" values of the following Table 2. The Jurkat Shift values represent the ratio of the $EC_{50}$ of FK506 observed in the presence of 10M test compound divided by the respective $EC_{50}$ value in the absence of test compound.

TABLE 2

| Compound | Jurkat Shift |
|---|---|
| 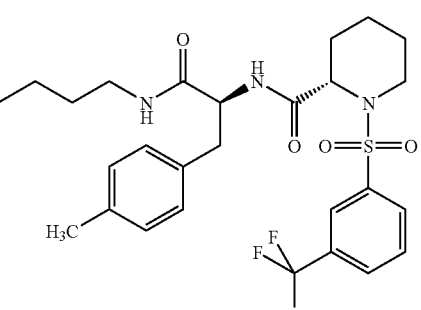 | 4.5 |
| 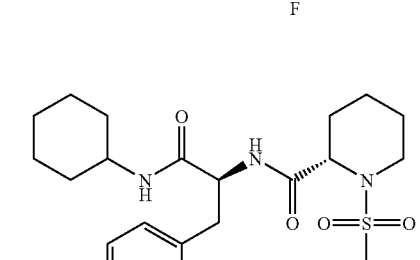 | 13.4 |

TABLE 2-continued

| Compound | Jurkat Shift |
|---|---|
| | 10.4 |
| | 69.5 |
| | 83.1 |
| | 45.7 |

TABLE 2-continued
| Compound | Jurkat Shift |
|---|---|
| 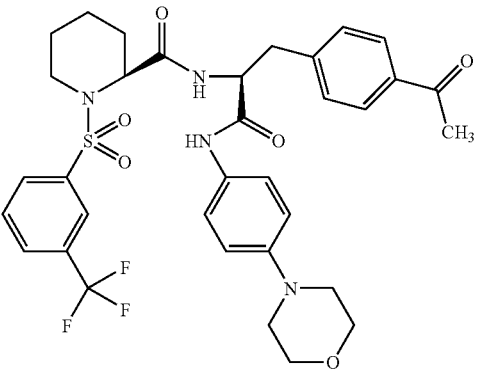 | 12.3 |
| 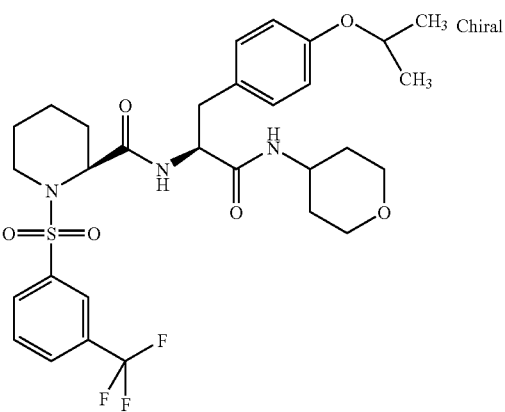 | 7.5 |
| 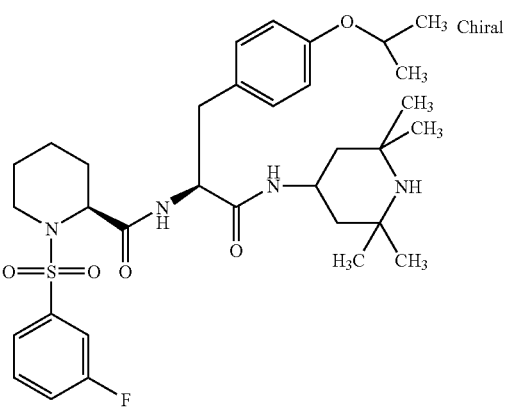 | 69.4 |
| 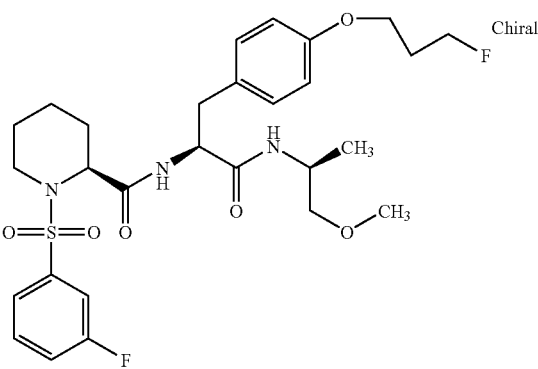 | 7.1 |

TABLE 2-continued
| Compound | Jurkat Shift |
|---|---|
| 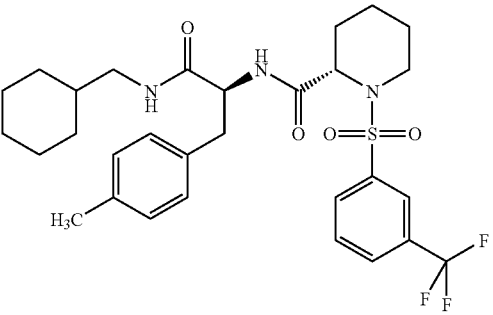 | 2.8 |
| 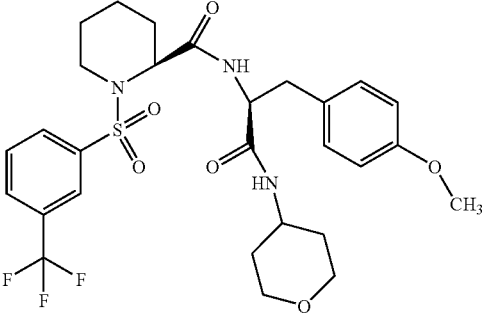 | 14.4 |
| 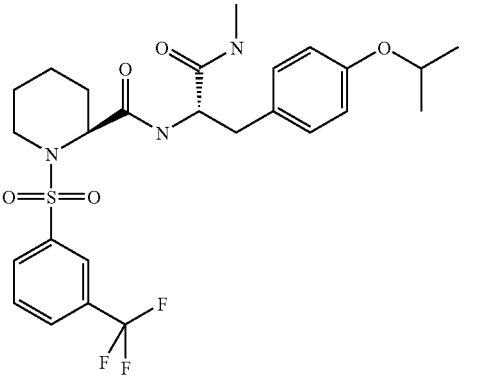 | 3.4 |
| 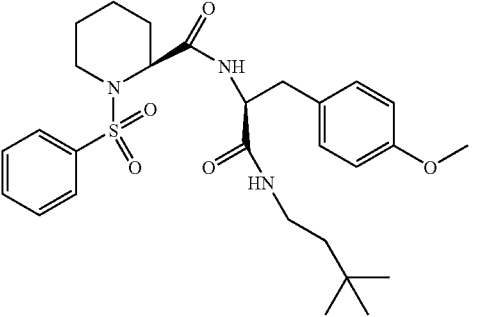 | 6.5 |

TABLE 2-continued

| Compound | Jurkat Shift |
|---|---|
| 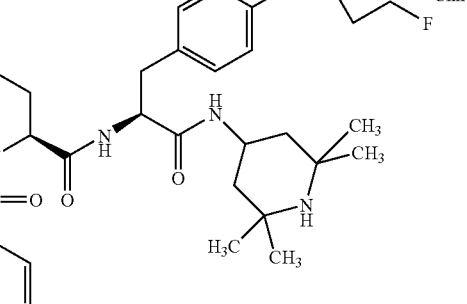 | 34.6 |
| 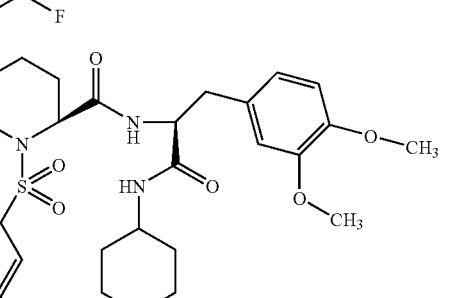 | 31.4 |

Neurite Outgrowth Assay:

PC12 cells, obtained from the American Type Culture Collection, were grown in RPMI-1640 medium supplemented with 10% heat-inactivated horse serum (HS) and 5% FBS. Cells were seeded in collagen 4-coated 96 well plates in low serum (0.5% HS, 0.25% FBS) media at a density of 2,000 cells/well. The cells were then primed with 1 µg/ml of NGF for 3 days. On the fourth day, the culture media was replaced with one containing 50 ng/ml of NGF and, where indicated, test compounds. The cells were then incubated for another 4 days following which they were fixed and immunostained with a primary antibody specific for neuronal cells bodies and processes, followed by Alexa Fluor 488-coupled secondary antibody, and the nuclear counterstain Hoechst® Dye (Hit-Kit® Cat#K07-0001-1, Cellomics®). Neurite outgrowth in the stained specimens were quantitated using a computer-controlled, microscope-based imaging system (ArrayScan II®, Cellomics®). Compounds of the present invention were found to significantly increase both the fraction of total cells bearing neurites and the average neurite length.

Measurement of Immunosuppressant Activity in Human T-Cells:

Purified CD4 positive lymphocytes were obtained from human, peripheral blood. Cells were stimulated for 24 hours using anti-CD3 and CD28 monoclonal antibodies cross-linked to protein G. Three days after stimulation, IL-2 production was measured in the culture media supernatant using a commercially available ELISA kit (BD Biosciences). FK506 was employed in all experiments as a positive control. IL-2R expression was measured by flow cytometry using fluorescent-labeled anti-CD25 and anti-CD122 monoclonal antibodies (binding to the alpha and beta chains of the IL-2R, respectively). Cell proliferation was assessed by tritiated-thymidine incorporation measured at 3 and 6 days post-stimulation. Immunosuppressant activity was defined as activity qualitatively similar to that displayed by FK506.

The present invention is further exemplified by, but not limited to the following examples.

EXAMPLES

Example 1

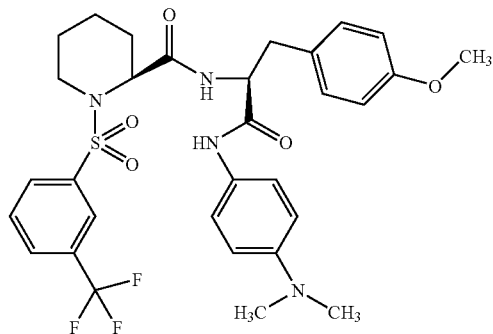

1

(S)-1-(3-Trifluoromethyl-benzenesulfonyl)-piperidine-2-carboxylic acid [(S)-1-(4-dimethylamino-phenylcarbamoyl)-2-(4-methoxy-phenyl)-ethyl]-amide

1a)

(S)-1-(3-Trifluoromethyl-benzenesulfonyl)-piperidine-2-carboxylic acid benzyl ester To 4.0 g (15.64 mmol or millimoles) of (S)-piperidine-2-carboxylic acid benzyl ester hydrochloride and 3.15 g (31.28 mmol) of triethylamine in (200 ml) was added 4.21 g (17.20 mmol) of 3-trifluoromethylbenzenesulfonyl chloride. The mixture was stirred at room temperature for 1 hour. The reaction mixture was then washed with water, brine and dried (sodium sulfate). Chromatography on silica gel, eluting with dichloromethane provided 6.7 g (15.64 mmol) of (S)-1-(3-Trifluoromethyl-benzenesulfonyl)-piperidine-2-carboxylic acid benzyl ester. LCMS (M+H): m/z 428, retention time 3.9 min.

1b)

(S)-1-(3-Trifluoromethyl-benzenesulfonyl)-piperidine-2-carboxylic acid

To 12.20 g (28.85 mmol) of N-3-trifluoromethyl-(S)-piperidine-2-carboxylic acid benzyl ester in 300 ml of 1/1 methanol/ethyl acetate was added 2.0 g of 10% palladium on carbon. The resulting suspension was stirred under 1 atmosphere of hydrogen for 2 hours, after which the catalyst was filtered and the filtrate was concentrated to provided 8.0 g (23.73 mmol) of (S)-1-(3-Trifluoromethyl-benzenesulfonyl)-piperidine-2-carboxylic acid, which was used without further purification. The 300 MHz $^1$H NMR was consistent with the structure. LCMS (M+H): m/z 338, retention time 2.77 min.

1c)

(S)-3-(4-Hydroxy-phenyl)-2-{[(S)-1-(3-trifluoromethyl-benzenesulfonyl)-piperidine-2-carbonyl]-amino}-propionic acid methyl ester To a solution of 0.96 g (2.85 mmol) of compound 1b and 1.26 g (2.85 mmol) of the p-toluenesulfonic acid salt of tyrosine benzyl ester in 20 ml of dichloromethane was added 1.2 g (14.24 mmol) of sodium bicarbonate followed by 0.93 g (6.84 mmol) of HOAT and 1.52 g (8.00 mmol) of EDCI. The mixture was stirred at room temperature for 17 hours after which it was purified by flash chromatography on silica gel eluting with 30-50% ethyl acetate/heptane to provide 1.2 g (20.33 mmol) of (S)-3-(4-hydroxy-phenyl)-2-{[(S)-1-(3-trifluoromethyl-benzenesulfonyl)-piperidine-2-carbonyl]-amino}-propionic acid methyl ester. LCMS (M+H): m/z 591, retention time 3.59 min.

1d)

(S)-3-(4-Methoxy-phenyl)-2-{[(S)-1-(3-trifluoromethyl-benzenesulfonyl)-piperidine-2-carbonyl]-amino}-propionic acid benzyl ester To a solution of 0.4 g (0.68 mmol) benzyl ester (1c) in 4 ml of DMSO was added 1.10 g (3.39 mmol) of cesium carbonate followed by 0.96 g (6.78 mmol) of iodomethane. This mixture was stirred at room temperature overnight. Reaction mixture was then diluted with 20 ml of ethyl acetate, washed with water three times, brine three times. It was purified by chromatography on silica gel, eluting with 50% ethyl acetate/heptane to give 0.41 g (0.68 mmol) of (S)-3-(4-methoxy-phenyl)-2-{[(S)-1-(3-trifluoromethyl-benzenesulfonyl)-piperidine-2-carbonyl]-amino}-propionic acid benzyl ester. LCMS (M+H): m/z 605, retention time 3.79 min.

1e)

(S)-3-(4-Methoxy-phenyl)-2-{[(S)-1-(3-trifluoromethyl-benzenesulfonyl)-piperidine-2-carbonyl]-amino}-propionic acid To 0.41 g (0.68 mmol) of benzyl ester (1d) in 6 ml of 1/1 methanol/ethyl acetate under nitrogen was added 0.082 g of 10% palladium on carbon. The resulting suspension was stirred under 1 atm of hydrogen for 2 hours, after which the suspension was filtered and the filtrate concentrated to provide 0.34 g (0.68 mmol) of (S)-3-(4-methoxy-phenyl)-2-{[(S)-1-(3-trifluoromethyl-benzenesulfonyl)-piperidine-2-carbonyl]-amino}-propionic acid which was used without further purification. The 300 MHz $^1$H NMR was consistent with the structure. LCMS (M+H): m/z 515, retention time 3.37 min.

1f)

(S)-1-(3-Trifluoromethyl-benzenesulfonyl)-piperidine-2-carboxylic acid [(S)-1-(4-dimethylamino-phenylcarbamoyl)-2-(4-methoxy-phenyl)-ethyl]-amide To a solution of 38 mg (0.28 mmol) of 4-dimethylaminoaniline and 72 mg (0.14 mmol) of carboxylic acid (1e) in 3 ml of dichloromethane was added 70 mg (0.82 mmol) of sodium bicarbonate followed by 46 mg (0.34 mmol) of HOAT and 74 mg (0.392 mmol) of EDCI. The mixture was stirred at room temperature for 17 hours after which it was purified by flash chromatography on silica gel, eluting with 30-50% ethyl acetate/heptane. The resulting solid was washed with 30% ethyl acetate/heptane and dried to provide 53 mg (83.8 mmol) of the title compound. $^1$H NMR (400 MHz, CDCl$_3$): 1.13-1.46 (m, 5H); 2.14-2.16 (bd, 1H); 2.60 (t, 1H); 2.91 (s, 6H); 3.06 (dd, 1H); 3.23 (dd, 1H); 3.65-3.68 (bd, 1H); 3.78 (s, 3H); 4.42 (b, 1H); 4.71 (q, 1H); 6.87 (d, 3H); 7.18 (d, 2H); 7.30 (d, 2H); 7.62 (s, 1H); 7.69 (t, 1H); 7.86 (d, 1H); 8.01 (d, 1H). Example 1 exhibits FKBP12 binding with a $K_i$ of 6.11E−10.

Example 2

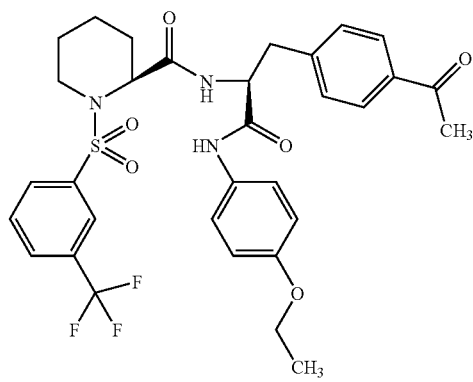

2

(S)-1-(3-Trifluoromethyl-benzenesulfonyl)-piperidine-2-carboxylic acid [(S)-2-(4-acetyl-phenyl)-1-(4-ethoxy-phenylcarbamoyl)-ethyl]-amide The title compound was prepared from carboxylic acid compound 15a and 4-ethoxyaniline employing the procedure used to synthesize compound 15. $^1$H NMR (300 MHz, CDCl$_3$): 1.09-1.42 (m, 8H); 2.04-2.12 (bd, 1H); 2.51-2.54 (m, 1H); 2.59 (s, 3H); 3.22 (dd, 1H); 3.42 (dd, 1H); 3.58-3.62 (bd, 1H); 4.00 (q, 2H); 4.37 (b, 1H); 4.86 (q, 1H); 6.84 (d, 1H); 6.90 (d, 1H); 7.38 (d, 4H); 7.70 (t, 1H); 7.86-7.94 (m, 4H); 8.00 (d, 1H); 8.08 (s, 1H).

Example 3

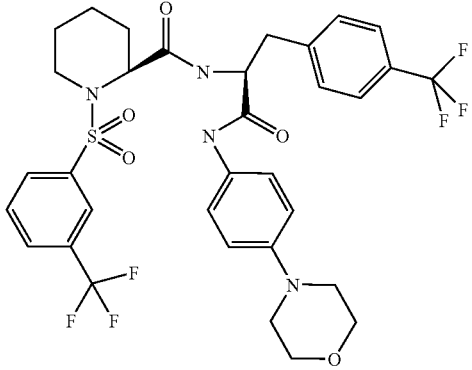

3. (S)-1-(3-Trifluoromethyl-benzenesulfonyl)-piperidine-2-carboxylic acid [(S)-1-(4-morpholin-4-yl-phenylcarbamoyl)-2-(4-trifluoromethyl-phenyl)-ethyl]-amide The title compound was prepared from the corresponding 4-(trifluoromethyl)phenylalanine carboxylic acid derivative and 4-morpholinoaniline as described for step (1f). $^1$H NMR (400 MHz, CDCl$_3$): 0.95-1.45 (m, 5H); 2.16-2.05 (bd, 1H); 2.35 (dd, 1H); 3.02-3.20 (m, 5H); 3.41-3.60 (m, 2H); 3.84-3.87 (m, 4H); 4.36 (b, 1H); 4.80-4.90 (m, 1H); 6.85-6.88 (m, 3H); 7.38-7.43 (m, 4H); 7.60 (d, 2H); 7.70 (t, 1H); 7.88 (d, 1H); 7.95 (s, 1H); 8.01 (d, 1H); 8.08 (s, 1H).

Example 4

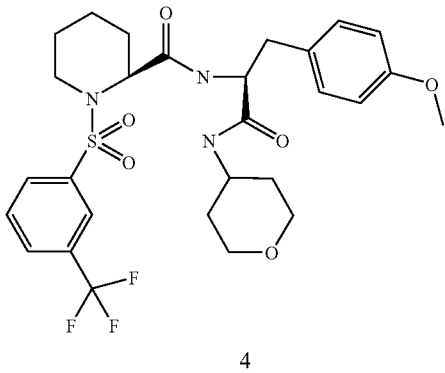

4

(S)-1-(3-Trifluoromethyl-benzenesulfonyl)-piperidine-2-carboxylic acid [(S)-2-(4-methoxy-phenyl)-1-(tetrahydro-pyran-4-ylcarbamoyl)-ethyl]-amide To a solution of 0.094 g (0.94 mmol) of 4-aminotetrahydropyran and 0.48 g (0.94 mmol) of (S)-3-(4-methoxy-phenyl)-2-{[(S)-1-(3-trifluoromethyl-benzenesulfonyl)-piperidine-2-carbonyl]-amino}-propionic acid in 50 ml of dichloromethane was added 0.079 g (0.94 mmol) of sodium bicarbonate followed by 0.128 g (0.94 mmol) of HOAT and 0.179 g (0.94 mmol) of EDCI. The mixture was stirred at room temperature for 17 hours after which it was washed with brine and purified by flash chromatography on silica gel, eluting with 50-100% ethyl acetate/heptane to give 0.50 g (0.83 mmol) of the title compound. $^1$H NMR (300 MHz, CDCl$_3$): 1.00-1.21 (m, 3H); 1.32-1.43 (m, 4H); 1.80 (b, 2H); 2.14 (bd, 1H); 2.69 (t, 1H); 2.99 (dd, 1H); 3.13 (dd, 1H); 3.45 (s, 2H); 3.65 (bd, 1H); 3.78 (s, 3H); 3.87-4.00 (m, 3H); 4.39 (b, 1H); 4.58 (q, 1H); 5.88 (d, 1H); 6.78 (d, 1H); 6.85 (d, 2H); 7.13 (d, 2H); 7.70 (t, 1H); 7.88 (d, 1H); 8.00 (d, 1H); 8.08 (s, 1H).

Example 5

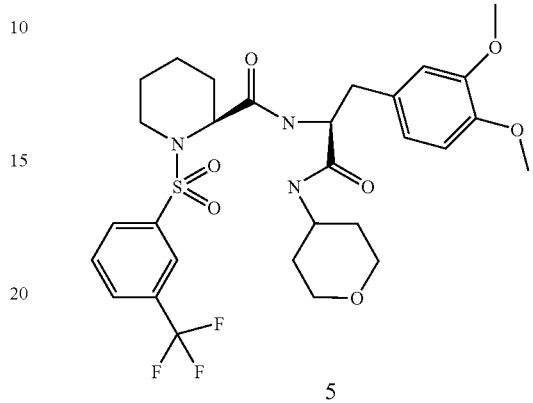

5

(S)-1-(3-Trifluoromethyl-benzenesulfonyl)-piperidine-2-carboxylic acid [(S)-2-(3,4-dimethoxy-phenyl)-1-(tetrahydro-pyran-4-ylcarbamoyl)-ethyl]-amide To a solution of 90 mg (0.29 mmol) of (S)-2-amino-3-(3,4-dimethoxy-phenyl)-(tetrahydropyran-4-yl)-propionamide and 98 mg (0.29 mmol) of (S)-1-(3-trifluoromethyl-benzenesulfonyl)-piperidine-2-carboxylic acid in 2 ml of dichloromethane was added 25 mg (0.29 mmol) of sodium bicarbonate followed by 40 mg (0.29 mmol) of HOAT and 56 mg (0.29 mmol) of EDCI. The mixture was stirred at room temperature for 17 hours after which it was purified by flash chromatography on silica gel, eluting with 50-100% ethyl acetate/heptane to give 0.162 g (0.25 mmol) of the title compound. $^1$H NMR (300 MHz, CDCl$_3$): 1.00-1.40 (m, 7H); 1.84 (b, 2H); 2.12 (bd, 1H); 2.60 (t, 1H); 2.99 (dd, 1H); 3.18 (dd, 1H); 3.45 (t, 2H); 3.61 (bd, 1H); 3.79-4.00 (m, 9H); 4.38 (b, 1H); 4.62 (q, 1H); 5.96 (d, 1H); 6.74-6.83 (m, 4H); 7.70 (t, 1H); 7.87 (d, 1H); 8.00 (d, 1H); 8.07 (s, 1H).

Example 6

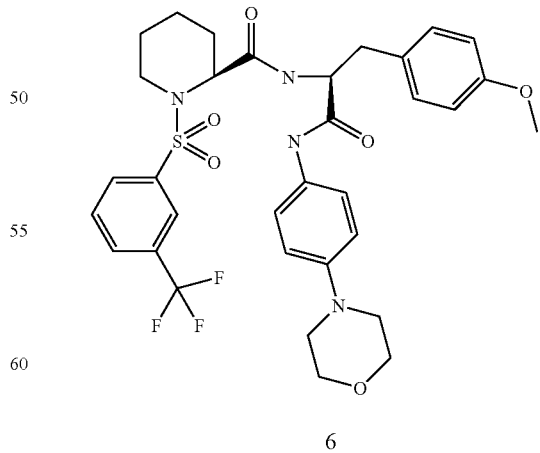

6

(S)-1-(3-Trifluoromethyl-benzenesulfonyl)-piperidine-2-carboxylic acid [(S)-2-(4-methoxy-phenyl)-1-(4-morpholin-4-yl-phenylcarbamoyl)-ethyl]-amide The title compound was prepared from carboxylic acid compound 1e and 4-morpholino aniline according to the method described for the preparation of compound 1. ¹H NMR (300 MHz, CDCl₃): 1.00-1.52 (m, 5H); 2.12-2.14 (bd, 1H); 2.56 (dd, 1H); 3.02-3.13 (m, 5H); 3.25 (dd, 1H); 3.65 (bd, 1H); 3.79 (s, 3H); 3.83-3.86 (m, 4H); 4.40 (b, 1H); 4.73 (q, 1H); 6.83-6.88 (m, 5H); 7.18 (d, 2H); 7.38 (d, 2H); 7.69 (t, 1H); 7.78 (s, 1H); 7.87 (d, 1H); 8.01 (d, 1H); 8.09 (s, 1H).

Example 7

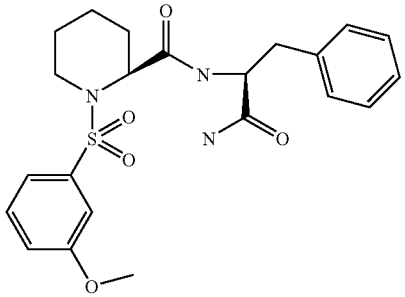

7

(S)-1-(3-Methoxy-benzenesulfonyl)-piperidine-2-carboxylic acid [(S)-1-carbamoyl-2-phenyl-ethyl]-amide 7a)

(S)-1-(3-Methoxy-benzenesulfonyl)-piperidine-2-carboxylic acid

To a solution of 7.4-g (36.00 mmol) of (S)-piperidine-2-carboxylic acid and sodium carbonate in 50 ml of water was added 3-methoxybenzenesulfonyl chloride. The mixture was stirred at room temperature for 12 hours. After that reaction mixture was washed with ether, acidified to pH 2 with 1N HCl and extracted with ethyl acetate. The organic phase was washed with water, dried (sodium sulfate) and purified by flash chromatography on silica gel eluting with 50-100% ethyl acetate/heptane to provide 3.34 g (11.17 mmol) of compound 7a. LCMS (M+H): m/z 300, retention time 1.60 min.

7b)

(S)-1-(3-Methoxy-benzenesulfonyl)-piperidine-2-carboxylic acid ((S)-1-carbamoyl-2-phenyl-ethyl)-amide To a solution of B-2528-158-0 (1.56 g, 5.21 mmol) and (S)-2-amino-3-phenyl-propionamide (1.02 g, 6.25 mmol) in 30 ml of dichloromethane was added 2.74 g (27.09 mmol) of 4-methylmorpholine followed by 1.68 g (12.50 mmol) of HOBT, 0.32 g (2.60 mmol) of DMAP and 2.78 g (14.58 mmol) of EDCI. The mixture was stirred at room temperature for 17 hours after which it was purified by flash chromatography on silica gel, eluting with 50% ethyl acetate/heptane to provide 1.69 g (3.79 mmol) of the title compound. ¹H NMR (300 MHz, CDCl₃): 0.91-1.38 (m, 5H); 2.10 (bd, 1H); 2.33 (dd, 1H); 2.99 (dd, 1H); 3.35 (dd, 1H); 3.55 (bd, 1H); 3.86 (s, 3H); 4.34 (b, 1H); 4.75 (m, 1H); 5.38 (b, 1H); 6.24 (b, 1H); 6.82 (d, 1H); 7.13 (d, 1H); 7.20-7.47 (m, 8H).

Example 8

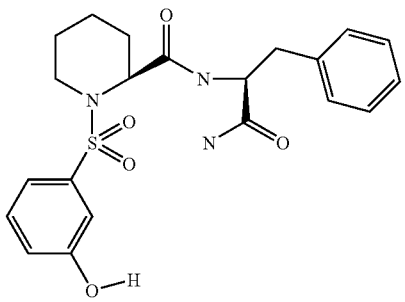

8

(S)-1-(3-Hydroxy-benzenesulfonyl)-piperidine-2-carboxylic acid ((S)-1-carbamoyl-2-phenyl-ethyl)-amide To a solution of 1.47 g (3.29 mmol) of compound 7 in 200 ml dichloromethane was slowly added 26.39 ml of tribromoborane (26.39 mmol, 1M in dichloromethane). The resulting mixture was stirred at 0 for 3 hours. Methanol (5 ml) was then added. The reaction mixture was neutralized with aqueous sodium carbonate and stirred overnight. The reaction mixture was diluted with DCM, extracted three times with DCM, washed with brine and purified by chromatography on silica gel eluting with 1% 7N NH₃ in MeOH/50% ethyl acetate/heptane to give 1.26 g of the title compound as a white solid. LCMS (M+H): m/z 432, retention time 1.55 min.

Example 9

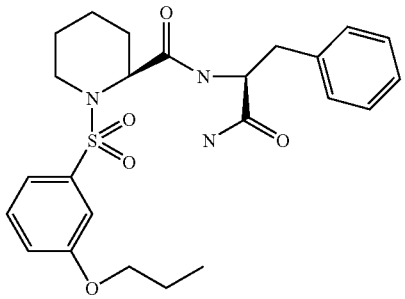

9

(S)-1-(3-Propoxy-benzenesulfonyl)-piperidine-2-carboxylic acid ((S)-1-carbamoyl-2-phenyl-ethyl)-amide To a solution of 50 mg (0.116 mmol) of compound 8 in DMF (0.5 ml) was added n-bromopropane and cesium carbonate. The mixture was stirred at room temperature for 17 hours. It was then purified by flash chromatography on silica gel, eluting with 1% 7N NH₃ in MeOH/ethyl acetate. 4 mg of the title compound was obtained. ¹H NMR (300 MHz, CDCl₃): 0.91-1.38 (m, 8H); 1.77-1.89 (m, 2H); 2.07 (bd, 1H); 2.29 (dd, 1H); 2.99 (dd, 1H); 3.36 (dd, 1H); 3.55 (bd, 1H); 3.95 (t, 2H); 4.35 (b, 1H); 4.71-4.78 (m, 1H); 5.33 (b, 1H); 6.25 (b, 1H); 6.80 (d, 1H); 7.12 (d, 1H); 7.20-7.45 (m, 8H).

Example 10

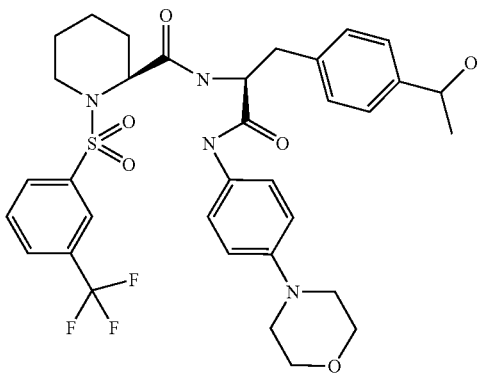

10

(S)-1-(3-Trifluoromethyl-benzenesulfonyl)-piperidine-2-carboxylic acid [(S)-2-[4-(1-hydroxyethyl)-phenyl]-1-(4-morpholin-4-yl-phenylcarbamoyl)-ethyl]-amide

10a)

(S)-3-(4-Acetyl-phenyl)-2-{[(S)-1-(3-trifluoromethyl-benzenesulfonyl)-piperidine-2-carbonyl]-amino}-propionic acid benzyl ester To a solution of 0.23 g 0.67 mmol) of compound 1b and 0.2 g (0.67 mmol) of 4-acetyl phenylalanine, benzyl ester in 6 ml of dichloromethane was added 0.28 g (3.36 mmol) of sodium bicarbonate followed by 0.22 g (1.61 mmol) of HOAT and 0.36 g (1.88 mmol) of EDCI. The mixture was stirred at room temperature for 17 hours after which it was purified by flash chromatography on silica gel, eluting with 20-50% ethyl acetate/heptane to provide 0.42 g (0.67 mmol) of compound 10a. LCMS (M+H): m/z 617, retention time 3.4 min.

10b)

(S)-3-[4-(1-Hydroxy-ethyl)-phenyl]-2-{[(S)-1-(3-trifluoromethyl-benzenesulfonyl)-piperidine-2-carbonyl]-amino}-propionic acid To 0.15 g (0.24 mmol) of (S)-3-(4-acetyl-phenyl)-2-{[(S)-1-(3-trifluoromethyl-benzenesulfonyl)-piperidine-2-carbonyl]-amino}-propionic acid benzyl ester in 30 ml of methanol was added 0.030 g of 10% palladium on carbon. The resulting suspension was stirred under 50 psi of hydrogen for 2 hours, after which the suspension was filtered and the filtrate was concentrated to provide 0.12 g (0.24 mmol) of the title compound which was used without further purification. The 300 MHz $^1$H NMR was consistent with the structure. LCMS (M+Na): m/z 551, retention time 3.05 min.

10c)

(S)-1-(3-Trifluoromethyl-benzenesulfonyl)-piperidine-2-carboxylic acid [(S)-2-[4-(1-hydroxy-ethyl)-phenyl]-1-(4-morpholin-4-yl-phenylcarbamoyl)-ethyl]-amide To a solution of 50 mg (0.0956 mmol) of compound 10b and 17 mg (0.0956 mmol) of 4-morpholinoaniline in dichloromethane (2 ml) was added 6 mg (0.045 mmol) DMAP followed by addition of sodium bicarbonate 48 mg (0.48 mmol), HOAT 31 mg (0.23 mmol) and EDCI (51 mg, 0.27 mmol). The mixture was stirred at room temperature overnight. The reaction mixture was then loaded on silica gel column, eluted with 50% ethyl acetate/heptane to provide 28 mg (0.041 mmol) of compound 10. $^1$H NMR (300 MHz, CDCl$_3$): 1.08-1.82 (m, 7H); 1.85 (dd, 1H); 2.11-2.16 (bd, 1H); 2.55 (dd, 1H); 3.10-3.16 (m, 5H); 3.30 (dt, 1H); 3.56-3.62 (bd, 1H); 3.84-3.87 (t, 4H); 4.36 (b, 1H); 4.81-4.89 (m, 2H); 6.80-6.87 (m, 3H); 7.19-7.40 (m, 6H); 7.69 (t, 1H); 7.86-7.89 (m, 2H); 8.00 (d, 1H); 8.07 (s, 1H).

Example 11

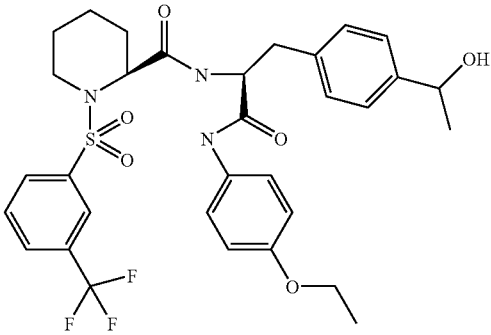

11

(S)-1-(3-Trifluoromethyl-benzenesulfonyl)-piperidine-2-carboxylic acid {(S)-1-(4-ethoxy-phenylcarbamoyl)-2-[4-(1-hydroxy-ethyl)-phenyl]-ethyl}-amide The title compound was prepared from compound 10b and 4-ethoxyaniline according to the method described for the preparation of compound 10. LCMS (M+H−H$_2$O): m/z 630, retention time 3.12 min.

Example 12

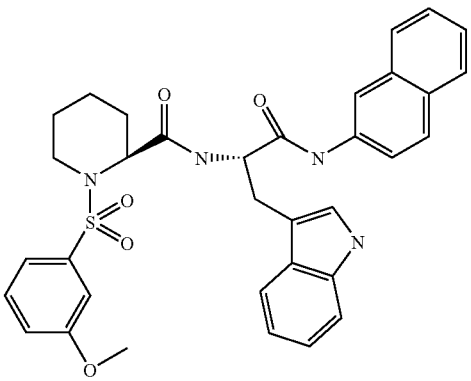

12

(S)-1-(3-Methoxy-benzenesulfonyl)-piperidine-2-carboxylic acid [(S)-2-(indol-3-yl)-1-(naphthalen-2-ylcarbamoyl)-ethyl]-amide To a solution of 0.78 g (2.60 mmol) of (S)-1-(3-methoxy-benzenesulfonyl)-piperidine-2-carboxylic acid and 1.03 g (3.12 mmol) of (S)-2-amino-3-(1-indol-3-yl)-naphthalen-2-yl-propionamide in dichloromethane (100 ml) was added 0.16 g (1.30 mmol) DMAP followed by addition of 4-methylmorpholine 1.37 g (13.54 mmol), HOBT 0.84 g (6.25 mmol) and EDCI 1.39 g (7.29 mmol). The mixture was stirred at room temperature overnight. The reaction mixture was then washed with water, dried (sodium sulfate). Chromatography on silica gel eluting with 50% ethyl acetate/heptane proved 1.2 g (1.96 mmol) of the title compound. $^1$H NMR (300 MHz, CDCl$_3$): 1.34-1.01 (m, 5H); 2.07 (bd, 1H); 2.21 (dd, 1H); 3.43-3.48 (m, 3H); 3.83 (s, 3H); 4.34 (b, 1H); 4.98 (q, 1H); 6.98 (d, 1H); 7.09-7.47 (m, 11H); 7.68-7.80 (m, 4H); 8.15 (s, 1H); 8.21 (s, 1H); 8.40 (s, 1H).

Example 13

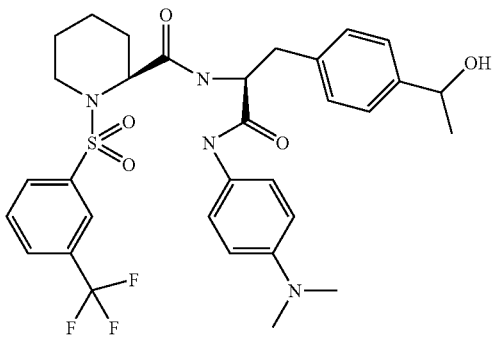

13

(S)-1-(3-Trifluoromethyl-benzenesulfonyl)-piperidine-2-carboxylic acid {(S)-1-(4-dimethylamino-phenylcarbamoyl)-2-[4-(1-hydroxy-ethyl)-phenyl]-ethyl}-amide The title compound was prepared from compound 10a and 4-dimethylaminoaniline according to the procedure employed to prepared compound 10. LCMS (M+H–H$_2$O): m/z 628, retention time 2.59 min.

Example 14

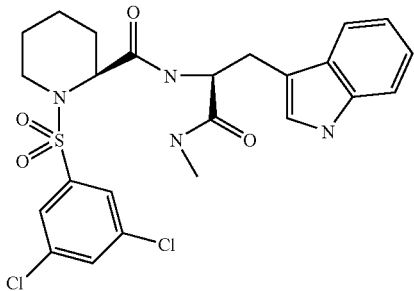

14

(S)-1-(3,5-Dichloro-benzenesulfonyl)-piperidine-2-carboxylic acid [(S)-2-(1H-indol-3-yl)-1-methylcarbamoyl-ethyl]-amide 14a)

[(S)-2-(Indol-3-yl)-1-methylcarbamoyl-ethyl]-carbamic acid benzyl ester

To a solution of 3.38 g (10.0 mmol) of N-CBZ-tryptophan in the solution of dichloromethane (100 ml) was added 6 ml of methylamine (12 mmol, 2M in THF) followed by 0.51 g (5.20 mmol) of 4-methyl-morpholine, DMAP 0.61 g (5.00 mmol), HOBT 3.24 g (24.0 mmol) and EDCI 5.30 g (28.0 mmol). The mixture was stirred at room temperature overnight, after which it was loaded onto a silica gel column and eluted with ethyl acetate to provide 2.43 g (6.92 mmol) of compound 14a. LCMS (M+H): m/z 352, retention time 1.62 min.

14b)

(S)-2-Amino-3-(indol-3-yl)-N-methyl-propionamide

To 1.89 g (5.37 mmol) of compound 14a in 240 ml of 1/1 methanol/ethyl acetate was added 0.38 g of 10% palladium on carbon under nitrogen. The resulting suspension was stirred under 1 atm of hydrogen for 1.5 hours, after which the suspension was filtered and the filtrate concentrated to provide 1.16 g (5.37 mmol) of compound 14b which was used without further purification. The 300 MHz NMR was consistent with the structure. LCMS (M+H): m/z 218, retention time 0.93 min.

14c)

(S)-1-CBZ-Piperidine-2-carboxylic acid [(S)-2-(indol-3-yl)-1-methylcarbamoyl-ethyl]-amide To a solution of 1.77 g (8.15 mmol) of compound 14b and 2.14 g (8.15 mmol) of N-CBZ-(S)-piperidine-2-carboxylic acid in 50 ml of dichloromethane was added 0.50 g (4.07 mmol) of DMAP followed by 2.65 g (19.63 mmol) of HOBT, 4.28 g (42.38 mmol) of 4-methyl morpholine and 4.37 g (22.90 mmol) of EDCI. The mixture was stirred at room temperature for 17 hours after which it was purified by flash chromatography on silica gel, eluting with 50-100% ethyl acetate/heptane to provide 2.52 g (5.45 mmol) of compound 14c. LCMS (M+H): m/z 463, retention time 1.73 min.

14d)

(S)-Piperidine-2-carboxylic acid [(S)-2-(indol-3-yl)-1-methylcarbamoyl-ethyl]-amide To 2.46 g (5.32 mmol) of compound 10c in 80 ml of 1/1 methanol/ethyl acetate was added 0.5 g of 10% palladium on carbon. The resulting suspension was stirred under 1 atm of hydrogen for 2 hours, after which the suspension was filtered and the filtrate concentrated to provide 1.51 g (4.60 mmol) of compound 14d which was used without further purification. The 300 MHz NMR was consistent with the structure. LCMS (M+H): m/z 329, retention time 1.02 min.

14e)

(S)-1-(3,5-Dichloro-benzenesulfonyl)-piperidine-2-carboxylic acid [(S)-2-indol-3-yl)-1-methylcarbamoyl-ethyl]-amide 50 mg (0.152 mmol) of compound 14d was dissolved in 1 ml of 1/1 dichloromethane/tetrahydrofuran and 0.03 ml (0.30 mmol) triethylamine and 52 mg (0.213 mmol) of 3,5-dichlorobenzenesulphonyl chloride were added. This mixture was stirred at room temperature for 2 hours. Chromatography on silica gel column provided 81 mg (0.125 mmol) of the title compound. $^1$H NMR (300 MHz, CDCl$_3$): 1.04-1.43 (m, 5H); 2.11-2.15 (bd, 1H); 2.40 (t, 1H); 2.73 (d, 3H); 3.29 (d, 2H); 3.49-3.59 (bd, 1H); 4.38 (bd, 1H); 4.69 (q, 1H); 5.89 (b, 1H); 6.80 (d, 1H); 7.12-7.23 (m, 4H); 7.36 (d, 1H); 7.55 (s, 1H); 7.61-7.64 (m, 1H); 8.11 (s, 1H).

Example 15

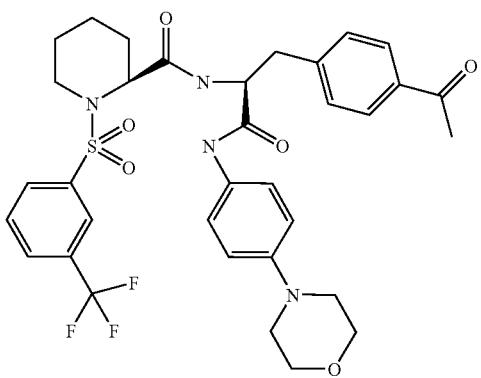

15

1-(3-Trifluoromethyl-benzenesulfonyl)-piperidine-2-carboxylic acid [2-(4-acetyl-phenyl)-1-(4-morpholin-4-yl-phenylcarbamoyl)-ethyl]-amide 15a)

(S)-3-(4-Acetyl-phenyl)-2-{[(S)-1-(3-trifluoromethyl-benzenesulfonyl)-piperidine-2-carbonyl]-amino}-propionic acid To 0.15 g (0.24 mmol) of the title compound in 30 ml of ethyl acetate was added 0.030 g of 10% palladium on carbon under nitrogen. The resulting suspension was stirred under 1 atmosphere of hydrogen for 4 hours, after which the catalyst was filtered and the filtrate was concentrated to provide 0.12 g (0.24 mmol) of the title compound which was used without further purification. The 300 MHz $^1$H NMR was consistent with the structure. LCMS (M+H): m/z 527, retention time 3.20 min.

15b)

(S)-3-(4-Acetyl-phenyl)-2-{[(S)-1-(3-trifluoromethyl-benzenesulfonyl)-piperidine-2-carbonyl]-amino}-propionic acid To 84 mg (0.16 mmol) of carboxylic acid compound 15a and 28 mg (0.16 mmol) of 4-morpholinoaniline in dichloromethane (2 ml) was added 13 mg (0.16 mmol) of sodium bicarbonate followed by 22 mg (0.16 mmol) of HOAT and 31 mg (0.16 mmol) of EDCI. The mixture was stirred at room temperature for 17 hours after which it was purified by flash chromatography on silica gel eluting with 50% ethyl acetate/heptane, to provide 83 mg (0.12 mmol) of compound 15. $^1$H NMR (300 MHz, CDCl$_3$): 1.08-1.42 (m, 5H); 2.01-2.09 (m, 1H); 2.54-2.59 (m, 4H); 3.10-3.13 (m, 4H); 3.18 (dd, 1H); 3.44 (dd, 1H); 3.60 (bd, 1H); 3.84-3.87 (m, 4H); 4.37 (bs, 1H); 4.86 (q, 1H); 6.85-6.90 (m, 3H); 7.41 (d, 4H); 7.70 (t, 1H); 7.86-7.94 (m, 4H); 8.01 (d, 1H); 8.08 (s, 1H).

Example 16

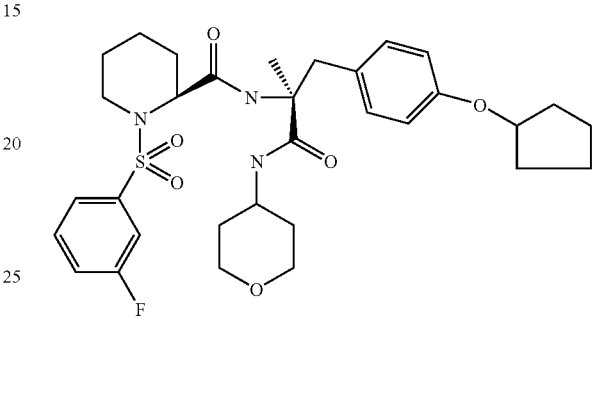

16

(S)-1-(3-Fluoro-benzenesulfonyl)-piperidine-2-carboxylic acid [2-(4-cyclopentyloxy-phenyl)-1-methyl-1-(tetrahydro-pyran-4-ylcarbamoyl)-ethyl]-amide 16a)

(S)-2-(BOC-Amino-3-(4-hydroxy-phenyl)-2-methyl-N-(tetrahydro-pyran-4-yl)-propionamide To 0.50 g (1.70 mmol) of a-methyl-N-BOC-tyrosine and 0.17 g (1.71 mmol) of tetrahydropyran-4-yl-amine in 6 ml of dichloromethane was added 0.14 g (1.70 mmol) of sodium bicarbonate, 0.23 g (1.70 mmol) of HOAT and 0.32 g (1.70 mmol) of EDCI. This mixture was stirred at room temperature overnight. Reaction mixture was then washed with water and purified by chromatography on silica gel, eluting with 50-100% ethyl acetate/heptane to provide 0.46 g (1.22 mmol) of compound 16a. LCMS (M+H): m/z 379, retention time 2.52 min.

16b)

(S)-2-(BOC-Amino-3-(4-cyclopentyloxy-phenyl)-2-methyl-N-(tetrahydro-pyran-4-yl)-propionamide To a solution of 0.13 g (0.34 mmol) of compound 16a in 2 ml of DMSO was added 0.33 g (1.00 mmol) of cesium carbonate followed by 0.15 g (0.34 mmol) of bromo-cyclopentane. This mixture was stirred at room temperature overnight. Reaction mixture was then diluted with 12 ml of ethyl acetate, washed twice with water, and with brine. The product was purified by chromatography on silica gel, eluting with 50% ethyl acetate/heptane to give 0.091 g (0.20 mmol) of compound 16b. LCMS (M+H): m/z 447, retention time 3.55 min.

16c)

(S)-2-Amino-3-(4-cyclopentyloxy-phenyl)-2-methyl-N-(tetrahydro-pyran-4-yl)-propionamide To a solution of 0.091 g (0.20 mmol) of compound 16b in 6 ml of dichloromethane was added 3 ml of trifluoroacetic acid. The mixture was stirred at room temperature for 1 hour. The pH was adjusted to 9 with saturated sodium carbonate. The solution was extracted three times with DCM, washed with brine, dried (sodium sulfate) and concentrated to a residue, which was used without further purification. LCMS (M+H): m/z 347.

16d)

(S)-1-(3-Fluoro-benzenesulfonyl)-piperidine-2-carboxylic acid [(S)-2-(4-cyclopentyloxyphenyl)-1-methyl-1-(tetrahydro-pyran-4-ylcarbamoyl)-ethyl]-amide To a solution of 0.056 g (0.19 mmol) of (S)-1-(3-fluorobenzenesulfonyl)-piperidine-2-carboxylic acid (prepared by the method employed for the synthesis of compound 1b) and 0.067 g (0.19 mmol) of compound 16c in 2 ml of dichloromethane was added 0.024 g (0.19 mmol) of DMAP, 0.026 g (0.019 mmol) of HOAT and 0.037 g (0.19 mmol) of EDCI. The mixture was stirred at room temperature overnight. Reaction mixture was purified by flash chromatograph on silica gel, eluting with 50-100% ethyl acetate/heptane to provide 0.040 g (0.065 mmol) of the title compound. $^1$H NMR (300 MHz, CDCl$_3$): 1.00-2.00 (m, 20H); 2.17 (bd, 1H); 2.81 (t, 1H); 3.13 (q, 2H); 3.45-3.52 (m, 2H); 3.69 (bd, 1H); 3.85-4.05 (m, 3H); 4.29 (b, 1H); 4.73 (b, 1H); 6.82 (d, 1H); 7.05 (d, 2H); 6.95-7.06 (m, 3H); 7.09-7.34 (m, 1H); 7.48-7.62 (m, 3H).

MS method: LCMS. Ionization type: ESI. HPLC condition: (A) 100% Water+0.1% TFA (B) 100% Acetonitrile+0.1 TFA. Gradient composition: 5% (B) to 100% (B) in 5 min, 1 ml/min. Hypersil C18 column (4.6×50 mm).

Example 17

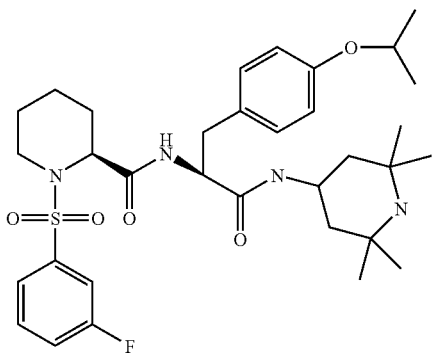

17

(S)-1-(3-Fluoro-benzenesulfonyl)-(2S)-piperidine-2-carboxylic acid [(S)-2-(4-isopropoxyphenyl)-1-(2,2,6,6-tetramethyl-piperidin-4-ylcarbamoyl)-ethyl]-amide This may be prepared by the general method of Scheme 1 above.

17a)

(S)-1-(3-(Fluoro)benzenesulfonyl)-piperidine-2-carboxylic acid benzyl ester To a mixture of (S)-piperidine-2-carboxylic acid benzyl ester hydrochloride (5.00 g, 19.5 mmol) and triethylamine (5.50 mL, 39.1 mmol) in dichloromethane (150 mL) was added 3-fluorobenzenesulfonyl chloride (3.80 g, 19.5 mmol). The mixture was stirred at room temperature for 5 h as it turned to a white suspension. The suspension was washed twice with distilled water. The organic layer was then dried over magnesium sulfate and concentrated to afford 9 g of crude oil. Flash column chromatography on silica gel (ethyl acetate/n-heptane) provided 6.51 g (88.3%) of the title compound as a yellow oil.

17b)

(S)-(1-(3-(Fluoro)-benzenesulfonyl)-piperidine-2-carboxylic acid

A mixture of (S)-1-(3-fluoro-benzenesulfonyl)-piperidine-2-carboxylic acid benzyl ester (6.51 g, 17.3 mmol), ethanol (200 mL) and 10% Pd on carbon (1.83 g, 1.70 mmol) was hydrogenated at 30 psi for 3 h. The suspension was then filtered through celite and washed with ethyl acetate. The filtrate was concentrated under reduced pressure. The resulting oil was chromatographed on silica gel (dichloromethane/n-heptane, 9/1) to afford 4.10 g (82.9%) of the title compound.

17c)

(S)-2-{1-(3-Fluoro-benzenesulfonyl)-piperidine-2-carbonyl]-amino}-3-(4-hydroxy-phenyl)-propionic acid benzyl ester.

(S)-1-(3)-(Fluoro)-benzenesulfonyl)-piperidine-2-carboxylic acid (500 mg, 1.70 mmol), (S)-2-amino-3-(4-hydroxy-phenyl)-propionic acid benzyl ester (567 mg, 2.10 mmol), 1-hydroxybenzotriazole (330 mg, 2.40 mmol) and 1-[3-(dimethylamino)propyl]-3-ethylcarbodiimide hydrochloride (434 mg, 2.30 mmol) were added to dichloromethane (10 mL). The mixture was stirred overnight and then washed with a saturated aqueous sodium bicarbonate solution. The organic layer was dried over magnesium sulfate and concentrated. The resulting oil was chromatographed on silica gel (methanol/dichloromethane, 5/95) to provide 0.735 mg (78.2%) of the title compound.

17d)

(S)-2-{(S)-[1-(3-Fluoro-benzenesulfonyl)-piperidine-2-carbonyl]-amino}-3-(4-isopropoxyphenyl)-propionic acid benzyl ester Isopropyl iodide (0.62 mL, 6.2 mmol) was added to a mixture of (S)-2-{[1-(3-(fluoro)-benzenesulfonyl)-piperidine-2-carbonyl]-amino}-3-(4-hydroxy-phenyl)-propionic acid benzyl ester (700 mg, 1.30 mmol) and cesium carbonate (2.4 g, 7.4 mmol) in dry DMF (5 mL). The suspension was stirred at room temperature for 4 h. The reaction mixture was then washed with water, dried over magnesium sulfate and concentrated under reduced pressure. The resulting oil was chromatographed (ethyl acetate/n-heptane) on silica gel to produce 620 mg (82.1%) of the title compound.

17e)

(S)-2-{[1-(3-Fluoro-benzenesulfonyl)-piperidine-2-carbonyl]-amino}-3-(4-isopropoxyphenyl)-propionic acid A mixture of (S)-2-{[(S)1-(3-fluoro-benzenesulfonyl)-piperidine-2-carbonyl]-amino}-3-(4-isopropoxy-phenyl)-propionic acid benzyl ester (0.59 g, 1.00 mmol), ethanol (20 mL) and 10% Pd on carbon (108 mg, 0.1 mmol) was hydrogenated at 30 psi for 2 h. The catalyst was filtered through Celite®. The filtrate was concentrated to afford 410 mg (83.0%) of the title compound.

17f)

(S)-1-(3-Fluoro-benzenesulfonyl)-piperidine-2-carboxylic acid [(S)-2-(4-isopropoxy-phenyl)-1-(2,2,6,6-tetramethyl-piperidin-4-yl-carbamoyl)-ethyl]-amide (S)-2-{[(S)-1-(3-Fluoro-benzenesulfonyl)-piperidine-2-carbonyl]-amino}-3-(4-isopropoxy-phenyl)-propionic acid (60 mg, 0.12 mmol), 4-amino-2,2,6,6-tetramethylpiperidine (25 mg, 0.16 mmol), TBTU (51 mg, 1.60 mmol) and N-methyl imidazole (13 mL, 0.16 mmol) were mixed in anhydrous THF (2 mL). The mixture was stirred overnight at room temperature. A saturated aqueous sodium bicarbonate solution was added and the mixture was extracted with ethyl acetate. The organic layer was dried over magnesium sulfate and concentrated under reduced pressure. The resulting oil was chromatographed (dichloromethane/methanol, 95/5) on silica gel to afford 48 mg (63%) of the title compound as a clear glass. MS: m/e 631.3 (M+H). 1H NMR (300 MHz, d6-DMSO): δ0.70-1.60 (m, 28H), 1.90 (d, 1H, J=12 Hz), 2.75 (m, 2H), 3.20 (m, 1H), 3.60 (d, 1H, J=12 Hz), 3.90 (m, 1H), 4.25 (dd, 1H, J1=9 Hz, J2=6 Hz), 4.50 (m, 2H), 6.80 (d, 2H, J=12 Hz), 7.10 (d, 2H, J=12 Hz), 7.45 (m, 4H), 7.65 (d, 1H, J=12 Hz), 7.90 (d, 1H, J=12 Hz).

Example 18

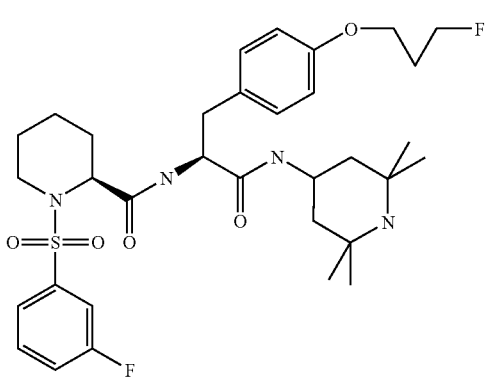

18

(S)-1-(3-Fluoro-benzenesulfonyl)-piperidine-2-carboxylic acid [(S)-2-[4-(3-fluoro-propoxy)-phenyl]-1-(2,2,6,6-tetramethyl-piperidin-4-ylcarbamoyl)-ethyl]-amide 18a)

(S)-2-{[(S)-1-(3-Fluoro-benzenesulfonyl)-piperidine-2-carbonyl]-amino}-3-[4-(3-fluoro-propoxy)-phenyl]-propionic acid benzyl ester 3-Bromo-1-fluoro propane (1.6 g, 11 mmol) was added to a mixture of (S)-2-{[(S)-1-(3-fluoro-benzenesulfonyl)-piperidine-2-carbonyl]-amino}-3-(4-hydroxy-phenyl)-propionic acid benzyl ester (compound 17c) (2.0 g, 3.7 mmol) and cesium carbonate (3.6 g, 11 mmol) in DMF (60 mL). The suspension was stirred overnight at room temperature. The reaction mixture was diluted in ethyl acetate and washed with water, dried over magnesium sulfate and concentrated. The resulting oil was chromatographed (dichloromethane/methanol, 9/1) on silica gel to produce 1.89 g (85.1%) of the title compound.

18b)

(S)-2-{[(S)-1-(3-Fluoro-benzenesulfonyl)-piperidine-2-carbonyl]-amino}-3-[4-(3-fluoropropoxy)-phenyl]-propionic acid To a mixture of (S)-2-{[(S)-1-(3-fluoro-benzenesulfonyl)-piperidine-2-carbonyl]-amino}-3-[4-(3-fluoro-propoxy)-phenyl]-propionic acid benzyl ester (1.9 g, 3.1 mmol) (compound 18a), ethanol (50 mL), and 10% Pd on carbon was hydrogenated at 30 psi for 3 h. The suspension was filtered through Celite®, washed with dichloromethane and the filtrate concentrated. The resulting oil was chromatographed (dichloromethane/methanol, 9/1) on silica gel to provide 1.04 g (64.7%) of the title compound as a white powder.

18c)

(S)-(1-(3-Fluoro-benzenesulfonyl)-piperidine-2-carboxylic acid [(S)-2-[4-(3-fluoro-propoxy)-phenyl]-1-(2,2,6,6-tetramethyl-piperidin-4-yl-carbamoyl)-ethyl]-amide (S)-2-{[(S)-1-(3-Fluoro-benzenesulfonyl)-piperidine-2-carbonyl]-amino}-3-[4-(3-fluoro-propoxy)-phenyl]-propionic acid (80 mg, 0.16 mmol), 4-amino-2,2,6,6-tetramethylpiperidine (25 mg, 0.16 mmol), 1-hydroxybenzotriazole (30 mg, 0.22 mmol) and 1-[3-(dimethylamino)propyl]-3-ethylcarbodiimide hydrochloride (39 mg, 0.20 mmol) were mixed in dichloromethane (2 mL). The mixture was stirred overnight at room temperature. The reaction mixture was diluted with dichloromethane and washed twice with a saturated aqueous sodium bicarbonate solution, and the organic fraction dried over magnesium sulfate. After filtration and subsequent concentration, the resulting oil was chromatographed (dichloromethane/methanol, 9/1) on silica gel to produce 27 mg (27%) of the title compound. MS: m/e 649.33 (M+H). ¹H NMR (300 MHz, d6-DMSO): δ0.70-2.20 (m, 27H), 2.80 (m, 2H), 3.20 (m, 1H), 3.65 (d, 1H, J=12 Hz), 4.00 (m, 3H), 4.30 (q, 1H, J=6 Hz), 4.50 (m, 2H), 4.65 (t, 1H, J=6 Hz), 6.90 (d, 2H, J=9 Hz), 7.15 (d, 2H, J=9 Hz), 7.50 (m, 4H), 8.00 (m, 2H).

Example 19

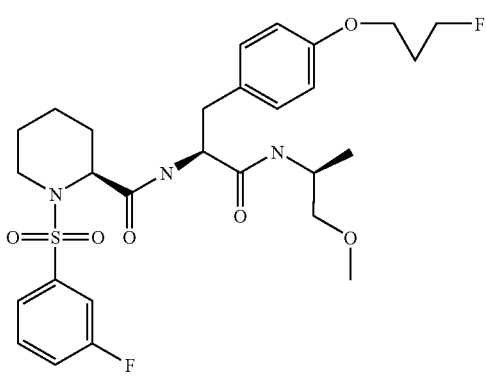

19

(S)-1-(3-Fluoro-benzenesulfonyl)-piperidine-2-carboxylic acid [(S)-2-[4-(3-fluoro-propoxy)-phenyl]-1-((S)-2-methoxy-1-methyl-ethylcarbamoyl)-ethyl]-amide (S)-2-{[1-(3-Fluoro-benzenesulfonyl)-piperidine-2-carbonyl]-amino}-3-[4-(3-fluoro-propoxy)-phenyl]-propionic acid (compound 18b) (80 mg, 0.16 mmol), (S)-1-methoxy-2-propylamine (14 mg, 0.16 mmol), 1-hydroxybenzotriazole (30 mg, 0.22 mmol) and 1-[3-(dimethylamino)propyl]-3-ethylcarbodiimide hydrochloride (39 mg, 0.20 mmol) were mixed in dichloromethane (2 mL). The mixture was stirred overnight at room temperature. The reaction mixture was diluted with dichloromethane, washed twice with a saturated aqueous sodium bicarbonate solution, and the organic layer was dried over magnesium sulfate. After manual filtration and subsequent concentration the resulting oil was chromatographed on silica gel (dichloromethane/methanol, 9/1) on silica gel to provide 66 mg (72%) of the title compound. MS: m/e 582.2 (M+H). $^1$H NMR (300 MHz, d6-DMSO): δ0.75-1.60 (m, 9H), 1.85-2.15 (m, 3H), 2.75 (m, 1H), 2.85 (m, 1H), 3.10 (m, 1H), 3.20 (m, 1H), 3.60 (d, 1H, J=12 Hz), 3.85 (m, 1H), 4.00 (t, 2H, J=6 Hz), 4.30 (q, 1H J=7.5 Hz), 4.50 (m, 2H), 4.65 (t, 1H, J=6 Hz), 6.85 (d, 2H, J=9 Hz), 7.15 (d, 2H, J=9 Hz), 7.40 (m, 4H), 7.75 (d, 1H, J=9 Hz), 7.90 (d, 1H, J=6 Hz).

Example 20

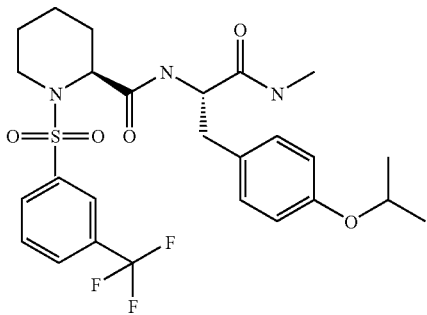

20

(S)-1-(3-Trifluoromethyl-benzenesulfonyl)-piperidine-2-carboxylic acid [(S)-2-(4-isopropoxy-phenyl)-1-methylcarbamoyl-ethyl]-amide To a room temperature solution of (S)-3-(4-isopropoxy-phenyl)-2-{[(S)-1-(3-trifluoromethyl-benzenesulfonyl)-piperidine-2-carbonyl]-amino}-propionic acid (319 mg, 0.588 mmol) (prepared according to the method described for the preparation of compound 17e), PyBroP (301 mg, 0.645 mmol), and methylene chloride (8 mL) was added methylamine (3.0 mL of a 2M THF solution) in one portion. The reaction mixture was shaken at room temperature in a sealed vessel for 2.5 h. The reaction mixture was then diluted with methylene chloride, washed with 0.5 N HCl and water successively, dried over MgSO$_4$, filtered, and evaporated. The residue was chromatographed on silica gel eluting with ethyl acetate. Homogenous fractions with Rf=0.32 (silica gel, ethyl acetate) material were combined and concentrated to afford 197 mg (60%) of the title compound as a white foam. LC/MS: RT 3.38 min, Area % 100, m/e 556 (M+H). $^1$H NMR (400 MHz, d6-DMSO) δ8.01 d (J=8 Hz; Tyr NH), 7.99 brd (J=7.5 Hz; H-6 of ArSO2), 7.94 brs (H-2 of ArSO2), 7.84 q (J=4.5 Hz; CONHMe), 7.72 brd (J=8 Hz; H-4 of ArSO2), 7.59 dd (J=8, 7.5 Hz; H-5 of ArSO2), 7.11 m (2H, AA'-part of AA'MM'; H-2/H-6 of C6H4), 6.82 m (2H, MM'-part of AA'MM'; H-3/H-5 of C6H4), 4.56 brd (J=5 Hz; Pip H-2), 4.53 qq (J=6 Hz, 6; OiPr), 4.21 ddd (J=9, 8, 5.5 Hz; Tyr Ha), 3.65 dm (J=12.5; Pip H-6 eq), 3.17 ddd (J=13, 12.5, 3; Pip H-6ax), 2.84 dd (J=13.5, 5.5; Tyr Hb), 2.66 dd (J=13.5, 9; Tyr H'b), 2.53 d (3H, J=4.5; CONHMe), 1.95 brd (J=13.5; Pip H-3 eq), 1.49 dm (J=12.5 Hz; Pip H-Seq), 1.40 m (Pip H-4 eq), 1.36 m (Pip H-3ax), 1.21 d (3H, J=6 Hz; OiPr), 1.19 d (3H, J=6 Hz; OiPr), 1.16 m (Pip H-5ax), 1.06 m (Pip H-4ax).

Example 21

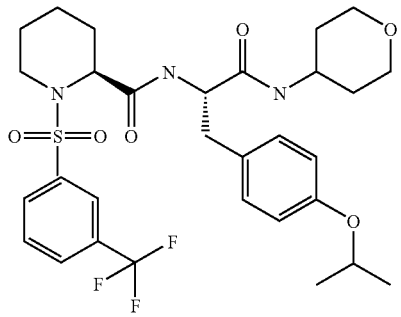

21

(S)-1-(3-Trifluoromethyl-benzenesulfonyl)-piperidine-2-carboxylic acid [(S)-2-(4-isopropoxy-phenyl)-1-(tetrahydro-pyran-4-ylcarbamoyl)-ethyl]-amide To a room temperature mixture of (S)-3-(4-isopropoxy-phenyl)-2-{[(S)-1-(3-trifluoromethyl-benzenesulfonyl)-piperidine-2-carbonyl]-amino}-propionic acid (96.0 mg, 0.177 mmol) (prepared according to the method described for the preparation of compound 17e, HOBT (29.0 mg, 0.215 mmol), 4-aminotetrahydropyran (19.6 mg, 0.194 mmol), methylene chloride (2 mL), and water (2 mL) was added EDCI (39.0 mg, 0.203 mmol) in one portion. The reaction mixture was stirred at room temperature overnight. The reaction was diluted with methylene chloride, washed with water, dried over MgSO$_4$, filtered, and concentrated. The residue was chromatographed on silica gel eluting with ethyl acetate to afford 77.1 mg (69%) of the title compound as an amorphous white solid. mp: 78.6° C. Rf=0.40 (silica gel, ethyl acetate).

LC/MS: RT 3.70 min, Area % 100, m/e 626 (M+H). $^1$H NMR (300 MHz, d6-DMSO) δ8.01 (d, J=8.2 Hz, 1H), 7.99 (brd, J=7.8 Hz, 1H), 7.94 (brs, 1H), 7.84 (d, J=7.8 Hz, 1H), 7.76 (d, J=8 Hz, 1H), 7.61 (dd, J=7.9, 7.9 Hz, 1H), 7.11 m (2H), 6.82 m (2H), 4.58-4.50 (m, 2H), 4.28-4.20 (m, 1H), 3.79-3.65 (m, 4H), 3.32-3.20 (m, 4H), 2.84-2.64 (m, 2H), 1.93 brd (J=12.7, 1H), 1.62-1.00 (m, 14H).

Example 22

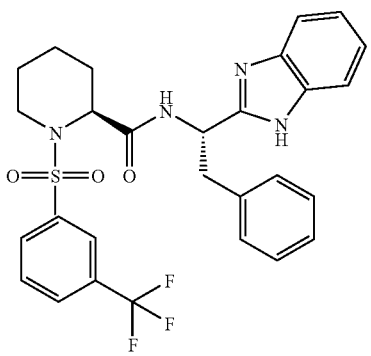

22

(S)-1-(3-Trifluoromethyl-benzenesulfonyl)-piperidine-2-carboxylic acid [(S)-2-(phenyl)-1-(benzimidazol-2-yl)-ethyl]-amide This may be prepared according to Scheme 4 above.

22a)

[(S)-1-(Methoxy-methyl-carbamoyl)-2-phenylethyl]-carbamic acid benzyl ester

Isobutyl chloroformate (0.44 mL, 3.3 mmol) and N-methylmorpholine (0.73 mL, 6.7 mmol) were added to a −15° C. solution of N-carbobenzyloxy-5-phenylalanine (1.0 g, 3.3 mmol) in CH$_2$Cl$_2$ (15 mL). After stirring at −15° C. for 20 min, N,O-dimethylhydroxylamine hydrochloride (0.34 g, 3.5 mmoles) was added, and the solution was stirred for 16 h, during which time the reaction mixture warmed to room temperature. The mixture was diluted with EtOAc (200 mL), washed with saturated aqueous NaHCO$_3$ (200 mL) and brine (200 mL). The organic layer was dried (MgSO$_4$) and concentrated in vacuo to give a colorless oil. Purification of the residue by flash chromatography on silica gel eluting with 10-30% EtOAc/heptane afforded 1.0 g (90% yield) of the title compound as a colorless oil.

22b)

((S)-1-Benzyl-2-oxo-ethyl)-carbamic acid benzyl ester

Lithium aluminum hydride (0.95 mL of a 1.0 M solution in THF, 0.95 mmoles) was added to a room temperature solution of [(S)-1-(Methoxy-methyl-carbamoyl)-2-phenyl-ethyl]-carbamic acid benzyl ester (0.30 g, 0.86 mmoles) in THF (10 mL). The resulting mixture was stirred at room temperature for 2 h, then was quenched by dilution with EtOAc (200 mL), and washed with 1% aqueous HCl (200 mL). The organic layer was dried (MgSO$_4$) and concentrated in vacuo. The residue was repeatedly diluted with CH$_3$CN (2×200 mL) and concentrated in vacuo to give 0.24 g (approximately quantitative yield) of ((S)-1-Benzyl-2-oxo-ethyl)-carbamic acid benzyl ester as a colorless oil, which was carried on without further purification: ES+ LC/MS m/e 284 (M+H), RT=4.75 min.

22c)

{(S)-1-Benzyl-2-[(E)-2-methylamino-phenylimino]-ethyl)}-carbamic acid benzyl ester 2,3-Dichloro-5,6-dicyano-1,4-benzoquinone (DDQ, 0.20 g, 0.86 mmoles) was added to a room temperature solution of ((S)-1-Benzyl-2-oxo-ethyl)-carbamic acid benzyl ester (0.24 g, 0.86 mmoles) and 1,2-phenylenediamine (0.093 g, 0.86 mmoles) in CH$_3$CN (10 mL). The reaction mixture was stirred at room temperature for 16 h, and then concentrated in vacuo. The residue was re-dissolved in EtOAc (150 mL), and washed with saturated aqueous NaHCO$_3$ (3×125 mL). The organic layer was dried (MgSO$_4$) and concentrated in vacuo to give a brown oily solid. Purification of the residue by flash chromatography on silica gel eluting with 10-40% EtOAc/heptane afforded 0.091 g (28% yield) of {(S)-1-Benzyl-2-[(E)-2-methylamino-phenylimino]-ethyl}-carbamic acid benzyl ester as a colorless oil: ES+ LC/MS m/e 372 (M+H), RT=3.03 min; $^1$H NMR (CDCl$_3$) D9.90 (bd s, 1), 7.68 (bd s, 1), 7.21-7.33 (m, 11), 7.16 (d, 2, J=6.7 Hz), 5.64 (d, 1, J=7.2 Hz), 5.15 (dd, 1, J=15.2, 7.5 Hz), 5.07 (s, 2), 3.45 (d, 2, J=7.5 Hz).

22d)

N-[(S)-2-Amino-3-phenyl-prop-(E)-ylidene]-N'-methyl-benzene-1,2-diamine

{(S)-1-Benzyl-2-[(E)-2-methylamino-phenylimino]-ethyl}-carbamic acid benzyl ester (0.075 g, 0.20 mmol) was dissolved in absolute ethanol (7 mL) and treated with 10% palladium on carbon (0.040 g). The resulting suspension was shaken under 60-65 psi H$_2$ at room temperature for 16 h. The suspension was filtered and the filter cake washed with MeOH (~100 mL), and the combined filtrates concentrated in vacuo to give N-[(S)-2-Amino-3-phenyl-prop-(E)-ylidene]-N'-methyl-benzene-1,2-diamine, as a light yellow oil (0.052 g, approximately quantitative yield): ES+ LC/MS m/e 238 (M+H), RT=3.12 min.

22e)

(S)-1-(3-Trifluoromethyl-benzenesulfonyl)-piperidine-2-carboxylic acid {(S)-1-benzyl-2-[(E)-2-methylamino-phenylimino]-ethyl}-amide PyBOP (0.11 g, 0.22 mmoles) and triethylamine (0.076 mL, 0.55 mmoles) were added to a room temperature solution of (S)-1-(3-trifluoromethyl-benzenesulfonyl)-piperidine-2- carboxylic acid (0.074 g, 0.22 mmol) in CH₂Cl₂ (5 mL). After stirring at room temperature for 20 min, a solution of N-[(S)-2-amino-3-phenyl-prop-(E)-ylidene]-N'-methyl-benzene-1,2-diamine (0.052 g, 0.22 mmoles) in CH₂Cl₂ (5 mL) was added, and the resulting mixture was stirred at room temperature for 16 h. The reaction mixture was diluted with CH₂Cl₂ (100 mL) and washed with saturated aqueous NaHCO₃ (100 mL) and brine (100 mL). The organic layer was dried (MgSO₄) and concentrated in vacuo to give a yellow oil. Purification of the residue by flash chromatography on silica gel, eluting with 10-50% EtOAc/heptane afforded 0.078 g (64%) of the title compound as a colorless powder: ES+ LC/MS m/e 557 (M+H), RT=2.92 min; ¹H NMR CDCl₃: δ9.99 (bd s, 1), 8.05 (s, 1), 7.94 (d, 1, J=8.0 Hz), 7.83 (d, 1, J=7.9 Hz), 7.62 (t, 1, J=7.9 Hz), 7.23-7.56 (m, 8), 7.00 (d, 1, J=7.5 Hz), 5.45 (m, 1), 4.40 (bd s, 1), 3.72 (dd, 1, J=14.5, 5.1 Hz), 3.54 (d, 1, J=14.1 Hz), 3.44 (dd, 1, J=14.5, 10.8 Hz), 2.13-2.26 (m, 2), 1.37 (m, 1), 1.22 (m, 1), 0.92-1.10 (m, 4).

Example 23

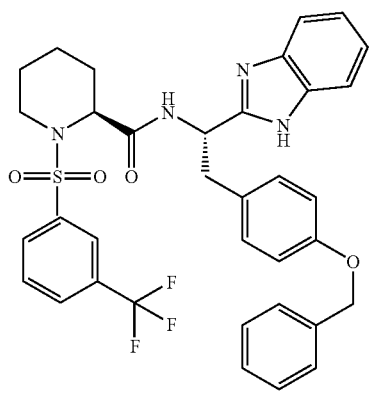

23

(S)-1-(3-Trifluoromethyl-benzenesulfonyl)-piperidine-2-carboxylic acid [(S)-1-(1H-benzimidazol-2-yl)-2-(4-benzyloxy-phenyl)-ethyl]-amide This may be prepared according to Scheme 5 above.

23a)

[(S)-1-(1H-Benzimidazol-2-yl)-2-(4-benzyloxy-phenyl)-ethyl]-carbamic acid tert-butyl ester 2-Ethoxy-1-ethoxycarbonyl-1,2,-dihydroquinoline (EEDQ, 0.17 g, 0.68 mmol) was added to a room temperature solution of (S)-3-(4-benzyloxy-phenyl)-2-tert-butoxycarbonylamino-propionic acid (0.25 g, 0.68 mmol) in DMF (3 mL). After stirring at room temperature for 20 min, a solution of 1,2-phenylenediamine (0.049 g, 0.45 mmol) in DMF (2 mL) was added, and the mixture heated at 120-140° C. for 3 days. The reaction mixture was diluted with EtOAc (100 mL) and washed with saturated NaHCO₃ (2×100 mL) and brine (100 mL). The organic layer was dried (MgSO₄) and concentrated in vacuo to give 0.20 g of a brown oil. Purification of the residue by flash chromatography on silica gel eluting with 10-50% EtOAc/heptane afforded 0.083 g (42% yield) of the title compound as a colorless powder: ES+ LC/MS m/e 444 (M+H), RT=2.89 min; ¹H NMR (CDCl₃) δ10.03 (bd s, 1), 7.73 (bd s, 1), 7.30-7.42 (m, 6), 7.24 (m, 2), 7.06 (d, 1, J=9.5 Hz), 6.83 (dd, 1, J=8.8, 1.0 Hz), 5.42 (bd s, 1), 5.07 (dd, 1, J=12.9, 7.9 Hz), 4.97 (s, 2), 3.32 (d, 2, J=7.3 Hz), 1.41 (s, 9).

23b)

(S)-1-(3-tert-Butyl-benzenesulfonyl)-piperidine-2-carboxylic acid [(S)-1-(1H-benzimidazol-2-yl)-2-(4-benzyloxy-phenyl)-ethyl]-amide Trifluoroacetic acid (0.063 mL, 0.82 mmol) was added to a room temperature solution of [(S)-1-(1H-Benzimidazol-2-yl)-2-(4-benzyloxy-phenyl)-ethyl]-carbamic acid tert-butyl ester (0.073 g, 0.16 mmol) in CH₂Cl₂ (10 mL). The resulting solution was stirred at room temperature for 2 hours, and then concentrated in vacuo to give (S)-1-(1H-Benzimidazol-2-yl)-2-(4-benzyloxy-phenyl)-ethylammonium trifluoro-acetate as a red-brown oil. This material was re-suspended in CH₂Cl₂ (4 mL) and treated with a room temperature solution of PyBOP (0.086 g, 0.16 mmoles), triethylamine (0.080 mL, 0.58 mmol), and (S)-1-(3-Trifluoromethyl-benzenesulfonyl)-piperidine-2-carboxylic acid (0.056 g, 0.16 mmol) in CH₂Cl₂ (4 mL). The resulting mixture was stirred at room temperature for 16 h. Purification of the product by flash chromatography on silica gel eluting with 10-50% EtOAc/heptane afforded 0.075 g (69%) of the title compound as a colorless powder: ES+ LC/MS m/e 663 (M+H), 100% purity; ¹H NMR (CDCl₃) ~1:1 mixture of diastereomers δ10.07 (bd s, 1), 8.07 (s, 1), 7.95 (d, 1, J=7.8 Hz), 7.81 (m, 1), 7.60 (m, 1), 7.24-7.42 (m, 9), 7.10 (d, 2, J=8.6 Hz), 6.88 (d, 2, J=8.6 Hz), 5.25-5.42 (m, 1), 5.04 (s, 2), 4.48 (bd s, 1), 3.32-3.84 (m, 3), 2.88 (m, 1), 1.05-1.77 (m, 6).

Example 24

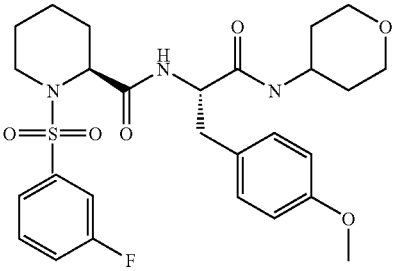

24

(S)-1-(3-Fluoro-benzenesulfonyl)-piperidine-2-carboxylic acid [(S)-2-(4-methoxy-phenyl)-1-(tetrahydro-pyran-4-ylcarbamoyl)-ethyl]-amide 24a)

(S)-2-[(S)-1-tert-Butoxycarbonyl-2-(4-hydroxy-phenyl)-ethylcarbamoyl]-piperidine-1-carboxylic acid benzyl ester 2-1H-Benzotriazol-1-yl-1,1,3,3-tetramethyluronium tetrafluoroborate (TBTU, 4.15 g, 12.9 mmoles) was added to a room temperature solution of (S)-2-amino-3-(4-hydroxy-phenyl)-propionic acid tert-butyl ester (1.70 g, 7.17 mmoles)

and 1-methylimidazole (2.60 mL, 32.7 mmoles) in 1,2-DCE (15 mL). After stirring at room temperature for 20 min, a solution of (S)-piperidine-1,2-dicarboxylic acid 1-benzyl ester (1.70 g, 6.46 mmoles) in 1,2-DCE (15 mL) was added, and the resulting mixture was stirred at room temperature for 48 h. The reaction mixture was diluted with EtOAc (200 mL) and washed with brine (3×200 mL). The aqueous layers were re-extracted with EtOAc (2×200 mL). The organic layers were dried ($Na_2SO_4$), combined, and concentrated in vacuo to give 4.21 g of an oil. Purification of the residue by flash chromatography on silica gel, eluting with 0-20% EtOAc/$CH_2Cl_2$ afforded 3.02 g (97% yield) of the title compound as a light yellow oil.

24b)

(S)-2-[(S)-1-tert-Butoxycarbonyl-2-(4-methoxy-phenyl)-ethylcarbamoyl]-piperidine-1-carboxylic acid benzyl ester Methyl iodide (4.00 mL, 64.2 mmoles) was added to a room temperature solution of (S)-2-[(S)-1-tert-Butoxycarbonyl-2-(4-hydroxy-phenyl)-ethylcarbamoyl]-piperidine-1-carboxylic acid benzyl ester (1.39 g, 2.88 mmoles) and cesium carbonate (1.87 g, 5.75 mmoles) in DMF (10 mL) and the mixture stirred at room temperature for 4 days. The reaction mixture was diluted with EtOAc (200 mL) and washed with brine (3×200 mL). The aqueous layers were re-extracted with EtOAc (2×200 mL). The organic layers were dried ($Na_2SO_4$), combined, and concentrated in vacuo to give a yellow oil. Purification of the residue by flash chromatography, eluting with 0-10% EtOAc/$CH_2Cl_2$ afforded 0.71 g (50% yield) of (S)-2-[(S)-1-tert-Butoxycarbonyl-2-(4-methoxy-phenyl)-ethylcarbamoyl]-piperidine-1-carboxylic acid benzyl ester, as a colorless oil.

24c)

(S)-3-(4-Methoxy-phenyl)-2-[((S)-piperidine-2-carbonyl)-amino]-propionic acid tert-butyl ester (S)-2-[(S)-1-tert-Butoxycarbonyl-2-(4-methoxy-phenyl)-ethylcarbamoyl]-piperidine-1-carboxylic acid benzyl ester (0.85 g, 1.7 mmoles) was dissolved in absolute ethanol (60 mL) and treated with 10% palladium on carbon (0.85 g) under a nitrogen atmosphere. The resulting suspension was shaken under 65-70 psi H2 at room temperature for 18 h after which it was filtered and the filter cake washed with EtOH (~200 mL), and concentrated in vacuo to give 0.51 g of a yellow oil. Purification of the residue by flash chromatography on silica gel eluting with 0-5% MeOH/$CH_2Cl_2$ afforded 0.26 g (42% yield) of (S)-3-(4-Methoxy-phenyl)-2-[((S)-piperidine-2-carbonyl)-amino]-propionic acid tert-butyl ester as a colorless oil: ES+ LC/MS m/e 363 (M+H), RT=2.33 min; $SiO_2$ TLC (5% MeOH/$CH_2Cl_2$) Rf=0.28.

24d)

(S)-2-{[(S)-1-(3-Fluoro-benzenesulfonyl)-piperidine-2-carbonyl]-amino}-3-(4-methoxy-phenyl)-propionic acid tert-butyl ester 3-Fluorobenzene sulfonylchloride (0.092 g, 0.47 mmoles) was added to a room temperature solution of (S)-3-(4-Methoxy-phenyl)-2-[((S)-piperidine-2-carbonyl)-amino]-propionic acid tert-butyl ester (0.13 g, 0.36 mmoles) and triethylamine (0.25 mL, 1.8 mmoles) in 1,2-DCE (3 mL) and the resulting solution heated at 50° C. for 18 h. The reaction mixture was cooled to room temperature, diluted with brine (100 mL), and extracted with $CH_2Cl_2$ (3×100 mL). The organic layers were dried ($Na_2SO_4$), combined, and concentrated in vacuo to give 0.20 g of a yellow oil. Purification of the residue by flash chromatography on silica gel eluting with 1-10% EtOAc/$CH_2Cl_2$ afforded 0.17 g (92% yield) of (S)-2-{[(S)-1-(3-Fluoro-benzenesulfonyl)-piperidine-2-carbonyl]-amino}-3-(4-methoxy-phenyl)-propionic acid tert-butyl ester, as a colorless oil: ES+ LC/MS m/e 465 (M−tBu), RT=3.73 min.

24e)

(S)-2-{[(S)-1-(3-Fluoro-benzenesulfonyl)-piperidine-2-carbonyl]-amino}-3-(4-methoxy-phenyl)-propionic acid Trifluoroacetic acid (10 mL, 130 mmoles) was added to a room temperature solution of (S)-2-{[(S)-1-(3-Fluoro-benzenesulfonyl)-piperidine-2-carbonyl]-amino}-3-(4-methoxy-phenyl)-propionic acid tert-butyl ester (0.150 g, 0.288 mmoles) in $CH_2Cl_2$ (2 mL). The reaction mixture was stirred at room temperature for 3 h after which it was concentrated in vacuo to give 0.141 g of a red-brown oil. Purification of the residue by flash chromatography with 0-30% MeOH/$CH_2Cl_2$ afforded 0.115 g (86%) of (S)-2-{[(S)-1-(3-Fluoro-benzenesulfonyl)-piperidine-2-carbonyl]-amino}-3-(4-methoxy-phenyl)-propionic acid as a colorless powder: ES+ LC/MS m/e 456 (M+H), 419 (M−CO2H), RT=3.08 min.

24f)

(S)-1-(3-Fluoro-benzenesulfonyl)-piperidine-2-carboxylic acid [(S)-2-(4-methoxy-phenyl)-1-(tetrahydro-pyran-4-ylcarbamoyl)-ethyl]-amide 2-1H-Benzotriazol-1-yl-1,1,3,3-tetramethyluronium tetrafluoroborate (TBTU, 0.072 g, 0.22 mmoles) was added to a room temperature solution of (S)-2-{[(S)-1-(3-Fluoro-benzenesulfonyl)-piperidine-2-carbonyl]-amino}-3-(4-methoxy-phenyl)-propionic acid (0.050 g, 0.108 mmoles) and 1-methylimidazole (0.050 mL, 0.63 mmoles) in 1,2-DCE (3 mL). After stirring at room temperature for 20 min, a solution of 4-aminotetrahydro-pyran (0.022 g, 0.218 mmoles) in $CH_2Cl_2$ (2 mL) was added. The resulting solution was stirred at room temperature for 48 hours. The reaction mixture was diluted with EtOAc (200 mL) and washed with brine (3×200 mL). The aqueous fraction was re-extracted with EtOAc (2×200 mL). The organic extract was dried ($Na_2SO_4$) and concentrated in vacuo to give 0.25 g of an off-white powder. Purification of the residue by flash chromatography on silica gel eluting with 1-10% MeOH/$CH_2Cl_2$ afforded 0.046 g (78%) of the title compound as a colorless oil: ES+ LC/MS m/e 548 (M+H), RT=3.39 min, 90% purity; $^1$H NMR ($CDCl_3$) δ7.51-7.68 (m, 3), 7.30-7.37 (m, 1), 7.16 (d, 2, J=8.7 Hz), 6.81-7.13 (m, 3), 6.04 (d, 1, J=7.5 Hz), 4.43 (dd, 1, J=8.0, 1.7 Hz), 4.36 (m, 1), 3.83-4.04 (m, 2), 3.80 (s, 3), 3.65 (d, 1, J=14.1 Hz), 3.40-3.52 (m, 2), 3.19 (dd, 1, J=14.1, 6.4 Hz), 2.94-3.08 (m, 1), 2.64-2.74 (m, 1), 2.07-2.22 (m, 1), 1.80-1.86 (m, 2), 1.08-1.52 (m, 8); $SiO_2$ TLC (5% MeOH/$CH_2Cl_2$) Rf=0.35.

Example 25

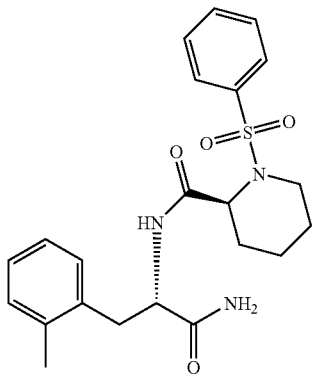

25

(S)-1-Benzenesulfonyl-piperidine-2-carboxylic acid
((S)-1-amido-2-o-tolyl-ethyl)-amide This may be prepared according to Method A, shown herein above.

A Jones tube was charged with Rink amide resin (1.0 g, 1.0 mmol/g), and the resin amine was liberated by shaking with 20% piperidine/DMF (2 mL) for ½ h. The resin was filtered, washed with DMF (5×), then re-exposed to the deprotecting solution as above. Following filtration and washing [DMF (5×), MeOH (2×), DMF (5×)], DMF was added to swell the resin followed by Fmoc-o-Me-Phe-OH (1.6 g), diisopropyl-carbodiimide (0.47 mL), HOBt (0.46 g), HBTU (1.1 g), and N,N-diisopropylethylamine (1.1 mL). The tube was capped, and the reaction mixture was shaken overnight. The reagents were filtered, and the resin was washed twice with the following sequence of solvents: [DMF (4×), DMF/$H_2O$ (2×), DMF (2×), THF (2×), THF/$H_2O$ (2×), THF (2×), and $CH_2Cl_2$ (2×)]. A sample of the beads tested negative in the Kaiser test. The resin was rinsed with DMF (2×), treated employing the above deprotection protocol for ½ hour then washed as above. After swelling the resin with DMF, N-Fmoc-2(S)-piperidine-carboxylic acid (Fmoc-pip-OH) (1.4 g) was added followed by HOAt (0.54 g), HATU (1.5 g), and N,N-diisopropylethylamine (1.4 mL). The reaction mixture was shaken overnight then washed as above followed by MeOH (2×) and $Et_2O$ (2×). A sample of the beads tested negative in the Kaiser test. The polymer-supported dipeptide was washed with DMF (2×) then deprotected and washed as in the last coupling method. Suspension of the resin in dichloromethane and addition of N,N-diisopropylethylamine (0.16 mL, 0.93 mmol) was followed by addition of benzenesulfonyl chloride (0.06 mL, 0.46 mmol). The reaction mixture was shaken overnight then washed with $CH_2Cl_2$ (3×), THF (2×), THF/$H_2O$ (2×), THF (3×), and $CH_2Cl_2$ (2×). The resin was then washed with $CH_2Cl_2$ (6×) then exposed to 20% TFA/$CH_2Cl_2$, in the presence of 0.1% triethylsilane for 1 hour at ambient temperature. Filtration of the cleavage solution followed by evaporation of the filtrate provided the desired product. LC-MS: RT=3.77 minutes (100% by ELSD); MS (ES+) 385 (M−$CONH_2$).

Example 26

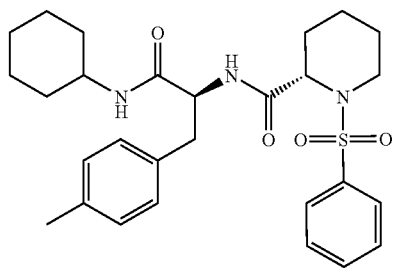

26

(S)-1-Benzenesulfonyl-piperidine-2-carboxylic acid
((S)-1-cyclohexylamido-2-p-tolyl-ethyl)-amide This may be prepared according to Method B, shown herein above.

AMEBA resin (3-methoxy-4-formylphenyl linker) (0.81 g, 1.5 mmol/g) was swelled in DMF, then treated with cyclohexylamine (0.61 mL), Na(OAc)$_3$BH (1.2 g) and AcOH (1% volume). The Jones tube was capped and several vent holes were poked in the cap with a needle. The reaction mixture was shaken overnight at room temperature. The resin was washed with DMF/$H_2O$ (3×), DMF (2×), DMF/$H_2O$ (2×), DMF (2×), THF (2×), THF/$H_2O$ (2×), THF (3×), $CH_2Cl_2$ (2×), MeOH (2×) and $Et_2O$ (1×) on a VacMaster vacuum box and dried. After checking a sample of the beads for consumption of the starting aldehyde (IR spectroscopy), the resin was sequentially coupled with Fmoc-p-Me-Phe-OH, deprotected, coupled with Fmoc-pip-OH, deprotected, sulfonylated, then cleaved using the conditions described in Method A. LC-MS: RT=3.32 minutes (100% by ELSD); MS (ES+) 512 (M+H); $^1$H NMR ☐1.07-1.39 (m, 10H), 1.50-1.54 (m, 1H), 1.61-1.64 (m, 4H), 1.89 (d, 1H, J=13 Hz), 2.25 (s, 3H), 2.75 (dd, 1H, J=9.3, 13.5 Hz), 2.87 (dd, 1H, J=5.2, 13.7 Hz), 3.14-3.12 (m, 1H), 3.46-3.48 (m, 1H), 3.58 (d, 1H, J=13.2 Hz), 4.27-4.34 (m, 1H), 4.465 (d, 1H, J=4.5 Hz), 7.08-7.15 (m, 4H), 7.38-7.44 (m, 2H), 7.57-7.61 (m, 3H), 7.745 (d, 1H, J=7.8 Hz), 7.86 (d, 1H, J=8.3 Hz).

The following compounds of Examples 27-29 were prepared according to Method B:

Example 27

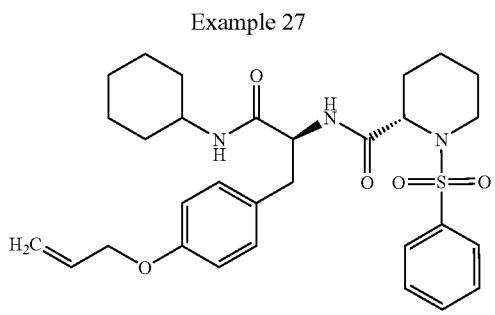

27

(S)-1-Benzenesulfonyl-piperidine-2-carboxylic acid
[(S)-2-(4-allyloxy-phenyl)-1-cyclohexylamido-ethyl]-amide LC-MS: RT=3.30 minutes (100% by ELSD); MS (ES+) 554 (M+H)

Example 28

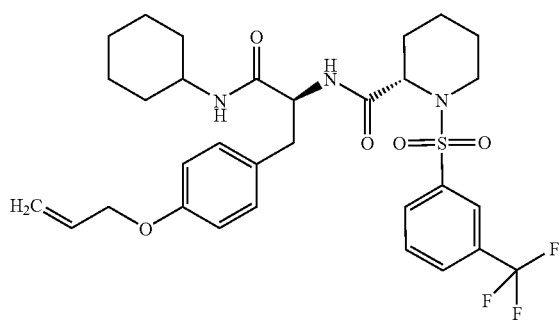

28

(S)-1-(3-Trifluoromethyl-benzenesulfonyl)-piperi-
dine-2-carboxylic acid [(S)-2-(4-allyloxy-phenyl)-1-
cyclohexylcarbamoyl-ethyl]-amide LC-MS: RT=3.51 minutes (100% by ELSD); MS (ES+) 622 (M+H).

Example 29

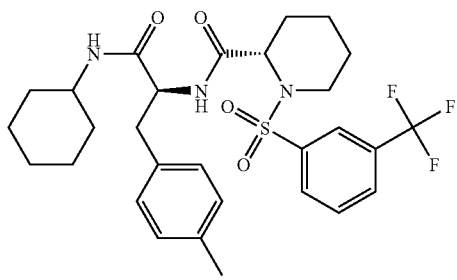

29

(S)-1-(3-Trifluoromethyl-benzenesulfonyl)-piperi-
dine-2-carboxylic acid ((S)-1-cyclohexylcarbamoyl-
2-p-tolyl-ethyl)-amide LC-MS: RT=3.52 minutes (100% by ELSD); MS (ES+) 580 (M+H); $^1$H NMR δ 0.96-1.14 (m, 7H), 1.20-1.66 (m, 8H), 1.94 (bd, 1H, J=12.7 Hz), 2.24 (s, 3H), 2.84 (dd, 1H, J=6, 13.5 Hz), 2.69 (dd, 1H, J=8.5, 13.5 Hz), 3.18-3.25 (m, 1H), 3.43-3.45 (m, 1H), 3.66 (bd, 1H, J=12.5 Hz), 4.27 (dd, 1H, J=8.3, 14.3 Hz), 4.56 (d, 1H, J=0.5 Hz), 7.10 (m, 4H), 7.56-7.61 (m, 1H), 7.70-7.76 (m, 2H), 7.94 (s, 1H), 7.96-8.01 (m, 2H).

The synthesis of the following Example illustrates the use of Method C.

Example 30

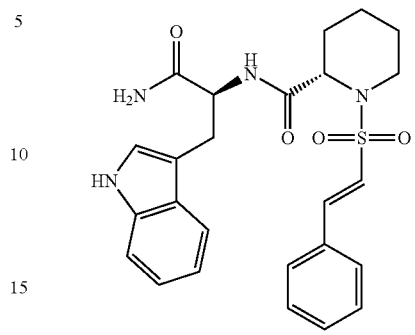

30

(S)-1-((E)-2-Phenyl-ethenesulfonyl)-piperidine-2-
carboxylic acid [(S)-1-amido-2-(1H-indol-3-yl)-
ethyl]-amide A sample of Rink amide resin (0.06 g, 1 mmol/g) was loaded with Fmoc-Trp(Boc)-OH and Fmoc-pip-OH using the conditions in Method A. After deprotection and washing of the dipeptide, dichloroethane was added followed by N,N-diisopropylethylamine (0.1 mL, 0.44 mmol). The resin was shaken for 5 minutes then treated with β-styrenesulfonyl chloride (0.06 g). The resin was placed in a FlexChem® rotational oven (Robbins) and rotated at 45 C. overnight. After allowing it to cool to ambient temperature, the resin was washed with dichloroethane (2×), CH$_2$Cl$_2$ (3×), THF (2×), THF/H$_2$O (2×), THF (3×), and CH$_2$Cl$_2$ (3×). The product was cleaved from the resin as in Method A. LC-MS: RT=3.28 minutes (100% by ELSD); MS (ES+) 436 (M−CONH2).

The synthesis of the following Example illustrates the use of Method D.

Example 31

31

(S)-1-(4,5-Dibromo-thiophene-2-sulfonyl)-piperi-
dine-2-carboxylic acid [(S)-1-amido-2-(1H-indol-3-
yl)-ethyl]-amide

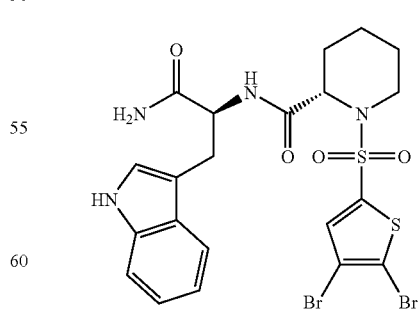

The Rink resin-supported dipeptide (0.033 g), prepared and deprotected according to Method A, was placed in a Microkan® (Irori) with a radiofrequency-encoded tag. The loaded kan was placed in a test tube (13×100 mm), and CH$_2$Cl$_2$ (1.2 mL) was added followed by N,N-diisopropylethylamine (0.06 mL) and 4,5-dibromothiophene-2-sulfonyl chloride (0.06 g). The reaction mixture was shaken overnight then washed with CH$_2$Cl$_2$ (3×), THF (2×), THF/H$_2$O (2×), THF (2×), CH$_2$Cl$_2$ (2×), MeOH (2×), and Et$_2$O (2×). The Microkan® was dried under a stream of nitrogen then cleaved with 20% TFA/CH$_2$Cl$_2$ in the presence of triethylsilane (0.1%) and isolated as in Method A. LC-MS: RT=3.50 minutes (100% by ELSD); MS (ES+) 574 (M−CONH$_2$); $^1$H NMR δ1.11-1.47 (m, 3H), 1.49-1.54 (m, 3H), 1.99 (bd, 1H, J=13.3 Hz), 2.94 (dd, 1H, J=7.7, 14.5 Hz), 3.09 (dd, 1H, J=5.7, 14.5 Hz), 3.30-3.28 (m, 1H), 3.60-3.56 (m, 1H), 4.40 (q, 1H, J=7.8, 14 Hz); 4.55 (d, 1H, J=4.5 Hz); 6.95-7.07 (m, 3H); 7.15 (d, 1H, J=7.7 Hz), 7.31 (d, 1H, J=8 Hz), 7.39 (bs, 1H), 7.59 (d, 1H, J=15 Hz), 8.01 (d, 1H, J=8 Hz), 10.80 (s, 1H).

The following Example illustrates the use of Method E, as shown hereinabove.

Example 32

35

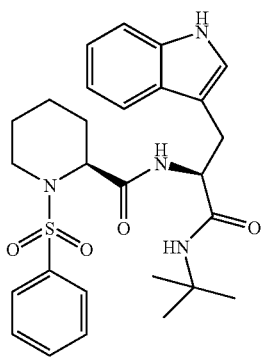

32

(S)-1-Benzenesulfonyl-piperidine-2-carboxylic acid [(S)-1-tert-butylamido-2-(1H-indol-3-yl)-ethyl]-amide A peptide synthesis vessel was charged with Marshall resin (hydroxy-thiophenol linker, Wang resin) (6 g, 1.34 mmol/g) and DMF (60 mL) was added followed by Boc-Trp-OH (5 g), HOBt (2.2 g), diisopropylcarbodiimide (2.6 mL), and 4-(dimethylamino)pyridine (0.1 g). The reaction mixture was shaken at room temperature for 24 h, and then the resin was washed with DMF (3×), THF (3×), CH$_2$Cl$_2$ (3×), and Et$_2$O (3×) and dried in vacuo overnight. The dried resin was rinsed a few times with CH$_2$Cl$_2$ then treated with 50% trifluoroacetic acid in CH$_2$Cl$_2$ (80 mL) in the presence of 1 mg indole. After shaking for 1.5 minutes, the cleavage solution was removed and fresh cleavage solution (80 mL) was added. The resin was shaken at ambient temperature for ½ h, drained, then washed with CH$_2$Cl$_2$ (4×), 5% N,N-diisopropylethylamine/CH$_2$Cl$_2$ (2×, 2 minute exposure each), and CH$_2$Cl$_2$ (13×). CH$_2$Cl$_2$ (60 mL), PhSO$_2$-pip-OH (4.8 g), and diisopropylcarbodiimide (2.8 mL) were added and the reaction mixture was shaken at room temperature for 60 h then washed using the above wash sequence. The resin was then re-exposed to the loading conditions and washed as before. A 100 mg sample of the resin was placed in a Quest® 210 reaction vessel, and pyridine (1 mL), N,N-diisopropylethylamine (0.09 mL), and t-butylamine (0.14 mL) were added. The reaction mixture was agitated at room temperature for 24 h then filtered and concentrated. The desired product was obtained after SCX chromatography (Variano BondEluto, MeOH then 2M NH$_3$/MeOH) and solvent evaporation. LC-MS: RT=1.92 minutes (70% by ELSD); MS (ES+) 511 (M+H).

The synthesis of Examples 33-35 were achieved by the use of Method F, as shown hereinabove.

Example 33

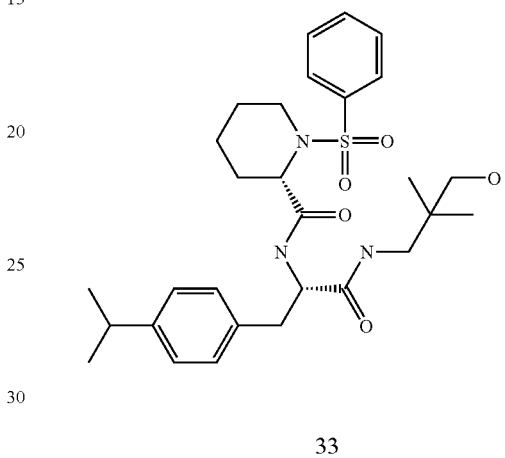

33

(S)-1-Benzenesulfonyl-piperidine-2-carboxylic acid [(S)-1-(3-hydroxy-2,2-dimethyl-propylamido)-2-(4-isopropyl-phenyl)-ethyl]-amide Wang resin (6 g, 10.2 mmol) was swelled in anhydrous DMF (60 ml) for 10 minutes in a peptide vessel, then treated with Fmoc-L-Phe(4-i-Pr)-OH (3 eq), diisopropylcarbodiimide (3 eq) and 4-(dimethylamino)pyridine (0.3 eq). The mixture was shaken overnight at room temperature. The resin was filtered and then washed successively with DMF (3×), 20% water/DMF (3×), DMF (3×), THF (3×), and CH$_2$Cl$_2$ (3×) and dried in vacuo. A 3 g (5.1 mmol) aliquot of this resin was transferred to a Jones tube, then treated with 20% piperidine/DMF (30 mL) for approximately 1 hour for Fmoc removal, washed as before and dried in vacuo. The resin was then swelled in anhydrous DMF (30 ml) for 10 minutes in a Jones tube then treated with PhSO$_2$-pip-OH (3 eq), HOBt (3 eq), HBTU (3 eq), diisopropylcarbodiimide (3 eq), and N,N-diisopropylethylamine (6 eq). The mixture was vortexed overnight, washed as before, and dried in vacuo. The resin was cleaved with 50% TFA in CH$_2$Cl$_2$ (30 ml) at room temperature for 1 hour. The mixture was filtered, the resin was rinsed with CH$_2$Cl$_2$ three times and the combined filtrate was concentrated and dried in vacuo overnight. Tetrafluorophenol resin (Wang resin, tetrafluorophenoxy linker, 1.5 g, 1.5 mmol) was swelled in anhydrous DMF (15 ml) for 10 minutes in a Jones tube and was then treated with a solution of the above prepared carboxylic acid residue in anhydrous DMF (5 ml) and diisopropylcarbodiimide (2 eq). The mixture was vortexed overnight at room temperature, washed as above, and dried in vacuo. An aliquot of this loaded resin (0.5 g, 0.5 mmol) was placed in a Jones tube then suspended in dichloroethane (5 mL) and treated with 3-amino-2,2-dimethyl-1-propanol (0.4 mmol) and shaken overnight. The mixture was filtered, the resin was rinsed with dichloroethane three times and the combined filtrate was concentrated and purified by reverse phase HPLC. LC-MS (of diastereomeric mixture): RT=3.40 minutes (100% by ELSD); MS (ES+) 544 (M+H); $^1$H NMR (CDCl$_3$) (as a ca. 3:2 mixture of diastereomers) δ0.70 (s, minor) and 0.84 (s, major, 3H), 0.78 (s, minor) and 0.86 (s, major) (3H), 1.20 (d, 3H, J=7 Hz), 1.22 (d, 3H, J=7 Hz), 0.82-1.52 (series of m, 5H), 3.00-3.86 (series of m, 10H), 4.31 (m, major) and 4.49 (m, minor) (1H), 4.52 (ddd, minor, J=8, 7.5, 7 Hz) and 4.74 (ddd, major, J=10, 8, 5.5 Hz) (1H), 6.31 (t, minor) and 6.91 (t, major, J=6 Hz) (1H), 6.73 (d, J=8 Hz, major) and 6.94 (d, minor, J=8 Hz) (1H), 7.14-7.20 (m, 4H), 7.50-7.66 (m, 3H), 7.80 (m, major) and 7.85 (m, minor) (2H).

Example 34

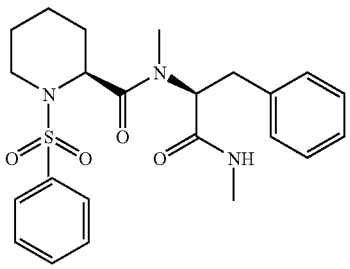

34.
(S)-1-Benzenesulfonyl-piperidine-2-carboxylic acid methyl-((S)-1-methylamido-2-phenyl-ethyl)-amide
LC-MS: RT=3.29 minutes (100% by ELSD); MS (ES+) 413 (M+H)

Example 35

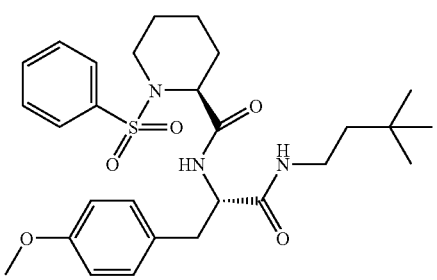

35.
(S)-1-Benzenesulfonyl-piperidine-2-carboxylic acid [(S)-1-(3,3-dimethyl-butylamido)-2-(4-methoxy-phenyl)-ethyl]-amide
LC-MS: RT=3.46 minutes (100% by ELSD); MS (ES+) 530 (M+H); $^1$H NMR (CDCl$_3$) (isolated as a 47:53 mixture of diastereomers) δ0.89 (2s, 9H), 1.10-1.19 (m, 2H), 1.21-1.50 (m, 5H), 2.19-2.08 (m, 1H), 2.42-2.50 (m, 0.5H), 2.88-3.26 (m, 4.6H), 3.62 (bd, 0.5H, J=14 Hz), 3.79 and 3.77 (s, 3H), 3.85-3.90 (bd, 0.5H, J=14 Hz), 4.37-4.38 (m, 0.5H), 4.39-4.46 (m, 0.5H), 4.48-4.50 (m, 0.5H), 4.56-4.64 (m, 0.5H), 5.51 and 6.03 (t, 1H, J=5 Hz), 6.81 and 7.03 (d, 1H, J=8 Hz), 6.84 (m, 2H) 7.13 (2 d, 2H, J=8.5 Hz), 7.64-7.51 (m, 3H), 7.82 (d, 1H, J=7.2 Hz), 7.86 (d, 1H, J=7 Hz).

Example 36

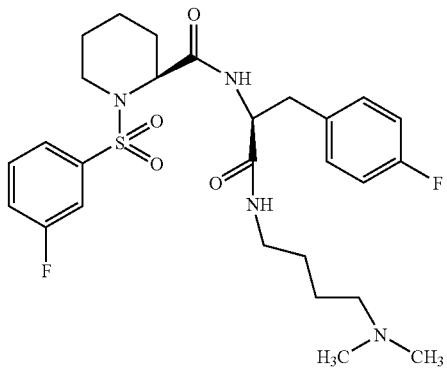

(S)-1-(3-Fluoro-benzenesulfonyl)-piperidine-2-carboxylic acid [(S)-1-(4-dimethylamino-butylcarbamoyl)-2-(4-fluoro-phenyl)-ethyl]-amide The title compound is prepared employing the procedure described for Example 4.

Example 37

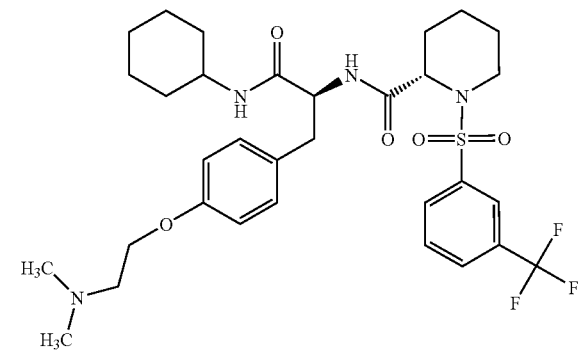

(S)-1-(3-Trifluoromethyl-benzenesulfonyl)-piperidine-2-carboxylic acid {(S)-1-cyclohexylcarbamoyl-2-[4-(2-dimethylamino-ethoxy)-phenyl]-ethyl}-amide The title compound is prepared employing the procedure described for Example 17.

Example 38

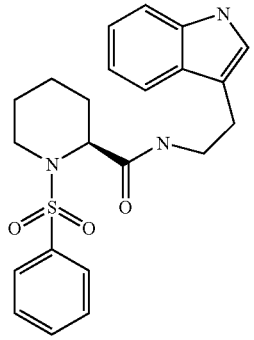

(S)-1-Benzenesulfonyl-piperidine-2-carboxylic acid [1-carbamoyl-2-(1H-indol-3-yl)-ethyl]-amide The title compound is prepared employing the procedure described for Example 7.

Example 39

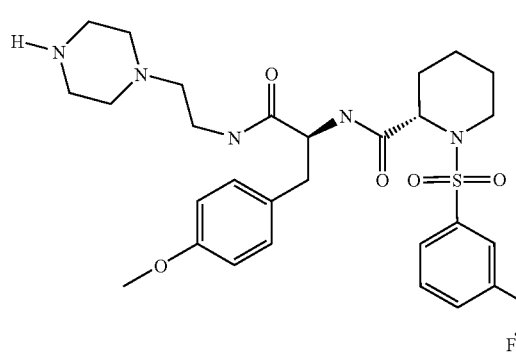

(S)-1-(3-Trifluoromethyl-benzenesulfonyl)-piperidine-2-carboxylic acid [(S)-2-(4-methoxy-phenyl)-1-(2-piperazin-1-yl-ethylcarbamoyl)-ethyl]-amide The title compound is prepared employing the procedure described for Example 4.

Example 40

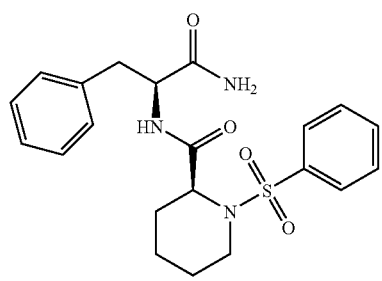

(S)-1-Benzenesulfonyl-piperidine-2-carboxylic acid ((S)-1-carbamoyl-2-phenyl-ethyl)-amide The title compound is prepared employing the procedure described for Example 7.

Example 41

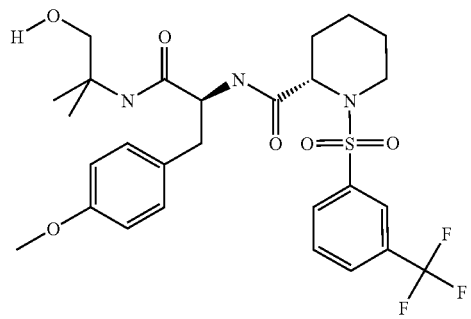

(S)-1-(3-Trifluoromethyl-benzenesulfonyl)-piperidine-2-carboxylic acid [(S)-1-(2-hydroxy-1,1-dimethyl-ethylcarbamoyl)-2-(4-methoxy-phenyl)-ethyl]-amide.

The title compound is prepared employing the procedure described for Example 4.

Example 42

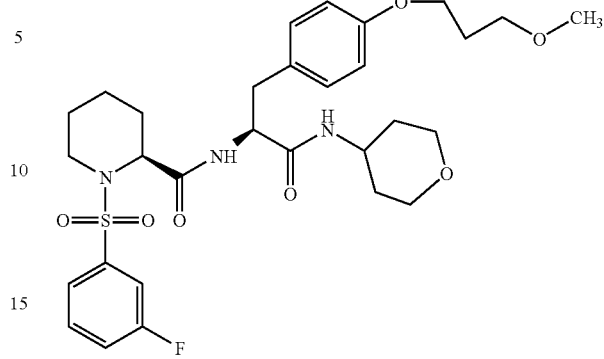

(S)-1-(3-Fluoro-benzenesulfonyl)-piperidine-2-carboxylic acid [(S)-2-[4-(3-methoxy-propoxy)-phenyl]-1-(tetrahydro-pyran-4-ylcarbamoyl)-ethyl]-amide The title compound is prepared employing the procedure described for Example 17.

Example 43

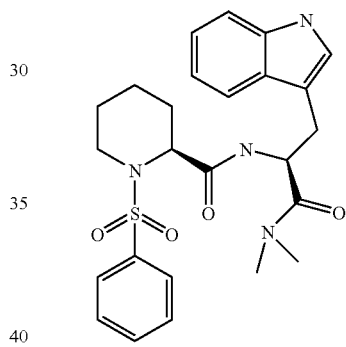

(S)1-Benzenesulfonyl-piperidine-2-carboxylic acid [(S)-1-dimethylcarbamoyl-2-(1H-indol-3-yl)-ethyl]-amide The title compound is prepared employing the procedure described for Example 4.

Example 44

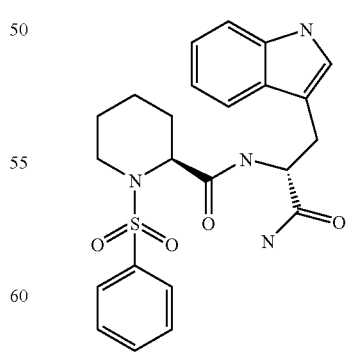

(S)-1-Benzenesulfonyl-piperidine-2-carboxylic acid [(R)-1-carbamoyl-2-(1H-indol-3-yl)-ethyl]-amide The title compound is prepared employing the procedure described for Example 7.

Example 45

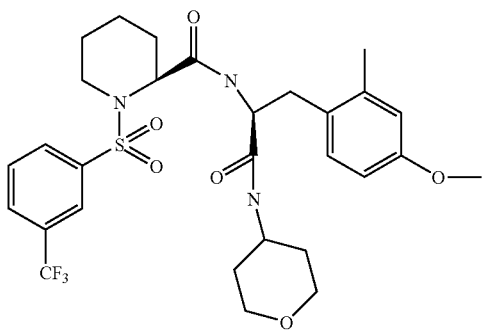

(S)-1-(3-Trifluoromethyl-benzenesulfonyl)-piperidine-2-carboxylic acid [(S)-2-(2-methyl-4-methoxy-phenyl)-1-(tetrahydro-pyran-4-ylcarbamoyl)-ethyl]-amide The title compound is prepared employing the procedure described for Example 4.

Example 46

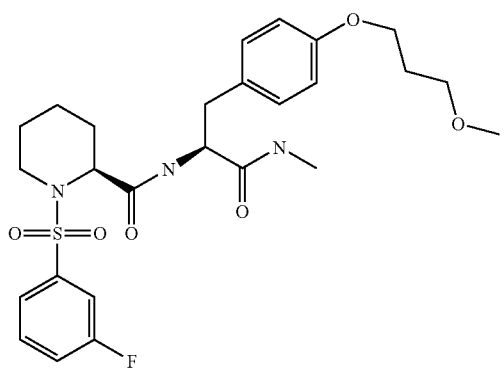

(S)-1-(3-Fluoro-benzenesulfonyl)-piperidine-2-carboxylic acid {(S)-2-[4-(3-methoxy-propoxy)-phenyl]-1-methyl-carbamoyl-ethyl}-amide To (S)-2-{[(S)-1-(3-fluoro-benzenesulfonyl)-piperidine-2-carbonyl]-amino}-3-[4-(3-methoxy-propoxy)-phenyl]-propionic acid (98 mg, 0.19 mmol) in dichloromethane (3 mL) was added, a 2.0M methyl amine solution in THF (97 μL, 1.9 mmol), PyBoP (87 mg, 0.19 mmol) at room temperature. Upon reaction completion water was added. The mixture was extracted with ethyl acetate. The organic layer was dried over magnesium sulfate and concentrated. The residue was chromatographed on silica gel (dichloromethane/ethyl acetate, 80/20 as eluant) to produce 35 (34%) mg of (S)-1-(3-fluoro-benzenesulfonyl)-piperidine-2-carboxylic acid {(S)-2-[4-(3-methoxy-propoxy)-phenyl]-1-methylcarbamoyl-ethyl}-amide. LC/MS rt=3.95, 536 m/e (M+H). $^1$H NMR (300 MHz, dmso-d6) 7.93 (d, J=8.2 Hz, 1H), 7.85 (m, 1H), 7.48-7.37 (m, 4H), 7.11 (d, J=8.3 Hz, 2H), 6.83 (d, J=8.5 Hz, 2H), 4.51 (d, J=4.5 Hz, 1H), 4.25 (m, 1H), 3.95 (t, J=6.5 Hz, 2H), 3.61 (m, 1H), 3.42 (t, J=6.2 Hz, 2H), 3.30-3.21 (m, 5H), 3.15 (m, 1H), 2.90-2.83 (m, 1H), 2.73-2.66 (m, 1H), 2.54 (d, J=4.8 Hz, 3H), 1.95-1.97 (m, 2H), 1.50-1.25 (m, 2H), 1.50-1.05 (m, 2H).

Example 47

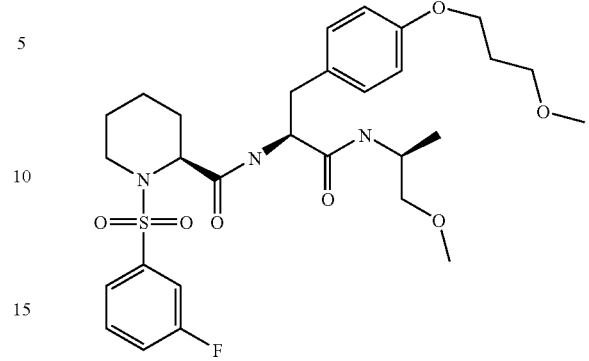

(S)-1-(3-Fluoro-benzenesulfonyl)-piperidine-2-carboxylic acid {(S)-1-((S)-2-methoxy-1-methyl-ethylcarbamoyl)-2-[4-(3-methoxy-propoxy)-phenyl]-ethyl}-amide To (S)-2-{[(S)-1-(3-fluoro-benzenesulfonyl)-piperidine-2-carbonyl]-amino}-3-[4-(3-methoxy-propoxy)-phenyl]-propionic acid (98 mg, 0.19 mmol) in dichloromethane (2 mL) was added 2-methoxy-1-(S)-methyl ethyl amine (19 mg, 0.19 mmol), 1-hydroxybenzotriazole hydrate (36 mg, 0.27 mol) and 1-(3-dimethylaminopropyl)-3-ethylcarbodiimide hydrochloride (47 mg, 0.25 mmol) at room temperature. Upon reaction completion water was added. The mixture was extracted with ethyl acetate. The organic layer was dried over magnesium sulfate and concentrated. The residue was chromatographed on silica gel (dichloromethane/ethyl acetate, 80/20 as eluant) to produce 87 (77%) mg of (S)-1-(3-fluoro-benzenesulfonyl)-piperidine-2-carboxylic acid {(S)-1-((S)-2-methoxy-1-methyl-ethylcarbamoyl)-2-[4-(3-methoxy-propoxy)-phenyl]-ethyl}-amide. LC/MS rt=3.95, 536 m/e (M+H). $^1$H NMR (300 MHz, dmso-d6) 7.90 (d, J=8 Hz, 1H), 7.76 (d, J=8 Hz, 1H), 7.48-7.37 (m, 4H), 7.13 (d, J=8.5 Hz, 2H), 6.83 (d, J=8.5 Hz, 2H), 4.50 (m, 1H), 4.28 (m, 1H), 3.96 (t, J=6.4 Hz, 2H), 3.79 (m, 1H), 3.63 (m, 1H), 3.42 (t, J=6.2 Hz, 2H), 3.30-3.21 (m, 9H), 3.17-3.05 (m, 2H), 3.90-3.82 (m, 1H), 3.75-3.65 (m, 1H), 1.98-1.85 (m, 2H), 1.45-1.10 (m, 4H), 1.00 (d, J=6.7 Hz, 3H).

Example 48

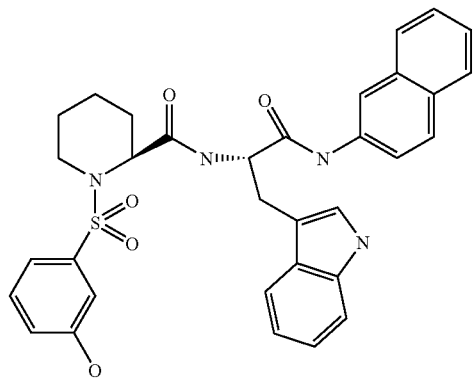

(S)-1-(3-Hydroxy-benzenesulfonyl)-piperidine-2-carboxylic acid [(S)-2-(1H-indol-3-yl)-1-(naphthalen-2-ylcarbamoyl)-ethyl]-amide The title compound is prepared employing the procedure described for Example 4.

TABLE 3

| Compound | Compound Number | Method of preparation | Reaction vessel | LC | MS |
|---|---|---|---|---|---|
| (S)-1-Benzenesulfonyl-piperidine-2-carboxylic acid [(S)-1-(2,2-dimethyl-propylamido)-2-phenyl-ethyl]-amide | 49 | Method E | Jones tube | 3.17 (100% ELSD) | 486 $(M + H)^+$ |
| (4-{(S)-2-[((S)-1-Benzenesulfonyl-piperidine-2-carbonyl)-amino]-2-amido-ethyl}-benzyl)-phosphonic acid diethyl ester | 50 | Method A | Jones tube | 3.09 (100% ELSD) | 566 $(M + H)^+$ |
| (S)-1-Benzenesulfonyl-piperidine-2-carboxylic acid [(S)-2-(4-acetylamino-phenyl)-1-amido-ethyl]-amide | 51 | Method A | Jones tube | 2.83 (100% ELSD) | 473 $(M + H)^+$ |
| (S)-1-Benzenesulfonyl-piperidine-2-carboxylic acid [(S)-1-amido-2-(4-hydroxymethyl-phenyl)-ethyl]-amide | 52 | Method A | Jones tube | 2.75 (100% ELSD) | 428 $(M - OH)^+$ |
| (S)-1-(Naphthalene-2-sulfonyl)-piperidine-2-carboxylic acid [1-amido-2-(1H-indol-3-yl)-ethyl]-amide | 53 | Method A | Jones tube | 3.35 (100% ELSD) | 460 $(M - CONH_2)^+$ |
| (S)-1-(3-Trifluoromethyl-benzenesulfonyl)-piperidine-2-carboxylic acid [(S)-1-(cyclohexylmethyl-amido)-2-(4-methylphenyl)-ethyl]-amide | 54 | Method B | Jones tube | 3.99 (100% ELSD) | 594 $(M + H)^+$ |
| (S)-1-(3-Trifluoromethyl-benzenesulfonyl)-piperidine-2-carboxylic acid [(S)-1-(4-amino-butylamido)-2(4-methylphenyl)-ethyl]-amide | 55 | Method B | Jones tube | 3.24 (100% ELSD) | 569 $(M + H)^+$ |
| (S)-1-Benzenesulfonyl-piperidine-2-carboxylic acid [(S)-1-amido-2-(1H-indol-3-yl)-ethyl]-amide | 56 | Method A | Quest 210 (Argonaut) | 1.64 (100% ELSD) | 455 $(M + H)^+$ |
| (S)-1-Benzenesulfonyl-piperidine-2-carboxylic acid ((S)-1-amido-2-pyridin-4-yl-ethyl)-amide | 57 | Method A | Quest 210 (Argonaut) | 2.59 (100% ELSD) | 417 $(M + H)^+$ |
| (S)-1-Benzenesulfonyl-piperidine-2-carboxylic acid ((S)-1-amido-2-cyclohexyl-ethyl)-amide | 58 | Method A | Quest 210 (Argonaut) | 3.50 (100% ELSD) | 377 $(M - CONH_2)^+$ |
| (S)-1-Benzenesulfonyl-piperidine-2-carboxylic acid {(S)-2-phenyl-1-[(thiophen-2-ylmethyl)-amido]-ethyl}-amide | 59 | Method A | Quest 210 (Argonaut) | 3.05 (100% ELSD) | 512 $(M + H)^+$ |

What is claimed is:

1. A compound having the general structure shown in formula I:

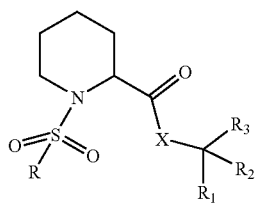

(I)

wherein:

R is an aryl selected from the group consisting of phenyl and naphthyl;

$R_1$ is hydrogen or $C_{1-6}$ alkyl;

$R_2$ is $CONHR_4$;

$R_3$ is selected from the group consisting of phenyl, phenyl $C_{1-4}$ alkyl, indolyl, indolyl $C_{1-4}$ alkyl, thiophenyl and thiophenyl $C_{1-4}$ alkyl;

X is $NR_{10}$;

wherein:

$R_4$ is selected from the group consisting of hydrogen, $C_{1-10}$ alkyl, $C_{3-8}$ cycloalkyl, hydroxy $C_{2-20}$ alkyl, $C_{1-6}$ alkoxy-$C_{2-20}$ alkyl, aryl, aryl $C_{1-10}$ alkyl, wherein the aryl group is selected from phenyl, biphenyl, naphthyl, heteroaryl and heteroaryl $C_{1-10}$ alkyl, wherein said heteroaryl is selected from thiophenyl, heterocycloalkyl or heterocycloalkyl $C_{1-10}$ alkyl wherein heterocycloalkyl is selected from tetrahydrofuranyl, tetrahydropyranyl, alkyl or unsubstituted piperidinyl, $(CH_2)_n$ piperazinyl wherein n is 1 or 2, amino, and wherein:

the aryl groups of R are optionally substituted with one or more substituents selected from the group consisting of fluorine, chlorine, bromine, $C_{1-20}$ alkyl or fluoroalkyl of the formula $C_nH_xF_y$ wherein n is an integer from 1 to 4, x is an integer from 0 to 8, y is an integer from 1 to 9 and the sum of x and y is 2n+1, $C_{1-20}$ alkoxy, $C_{1-20}$ alkenyloxy, hydroxy $C_{1-20}$ alkyl, wherein:

the groups of $R_3$ are optionally substituted with one or more substituents selected from the following: $C_{3-8}$ cycloalkyloxy, $C_{1-10}$ alkoxy, $C_{1-10}$ alkyl, $C_{3-10}$ alkenyloxy, di-($C_{1-6}$ alkyl)amino-$C_{2-6}$-alkyloxy, amino-$C_{2-6}$ alkyloxy, $CF_3$, fluoro-propoxy, $C_{1-6}$-alkoxy-$C_{2-6}$-alkoxy, benzyloxy, cyclopentyloxy, hydroxy, chloro, fluoro, bromo, hydroxy-$C_{1-10}$ alkyl, $C_{1-6}$ alkyloxo, cyano, amino, benzoyl, $C_{1-6}$ alkyloxoamino, dialkylamino-$C_{1-10}$ alkyloxy, monoalkylamino-$C_{1-10}$ alkyloxy, and amino-$C_{1-10}$ alkyloxy;

wherein:

the aryl or heteroaryl groups of $R_4$ are optionally substituted with one or more substituents selected from the following: mono- or di-($C_{1-6}$ alkyl)amino, amino, $C_{1-20}$ alkoxy, chloro, fluoro, bromo, $C_{1-10}$ alkyl, and morpholinyl; and $R_{10}$ is H, or $C_{1-6}$ alkyl or a pharmaceutically acceptable salt thereof.

2. The compound according to claim 1, wherein:

R is an aryl selected from the group consisting of phenyl, and naphthyl;

$R_1$ is hydrogen or methyl;

$R_2$ is $CONHR_4$;

$R_3$ is selected from the group consisting of phenyl, indolyl and thiophenyl;

X is $NR_{10}$;

wherein $R_4$ is selected from the group consisting of hydrogen, $C_{1-10}$ alkyl, $C_{3-8}$ cycloalkyl, hydroxy $C_{2-10}$ alkyl, $C_{1-6}$-alkoxy-$C_{2-10}$ alkyl, aryl, aryl $C_{1-6}$ alkyl, wherein the aryl group is selected from phenyl, biphenyl, heteroaryl and heteroaryl $C_{1-10}$ alkyl, wherein said heteroaryl is selected from thiophenyl, heterocycloalkyl or heterocycloalkyl $C_{1-10}$ alkyl wherein said heterocycloalkyl is selected from tetrahydrofuranyl, tetrahydropyranyl, piperidinyl, $(CH_2)_n$ piperazinyl, wherein n is 1 or 2;

and wherein the aryl groups of R are optionally substituted with one or more substituents selected from the group consisting of fluorine, chlorine, bromine, $C_{1-10}$ alkyl, fluoroalkyl or fluoroalkoxy of the formula $C_nH_xF_y$ wherein n is an integer from 1 to 4, x is an integer from 0 to 8, y is an integer from 1 to 9 and the sum of x and y is 2n+1, $C_{1-10}$ alkoxy, $C_{1-10}$ alkenyloxy, $C_{1-10}$-alkoxy-$C_{1-10}$-alkoxy, hydroxy $C_{1-10}$ alkyl;

wherein:

the groups of $R_3$ are optionally substituted with one or more substituents selected from the following: $C_{3-6}$ cycloalkyloxy, $C_{1-6}$ alkoxy, $C_{1-6}$ alkyl, $C_{3-6}$ alkenyloxy, di-($C_{1-6}$ alkyl)amino-$C_{2-6}$ alkyloxy, amino-$C_{2-6}$ alkyloxy, $CF_3$, fluoropropoxy, $C_{1-6}$ alkoxy-$C_{2-6}$ alkoxy, benzyloxy, cyclopentyloxy, hydroxy, chloro, fluoro, bromo, hydroxy-$C_{1-10}$ alkyl, $C_{1-6}$ alkyloxo, cyano, amino, benzoyl, $C_{1-6}$ alkyloxoamino, dialkylamino- $C_{1-6}$ alkyloxy, monoalkylamino-$C_{1-6}$alkyloxy, and amino- $C_{1-6}$ alkyloxy;

wherein:

the aryl or heteroaryl groups of $R_4$ are optionally substituted with one or more substituents selected from the following: mono- or di-($C_{1-6}$ alkyl)amino, amino, $C_{1-10}$ alkoxy, chloro, fluoro, bromo, $C_{1-10}$ alkyl, and morpholinyl;

$R_{10}$ is H.

3. The compound according to claim 2, wherein:

R is phenyl or naphthyl;

$R_1$ is hydrogen, $R_2$ is $CONHR_4$, $R_3$ is selected from the group consisting of phenyl, indolyl and thiophenyl, X is NH wherein $R_4$ is selected from the group consisting of hydrogen, $C_{1-10}$ alkyl, $C_{3-8}$ cycloalkyl, hydroxy $C_{2-10}$ alkyl, aryl, wherein said aryl is selected from the group consisting of phenyl, naphthyl, heteroaryl or heteroaryl $C_{1-6}$-alkyl, wherein said heteroaryl is thiophenyl, and heterocycloalkyl or heterocycloalkyl $C_{1-6}$ alkyl, wherein said heterocycloalkyl is selected from tetrahydrofuranyl, tetrahydropyranyl, morpholinyl, alkyl or un-substituted piperidinyl, and piperazinyl;

wherein: phenyl of R is optionally substituted with one or more substituents selected from the group consisting of fluorine, chlorine, bromine, $C_{1-10}$ alkyl, $CF_3$, $C_{1-10}$ alkoxy, $C_{1-10}$ alkenyloxy;

wherein: the $R_3$ is optionally substituted with one or more substituents selected from: $C_{3-6}$ cycloalkyloxy, $C_{1-6}$ alkoxy, $C_{1-6}$ alkyl, $C_{3-6}$ alkenyloxy, di-($C_{1-6}$ alkyl) amino-$C_{2-6}$-alkyloxy, amino- $C_{2-6}$ alkyloxy, $C_{1-6}$-alkoxy- $C_{2-6}$-alkoxy, hydroxy, chloro, fluoro, bromo, and amino, 4-aryloxo;

wherein: the aryl or heteroaryl groups of $R_4$ are optionally substituted with one or more substituents selected from the following: mono- or di-($C_{1-6}$-alkyl)amino, amino, $C_{1-6}$ alkoxy, chloro, fluoro, bromo, $C_{1-6}$-alkyl, and morpholinyl.

4. The compound according to claim 1, wherein:

R is phenyl and naphthyl;

$R_1$ is hydrogen;

$R_2$ is $CONHR_4$;

$R_3$ is phenyl;

X is NH $R_4$, is selected from the group consisting of hydrogen, $C_{1-10}$ alkyl, $C_{3-6}$ cycloalkyl, 2-hydroxyethyl, 2-(2-hydroxyethoxy)ethyl, 3-hydroxypropyl, 2-methoxyethylaryl, wherein aryl is selected from phenyl and naphthyl; aryl $C_1$-alkyl, wherein aryl is selected from the group consisting of phenyl, and biphenyl, heteroaryl $C_1$-alkyl, wherein heteroaryl is selected from the group consisting of 2-thiophenyl and 2-pyridinyl, heterocycloalkyl, wherein heterocycloalkyl is selected from the group consisting of 4-tetrahydropyranyl, 4-piperidinyl, 2,2,6,6-tetramethylpiperidinyl and 1-ethyl-4-piperidinyl, heterocycloalkyl-$C_1$-alkyl, wherein heterocycloalkyl is selected from the group consisting of 4-tetrahydropyranyl and 2-tetrahydrofuranyl, 2- heterocycloalkyl-$C_2$-alkyl, wherein heterocycloalkyl is selected from the group consisting of 4-tetrahydropyranyl and 1-piperazinyl;

wherein: the phenyl of R is optionally substituted with one or two substituents in the 3-, 4-, or 5-positions selected from the group consisting of fluorine, chlorine, bromine, trifluoromethyl, $C_{1-7}$ alkyloxy, $C_{1-7}$ alkenyloxy, $C_{1-8}$ alkyl, and $C_{2-3}$ hydroxypropyl;

the naphthyl of R is optionally substituted with one of the substituents selected from chlorine, fluorine, and dimethylamino;

the phenyl of $R_3$ is optionally substituted with one or two substituents selected from the group consisting of $C_{1-5}$ alkyl, $C_{1-5}$ alkyloxy, 2-dimethylaminoethoxy, 2-pyrrolidino-ethoxy, 3-fluoropropyloxy, 3-methoxypropyloxy, cyclopentoxy, benzyloxy, hydroxy, chloro, fluoro, bromo, trifluoromethyl, 1-hydroxyethyl, acetyl, allyloxy, cyano, amino, 4-benzoyl, and acetoxy;

the phenyl of $R_4$ is optionally substituted with one or two substituents selected from the group consisting of 4-dimethylamino, 4-methylamino, 4-amino, methoxy, ethoxy, chloro, 4-morpholino, fluoro, and methyl.

5. The compound according to claim 1, selected from:

(S)-1-(3-Trifluoromethyl-benzenesulfonyl)-piperidine-2-carboxylic acid [(S)-1-(4-dimethylamino-phenylcarbamoyl)-2-(4-methoxy-phenyl)-ethyl]-amide;

(S)-1-(3-Trifluoromethyl-benzenesulfonyl)-piperidine-2-carboxylic acid [(S)-2-(4-acetyl-phenyl)-1-(4-ethoxy-phenylcarbamoyl)-ethyl]-amide;

(S)-1-(3-Trifluoromethyl-benzenesulfonyl)-piperidine-2-carboxylic acid [(S)-1-(4-morpholin-4-yl-phenylcarbamoyl)-2-(4-trifluoromethyl-phenyl)-ethyl]-amide;

(S)-1-(3-Trifluoromethyl-benzenesulfonyl)-piperidine-2-carboxylic acid [(S)-2-(4-methoxy-phenyl)-1-(tetrahydro-pyran-4-ylcarbamoyl)-ethyl]-amide;

(S)-1-(3-Trifluoromethyl-benzenesulfonyl)-piperidine-2-carboxylic acid [(S)-2-(2-methyl-4-methoxy-phenyl)-1-(tetrahydro-pyran-4-ylcarbamoyl)-ethyl]-amide;

(S)-1-(3-Trifluoromethyl-benzenesulfonyl)-piperidine-2-carboxylic acid [(S)-2-(3,4-dimethoxy-phenyl)-1-(tetrahydro-pyran-4-yl-carbamoyl)-ethyl]-amide;

(S)-1-(3-Trifluoromethyl-benzenesulfonyl)-piperidine-2-carboxylic acid [(S)-2-(4-methoxy-phenyl)-1-(4-morpholin-4-yl-phenylcarbamoyl)-ethyl]-amide;

(S)-1-(3-Methoxy-benzenesulfonyl)-piperidine-2-carboxylic acid ((S)1-carbamoyl-2-phenyl-ethyl)-amide;

(S)-1-(3-Hydroxy-benzenesulfonyl)-piperidine-2-carboxylic acid ((S)-1-carbamoyl-2-phenyl-ethyl)-amide;

(S)-1-(3-Propoxy-benzenesulfonyl)-piperidine-2-carboxylic acid ((S)-1-carbamoyl-2-phenyl-ethyl)-amide;

(S)-1-(3-Trifluoromethyl-benzenesulfonyl)-piperidine-2-carboxylic acid [(S)-2-[4-(1-hydroxy-ethyl)-phenyl]-1-(4-morpholin-4-yl-phenylcarbamoyl)-ethyl]-amide;

(S)-1-(3-Trifluoromethyl-benzenesulfonyl)-piperidine-2-carboxylic acid {(S)-1-(4-ethoxy-phenylcarbamoyl)-2-[4-(1-hydroxy-ethyl)-phenyl]-ethyl}-amide;

(S)-1-(3-Methoxy-benzenesulfonyl)-piperidine-2-carboxylic acid [(S)-2-(indol-3-yl)-1-(naphthalen-2-ylcarbamoyl)-ethyl]-amide;

(S)-1-(3-Trifluoromethyl-benzenesulfonyl)-piperidine-2-carboxylic acid {(S)-1-(4-dimethylamino-phenylcarbamoyl)-2-[4-(1-hydroxy-ethyl)-phenyl]-ethyl}-amide;

(S)-1-(3,5-Dichloro-benzenesulfonyl)-piperidine-2-carboxylic acid [(S)-2-(1H-indol-3-yl)-1-methylcarbamoyl-ethyl]-amide;

(S)-1-(3-Trifluoromethyl-benzenesulfonyl)-piperidine-2-carboxylic acid [(S)-2-(4-acetyl-phenyl)-1-(4-morpholin-4-yl-phenylcarbamoyl)-ethyl]-amide;

(S)-1-(3-Fluoro-benzenesulfonyl)-piperidine-2-carboxylic acid [(S)-2-(4-cyclopentyloxy-phenyl)-1-methyl-1-(tetrahydro-pyran-4-ylcarbamoyl)-ethyl]-amide;

(S)-1-(3-Fluoro-benzenesulfonyl)-piperidine-2-carboxylic acid [(S)-2-(4-isopropoxy-phenyl)-1-(2,2,6,6-tetramethyl-piperidin-4-ylcarbamoyl)-ethyl]-amide;

(S)-1-(3-Fluoro-benzenesulfonyl)-(2S)-piperidine-2-carboxylic acid [(S)-2-[4-(3-fluoro-propoxy)-phenyl]-1-(2,2,6,6-tetramethyl-piperidin-4-ylcarbamoyl)-ethyl]-amide;

(S)-1-(3-Fluoro-benzenesulfonyl)-piperidine-2-carboxylic acid [(S)-2-[4-(3-fluoro-propoxy)-phenyl]-1-((S)-2-methoxy-1-methyl-ethylcarbamoyl)-ethyl]-amide;

(S)-1-(3-Trifluoromethyl-benzenesulfonyl)-piperidine-2-carboxylic acid [(S)-2-(4-isopropoxy-phenyl)-1-methylcarbamoyl-ethyl]-amide;

(S)-1-(3-Trifluoromethyl-benzenesulfonyl)-piperidine-2-carboxylic acid [(S)-2-(4-isopropoxy-phenyl)-1-(tetrahydro-pyran-4-ylcarbamoyl)-ethyl]-amide;

(S)-1-(3-Fluoro-benzenesulfonyl)-piperidine-2-carboxylic acid [(S)-2-(4-methoxy-phenyl)-1-(tetrahydropyran-4-yl-carbamoyl)-ethyl]-amide;

(S)-1-Benzenesulfonyl-piperidine-2-carboxylic acid ((S)-1-amido-2-(2-methylphenyl)-ethyl)-amide;

(S)-1-Benzenesulfonyl-piperidine-2-carboxylic acid ((S)-1-cyclohexylamido-2-(4-methylphenyl)-ethyl)-amide;

(S)-1-Benzenesulfonyl-piperidine-2-carboxylic acid [(S)-2-(4-allyloxy-phenyl)-1-cyclohexylamido-ethyl]-amide;

(S)-1-(3-Trifluoromethyl-benzenesulfonyl)-piperidine-2-carboxylic acid [(S)-2-(4-allyloxy-phenyl)-1-cyclohexylcarbamoyl-ethyl]-amide;

(S)-1-(3-Trifluoromethyl-benzenesulfonyl)-piperidine-2-carboxylic acid ((S)-1-cyclohexylamido-2-(4-methylphenyl)-ethyl)-amide;

(S)-1-Benzenesulfonyl-piperidine-2-carboxylic acid [(S)-1-tert-butylamido-2-(1H-indol-3-yl)-ethyl]-amide;

(S)-1-Benzenesulfonyl-piperidine-2-carboxylic acid [(S)-1-(3-hydroxy-2,2-dimethyl-propylamido)-2-(4-isopropyl-phenyl)-ethyl]-amide;

(S)-1-Benzenesulfonyl-piperidine-2-carboxylic acid methyl-((S)-1-methylamido-2-(phenyl)-ethyl)-amide;

(S)-1-Benzenesulfonyl-piperidine-2-carboxylic acid [(S)-1-(3,3-dimethyl-butylamido)-2-(4-methoxyphenyl)-ethyl]-amide;

(S)-1-Benzenesulfonyl-piperidine-2-carboxylic acid [(S)-1-(2,2-dimethyl-propylamido)-2-(phenyl)-ethyl]-amide;

(S)-1-Benzenesulfonyl-piperidine-2-carboxylic acid [(S)-2-(4-(acetylamino)-phenyl)-1-amido-ethyl]-amide;

(S)-1-Benzenesulfonyl-piperidine-2-carboxylic acid [(S)-1-amido-2-(4-(hydroxymethyl)-phenyl)-ethyl]-amide;

(S)-1-(Naphthalene-2-sulfonyl)-piperidine-2-carboxylic acid [(S)-1-amido-2-(1H-indol-3-yl)-ethyl]-amide;

(S)-1-(3-Trifluoromethyl-benzenesulfonyl)-piperidine-2-carboxylic acid [(S)-1-(cyclohexylmethyl-amido)-2-(4-methylphenypethyl)-amide;

(S)-1-Benzenesulfonyl-piperidine-2-carboxylic acid [(S)-1-amido-2-(1H-indol-3-yl)-ethyl]-amide;

(S)-1-Benzenesulfonyl-piperidine-2-carboxylic acid ((S)-1-amido-2-cyclohexyl-ethyl)-amide;

(S)-1-Benzenesulfonyl-piperidine-2-carboxylic acid {(S)-2-phenyl-1- [(thiophen-2-ylmethyl)-amido]-ethyl}-amide;

(S)-1-(3-Fluoro-benzenesulfonyl)-piperidine-2-carboxylic acid [(S)-2-[4-(3-methoxy-propoxy)-phenyl]-1-(tetrahydro-pyran-4-ylcarbamoyl)-ethyl]-amide;

(S)-1-(3-Trifluoromethyl-benzenesulfonyl)-piperidine-2-carboxylic acid {(S)-1-cyclohexylcarbamoyl-2[4-(2-dimethylamino-ethoxy)-phenyl]-ethyl}-amide;

(S)-1-(3-Trifluoromethyl-benzenesulfonyl)-piperidine-2-carboxylic acid [(S)-2-(4-methoxy-phenyl)-1-(2-piperazin-1-yl-ethylcarbamoyl)-ethyl]-amide;

(S)-1-(3-Trifluoromethyl-benzenesulfonyl)-piperidine-2-carboxylic acid [(S)-1-(2-hydroxy-1,1-dimethyl-ethylcarbamoyl)-2-(4-methoxy-phenyl)-ethyl]-amide;

(S)-1-Benzenesulfonyl-piperidine-2-carboxylic acid ((S)-1-carbamoyl-2-phenyl-ethyl)-amide;

(S)-1-(3-Fluoro-benzenesulfonyl)-piperidine-2-carboxylic acid {(S)-2[4-(3-methoxy-propoxy)-phenyl]-1-methylcarbamoyl-ethyl}-amide;

(S)-1-(3-Fluoro-benzenesulfonyl)-piperidine-2-carboxylic acid {(S)-1-((S)-2-methoxy-1-methyl-ethylcarbamoyl)-2-[4-(3-methoxy-propoxy)-phenyl]-ethyl}-amide; and (S)-1-(3-Hydroxy-benzenesulfonyl)-piperidine-2-carboxylic acid [(S)-2-(1H-indol-3-yl)-1-(naphthalen-2-ylcarbamoyl)-ethyl]-amide.

6. A pharmaceutical composition comprising the compound of formula I as recited in claim 1, or an enantiomer thereof or a pharmaceutically acceptable salt thereof in combination with one or more pharmaceutically acceptable carrier compounds, solvents, solutions or suspensions.

7. The pharmaceutical composition as recited in claim 6, wherein said compound of formula I is as defined in claim 2.

8. The pharmaceutical composition as recited in claim 6, wherein said compound of formula I is as defined in claim 3.

9. The pharmaceutical composition as recited in claim 6, wherein said compound of formula I is as defined in claim 4.

10. A pharmaceutical composition as recited in claim 6, wherein the compound is selected from the group consisting of:

(S)-1-(3-Trifluoromethyl-benzenesulfonyl)-piperidine-2-carboxylic acid [(S)-1-(4-dimethylamino-phenylcarbamoyl)-2-(4-methoxy-phenyl)-ethyl]-amide;

(S)-1-(3-Trifluoromethyl-benzenesulfonyl)-piperidine-2-carboxylic acid [(S)-2-(4-acetyl-phenyl)-1-(4-ethoxyphenylcarbamoyl)-ethyl]-amide;

(S)-1-(3-Trifluoromethyl-benzenesulfonyl)-piperidine-2-carboxylic acid [(S)-1-(4-morpholin-4-yl-phenylcarbamoyl)-2-(4-trifluoromethyl-phenyl)-ethyl]-amide;

(S)-1-(3-Trifluoromethyl-benzenesulfonyl)-piperidine-2-carboxylic acid [(S)-2-(4-methoxy-phenyl)-1-(tetrahydro-pyran-4-ylcarbamoyl)-ethyl]-amide;

(S)-1-(3-Trifluoromethyl-benzenesulfonyl)-piperidine-2-carboxylic acid [(S)-2-(2-methyl-4-methoxy-phenyl)-1-(tetrahydro-pyran-4-ylcarbamoyl)-ethyl]-amide;

(S)-1-(3-Trifluoromethyl-benzenesulfonyl)-piperidine-2-carboxylic acid [(S)-2-(3,4-dimethoxy-phenyl)-1-(tetrahydro-pyran-4-yl-carbamoyl)-ethyl]-amide;

(S)-1-(3-Trifluoromethyl-benzenesulfonyl)-piperidine-2-carboxylic acid [(S)-2-(4-methoxy-phenyl)-1-(4-morpholin-4-yl-phenylcarbamoyl)-ethyl]-amide;

(S)-1-(3-Methoxy-benzenesulfonyl)-piperidine-2-carboxylic acid ((S)1-carbamoyl-2-phenyl-ethyl)-amide;

(S)-1-(3-Hydroxy-benzenesulfonyl)-piperidine-2-carboxylic acid ((S)-1-carbamoyl-2-phenyl-ethyl)-amide;

(S)-1-(3-Propoxy-benzenesulfonyl)-piperidine-2-carboxylic acid ((S)-1-carbamoyl-2-phenyl-ethyl)-amide;

(S)-1-(3-Trifluoromethyl-benzenesulfonyl)-piperidine-2-carboxylic acid [(S)-2-[4-(1-hydroxy-ethyl)-phenyl]-1-(4-morpholin-4-yl-phenylcarbamoyl)-ethyl]-amide;

(S)-1-(3-Trifluoromethyl-benzenesulfonyl)-piperidine-2-carboxylic acid {(S)-1-(4-ethoxy-phenylcarbamoyl)-2-[4-(1-hydroxy-ethyl)-phenyl]-ethyl}-amide;

(S)-1-(3-Methoxy-benzenesulfonyl)-piperidine-2-carboxylic acid [(S)-2-(indol-3-yl)-1-(naphthalen-2-ylcarbamoyl)-ethyl]-amide;

(S)-1-(3-Trifluoromethyl-benzenesulfonyl)-piperidine-2-carboxylic acid {(S)-1-(4-dimethylamino-phenylcarbamoyl)-2-[4-(1-hydroxy-ethyl)-phenyl]-ethyl}-amide;

(S)-1-(3,5-Dichloro-benzenesulfonyl)-piperidine-2-carboxylic acid [(S)-2-(1H-indol-3-yl)-1-methylcarbamoyl-ethyl]-amide;

(S)-1-(3-Trifluoromethyl-benzenesulfonyl)-piperidine-2-carboxylic acid [(S)-2-(4-acetyl-phenyl)-1-(4-morpholin-4-yl-phenylcarbamoyl)-ethyl]-amide;

(S)-1-(3-Fluoro-benzenesulfonyl)-piperidine-2-carboxylic acid [(S)-2-(4-cyclopentyloxy-phenyl)-1-methyl-1-(tetrahydro-pyran-4-ylcarbamoyl)-ethyl]-amide;

(S)-1-(3-Fluoro-benzenesulfonyl)-piperidine-2-carboxylic acid [(S)-2-(4-isopropoxy-phenyl)-1-(2,2,6,6-tetramethyl-piperidin-4-ylcarbamoyl)-ethyl]-amide;

(S)-1-(3-Fluoro-benzenesulfonyl)-(2S)-piperidine-2-carboxylic acid [(S)-2-[4-(3-fluoro-propoxy)-phenyl]-1-(2,2,6,6-tetramethyl-piperidin-4-ylcarbamoyl)-ethyl]-amide;

(S)-1-(3-Fluoro-benzenesulfonyl)-piperidine-2-carboxylic acid [(S)-2-[4-(3-fluoro-propoxy)-phenyl]-1-((S)-2-methoxy-1-methyl-ethylcarbamoyl)-ethyl]-amide;

(S)-1-(3-Trifluoromethyl-benzenesulfonyl)-piperidine-2-carboxylic acid [(S)-2-(4-isopropoxy-phenyl)-1-methylcarbamoyl-ethyl]-amide;

(S)-1-(3-Trifluoromethyl-benzenesulfonyl)-piperidine-2-carboxylic acid [(S)-2-(4-isopropoxy-phenyl)-1-(tetrahydro-pyran-4-ylcarbamoyl)-ethyl]-amide;

(S)-1-(3-Fluoro-benzenesulfonyl)-piperidine-2-carboxylic acid [(S)-2-(4-methoxy-phenyl)-1-(tetrahydropyran-4-yl-carbamoyl)-ethyl]-amide;

(S)-1-Benzenesulfonyl-piperidine-2-carboxylic acid ((S)-1-amido-2-(2-methylphenyl)-ethyl)-amide;

(S)-1-Benzenesulfonyl-piperidine-2-carboxylic acid ((S)-1-cyclohexylamido-2-(4-methylphenyl)-ethyl)-amide;

(S)-1-Benzenesulfonyl-piperidine-2-carboxylic acid [(S)-2-(4-allyloxy-phenyl)-1-cyclohexylamido-ethyl]-amide;

(S)-1-(3-Trifluoromethyl-benzenesulfonyl)-piperidine-2-carboxylic acid [(S)-2-(4-allyloxy-phenyl)-1-cyclohexylcarbamoyl-ethyl]-amide;

(S)-1-(3-Trifluoromethyl-benzenesulfonyl)-piperidine-2-carboxylic acid ((S)-1-cyclohexylamido-2-(4-methylphenyl)-ethyl)-amide;

(S)-1-Benzenesulfonyl-piperidine-2-carboxylic acid [(S)-1-tert-butylamido-2-(1H-indol-3-yl)-ethyl]-amide;

(S)-1-Benzenesulfonyl-piperidine-2-carboxylic acid [(S)-1-(3-hydroxy-2,2-dimethyl-propylamido)-2-(4-isopropyl-phenyl)-ethyl]-amide;

(S)-1-Benzenesulfonyl-piperidine-2-carboxylic acid methyl-((S)-1-methylamido-2-(phenyl)-ethyl)-amide;

(S)-1-Benzenesulfonyl-piperidine-2-carboxylic acid [(S)-1-(3,3-dimethyl-butylamido)-2-(4-methoxyphenyl)-ethyl]-amide;

(S)-1-Benzenesulfonyl-piperidine-2-carboxylic acid [(S)-1-(2,2-dimethyl-propylamido)-2-(phenyl)-ethyl]-amide;

(S)-1-Benzenesulfonyl-piperidine-2-carboxylic acid [(S)-2-(4-(acetylamino)-phenyl)-1-amido-ethyl]-amide;

(S)-1-Benzenesulfonyl-piperidine-2-carboxylic acid [(S)-1-amido-2-(4-(hydroxymethyl)-phenyl)-ethyl]-amide;

(S)-1-(Naphthalene-2-sulfonyl)-piperidine-2-carboxylic acid [(S)-1-amido-2-(1H-indol-3-yl)-ethyl]-amide;

(S)-1-(3-Trifluoromethyl-benzenesulfonyl)-piperidine-2-carboxylic acid [(S)-1-(cyclohexylmethyl-amido)-2-(4-methylphenypethyl]-amide;

(S)-1-Benzenesulfonyl-piperidine-2-carboxylic acid [(S)-1-amido-2-(1H-indol-3-yl)-ethyl]-amide;

(S)-1-Benzenesulfonyl-piperidine-2-carboxylic acid {(S)-2-phenyl-1-[(thiophen-2-ylmethyl)-amido]-ethyl}-amide;

(S)-1-(3-Fluoro-benzenesulfonyl)-piperidine-2-carboxylic acid [(S)-2-[4-(3-methoxy-propoxy)-phenyl]-1-(tetrahydro-pyran-4-ylcarbamoyl)-ethyl]-amide;

(S)-1-(3-Trifluoromethyl-benzenesulfonyl)-piperidine-2-carboxylic acid {(S)-1-cyclohexylcarbamoyl-2-[4-(2-dimethylamino-ethoxy)-phenyl]-ethyl}-amide;

(S)-1-(3-Trifluoromethyl-benzenesulfonyl)-piperidine-2-carboxylic acid [(S)-2-(4-methoxy-phenyl)-1-(2-piperazin-1-yl-ethylcarbamoyl)-ethyl]-amide;

(S)-1-(3-Trifluoromethyl-benzenesulfonyl)-piperidine-2-carboxylic acid [(S)-1-(2-hydroxy-1,1-dimethyl-ethylcarbamoyl)-2-(4-methoxy-phenyl)-ethyl]-amide;

(S)-1-Benzenesulfonyl-piperidine-2-carboxylic acid ((S)-1-carbamoyl-2-phenyl-ethyl)-amide;

(S)-1-(3-Fluoro-benzenesulfonyl)-piperidine-2-carboxylic acid {(S)-2-[4-(3-methoxy-propoxy)-phenyl]-1-methylcarbamoyl-ethyl}-amide;

(S)-1-(3-Fluoro-benzenesulfonyl)-piperidine-2-carboxylic acid {(S)-1-((S)-2-methoxy-1-methyl-ethylcarbamoyl)-2-[4-(3-methoxy-propoxy)-phenyl]-ethyl}-amide; and (S)-1-(3-Hydroxy-benzenesulfonyl)-piperidine-2-carboxylic acid [(S)-2-(1H-indol-3-yl)-1-(naphthalen-2-ylcarbamoyl)-ethyl]-amide.

\* \* \* \* \*

UNITED STATES PATENT AND TRADEMARK OFFICE
CERTIFICATE OF CORRECTION

PATENT NO. : 7,777,042 B2
APPLICATION NO. : 11/567421
DATED : August 17, 2010
INVENTOR(S) : Kosley, Jr. et al.

It is certified that error appears in the above-identified patent and that said Letters Patent is hereby corrected as shown below:

In column 9, line 3-4, delete "glucouronic" and insert -- glucuronic --, therefor.

In column 25, line 53, delete "$C_{10}$" and insert -- $C_{1-10}$ --, therefor.

In column 26, line 66, delete "$C_{8-2}$" and insert -- $C_{8-12}$ --, therefor.

In column 33-34, Method A, C, D, line 5, delete "Piperadine" and insert -- Piperidine --, therefor.

In column 35, Method B, line 18, delete "Na(OAc$_3$)BH," and insert -- Na(OAc)$_3$BH, --, therefor.

In column 37-38, Method F, line 5, delete "Piperadine" and insert -- Piperidine --, therefor.

In column 62, line 20, delete "10M" and insert -- 1 µM --, therefor.

In column 62, line 33, delete "10M" and insert -- 1 µM --, therefor.

In column 88, line 30, delete "H-Seq" and insert -- H-5eq --, therefor.

In column 88, line 66, delete "17e," and insert -- 17e), --, therefor.

In column 89, line 55, delete "N-carbobenzyloxy-5-phenylalanine" and insert -- N-carbobenzyloxy-S-phenylalanine --, therefor.

In column 90, line 22, delete "ethyl)}" and insert -- ethyl} --, therefor.

In column 90, line 38, delete "D9.90" and insert -- δ9.90 --, therefor.

In column 90, line 53, delete "(-100 mL)" and insert -- (~100 mL) --, therefor.

Signed and Sealed this
Twenty-first Day of February, 2012

David J. Kappos
*Director of the United States Patent and Trademark Office*

CERTIFICATE OF CORRECTION (continued)
U.S. Pat. No. 7,777,042 B2

In column 96, line 36, delete "□1.07-1.39" and insert -- δ1.07-1.39 --, therefor.

In column 100, line 6, delete "Variano BondEluto," and insert -- Varian® BondElut®, --, therefor.

In column 105, line 58, delete "eluant" and insert -- eluent --, therefor.

In column 106, line 33, delete "eluant" and insert -- eluent --, therefor.

In column 115, line 40, in claim 5, delete "((S)1-" and insert -- ((S)-1- --, therefor.

In column 116, line 66, in claim 5, delete "-2[4-(2-" and insert -- -2-[4-(2- --, therefor.

In column 117, line 10, in claim 5, delete "-2[4-(3-" and insert -- -2-[4-(3- --, therefor.

In column 117, line 56, in claim 10, delete "((S)1-" and insert -- ((S)-1- --, therefor.

SEQUENCE LISTING

<160> NUMBER OF SEQ ID NOS: 2

<210> SEQ ID NO 1
<211> LENGTH: 706
<212> TYPE: DNA
<213> ORGANISM: Homo Sapiens

<400> SEQUENCE: 1 gccgccgcc cgctcagcgt ccgccgccgc catgggagtg caggtggaaa ccatctcccc      60

-continued

| | |
|---|---|
| aggagacggg cgcaccttcc ccaagcgcgg ccagacctgc gtggtgcact acaccgggat | 120 |
| gcttgaagat ggaaagaaat tgattcctc ccgggacaga acaagccct ttaagtttat | 180 |
| gctaggcaag caggaggtga tccgaggctg ggaagaaggg gttgcccaga tgagtgtggg | 240 |
| tcagagagcc aaactgacta tatctccaga ttatgcctat ggtgccactg gcacccagg | 300 |
| catcatccca ccacatgcca ctctcgtctt cgatgtggag cttctaaaac tggaatgaca | 360 |
| ggaatggcct cctcccttag ctccctgttc ttgggtaagg aaatggaata ctgaagggcc | 420 |
| cttcactgcc tttgctcctc ccatgttatg cccagcgttt gatgggtagc agagagaaca | 480 |
| aaaaacacca caaggctatt tttccccctg cattctttct gtattgagta tcctttcagt | 540 |
| gttattagtg tatgctttga atgtaaaaat tggtcaccct aaggaaagga attggcatgt | 600 |
| gtatgttccc agttcaactc atggagatgg cagctgttta aatgttttc tatgtagttt | 660 |
| ataaattaaa actgaattga ggactatgaa aaaaaaaaa aaaaaa | 706 |

<210> SEQ ID NO 2
<211> LENGTH: 3218
<212> TYPE: DNA
<213> ORGANISM: Homo Sapiens

<400> SEQUENCE: 2

| | |
|---|---|
| aacatacggc tctccatcaa acaaacgaa acaaaccaaa ctagcaaaat aggctgtccc | 60 |
| cagtgcaagt gcaggtgccg actttctcta tcgataggta ccgagctcca ccgcggtggc | 120 |
| ggccgctcta gaactagtgg atcccactat tcttaactcc tcaatcctag tactacattc | 180 |
| cagtggagca atcaaggacc aggcagaact aattttact tatttccaga cagttgggaa | 240 |
| cattccttcc agtgactcag aggttgggca ttggaaggta ttgagaacct gcaaagtgtc | 300 |
| tcaggctctg acccaaatcc ctgtgccacc tgcaagcacg ttctctggac gtaattttc | 360 |
| ttgagcagag caacagtaga gctttgtatg caacaatgta atttttacat tcttcacttg | 420 |
| cttaacatga ggtttggttc cacataaatg ttttgatctt atttattctt tgggaagatc | 480 |
| gcccctcaaa gagcttctg gctttttttt cccacataaa agaatacacg aaattgtcgc | 540 |
| agtcagcaag tgttggctaa agagacacag catcatgttt ctaacattaa tcataaatat | 600 |
| tatttaatta aaaactagtt tcttacaggt taggcctgat aacatcggaa ttagaatttg | 660 |
| agggcaaata actcaaaaga gagccttagg caagcattcg aatttacatt tattcagtgc | 720 |
| tctttatgag caaatctcca tgctaaaata ttttagggaa gagaaagcca tcataaaagc | 780 |
| aatgaaacaa tttctgattt tcagaaactc aatctaacat ggcagaagac acgcgaatag | 840 |
| ctatcttcaa tcaagattga ggaatcagaa ctcttagaaa agtataaacc aagacttgta | 900 |
| tagagaatct aagattaatt ttaaggagga taattttgga aaaactcagg gagatggtaa | 960 |
| tttttaagcc gggcttggat ggatggctac tactctcagg gcacaaatg aggggaaaaa | 1020 |
| gaactcaaga ccaaagaaac agcatgagca aggtccagg tactttttt ttttttttt | 1080 |
| taaagaaatg actaggccgg gtgcggtggc tcacgcctgt aatcccagca ctttgggagg | 1140 |
| ccaaggcggg cggatcacga ggtcaggaga tcgagaccat cctgattaac acagtgaaac | 1200 |
| cccgtctgta ctaaaaatag cacaaaaaaa aaaaaaaa aaattacccc ggcgtggcga | 1260 |
| gtgcctgtag tcccagctac tcgggaggct gaggcgggag aatggcgtga atccgggagg | 1320 |
| cagagcttgc agtgagccga gattgcgcca ctgcactcca gcctgggtga cagagcaaga | 1380 |
| ctccgtctca aaaaaaaaa aaaaaaaaa gaaatgacta gtcatccaat gtgccaaaat | 1440 |

-continued

```
aataataaac ttttattagt gattactata tgccaggaaa aattcctagc actttatgag   1500
gattacctga tttaattttc aactgaagca tggaagaaga tactattatc aagccagttt   1560
tacaggtaag gagactgagt catagaagat ttaagaagct aactcacaat catatagcta   1620
gatagtagag aaaacaggaa tcaagtttgc cccataactg caatactgtt atgtacacag   1680
tacaggtaga aatgcaaagt gggtttgaac caaagagtgg agggcttttt gtgccatccc   1740
aaagtgttgt acttcataaa taattacaa aggaggagaa agaatcctat ttttttttg     1800
tatctgaaag acaaagaaat aaaaagttaa aagattctc tgttagtact gattatttgg    1860
aacaataaat tgtttagagc tatgctgttc aatatagtag ycacctagca gtatgtgccc   1920
attaagcgtt tgaaatacga ctagaccaaa ttgagatgca ccgtaggctt aaaatataca   1980
ctgtatttct ttcctttttt ctttttttct tttttttttt tgagacgaa tcttactccc    2040
gtcacctagg ctggagtgta gtggcgcgat ctcggctcac tgcaacctcc acctttcttg   2100
ggttcaagcc attctcctgc ctcagcctcc ctagtagctg agattacagg catacaccac   2160
catgcctggc taattttttg tatttttagt agagatgggg tttcaccata ttggctaggc   2220
tggtctcaaa ctcctgacct tgtgatccac ccgcctcaac ctcccaaagt gctgggatta   2280
caggtgtgag ccactgcgtc tggaactccc cctgggaata ttctctacac tgtatttcaa   2340
ggagtttaat atgacaaaaa gaatgtcaaa taccttatta acaatgtagt atattgatgc   2400
atactgaagt actatttggg atatattggt ttaaatacaa tatattttaa aattatattt   2460
acctttaaa aaaacttta ttaatgaggc tactagatca tttaaattta cctgtgtggc     2520
ttgtattgta tttctactgg gcagtgctga tctagagcaa tttgaaactt gtggtagata   2580
ttttactaac caactctgat gaaggacttc ctcaccaaat tgttcttta accgcattct    2640
ttccttgctt tctggtcatt tgcaagaaaa attttaaaag gctgcccctt tgtaaaggtt   2700
tgagaggccc tagaatttcg ttttcactt gttcccaacc acaagcaaat gatcaatgtg    2760
ctttgtgaat gaagagtcaa cattttacca gggcgaagtg gggaggtaca aaaaatttc    2820
cagtccttga atggtgtgaa gtaaaagtgc cttcaaagaa tcccaccaga atggcacagg   2880
tgggcataat gggtctgtct catcgtcaaa ggacccaagg agtctaaagg aaactctaac   2940
tacaacaccc aaatgccaca aaaccttagt tattaataca aactatcatc cctgcctatc   3000
tgtcaccatc tcatcttaaa aaacttgtga aaatacgtaa tcctcaggag acttcaatta   3060
ggtataaata ccagcagcca gaggaggtgc agcacattgt tctgatcatc tgaagatcag   3120
ctattagaag agaaagatca gttaagtcct ttggacctga tcagcttgat acaagaacta   3180
ctgatttcaa cttctttggc ttaattctct cggaaacg                          3218
```